US009068983B2

(12) United States Patent
Bagnol et al.

(10) Patent No.: US 9,068,983 B2
(45) Date of Patent: *Jun. 30, 2015

(54) METHODS OF IDENTIFYING CANDIDATE COMPOUNDS OF THE HUMAN G PROTEIN-COUPLED RECEPTOR, GPR50, AS MODULATORS OF BODY MASS OR ADIPOSITY

(75) Inventors: Didier Bagnol, San Diego, CA (US); Chen W. Liaw, San Diego, CA (US)

(73) Assignee: Arena Pharmaceuticals, Inc., San Diego, CA (US)

( * ) Notice: Subject to any disclaimer, the term of this patent is extended or adjusted under 35 U.S.C. 154(b) by 625 days.

This patent is subject to a terminal disclaimer.

(21) Appl. No.: 13/175,727

(22) Filed: Jul. 1, 2011

(65) Prior Publication Data

US 2012/0207680 A1    Aug. 16, 2012

Related U.S. Application Data

(63) Continuation of application No. 12/092,538, filed as application No. PCT/US2006/043761 on Nov. 8, 2006, now Pat. No. 7,998,685.

(60) Provisional application No. 60/735,346, filed on Nov. 10, 2005.

(51) Int. Cl.
*G01N 33/53* (2006.01)
*G01N 33/567* (2006.01)
*G01N 33/566* (2006.01)
*C07K 14/705* (2006.01)
*A01K 67/027* (2006.01)
*C07K 14/72* (2006.01)
*C12N 15/85* (2006.01)

(52) U.S. Cl.
CPC .............. *G01N 33/566* (2013.01); *G01N 33/53* (2013.01); *C07K 14/705* (2013.01); *A01K 67/0276* (2013.01); *A01K 2217/075* (2013.01); *A01K 2227/105* (2013.01); *A01K 2267/0362* (2013.01); *C07K 14/723* (2013.01); *C07K 2319/00* (2013.01); *C12N 15/8509* (2013.01); *G01N 2333/726* (2013.01); *G01N 2500/04* (2013.01); *G01N 2800/044* (2013.01)

(58) Field of Classification Search
CPC . C07K 14/705; G01N 33/5008; G01N 33/53; G01N 33/566; G01N 2800/044; G01N 2033/435; G01N 2033/47; G01N 2033/50; G01N 2033/705; G01N 2500/04; G01N 2500/103

See application file for complete search history.

(56) References Cited

U.S. PATENT DOCUMENTS 6,555,339 B1    4/2003    Liaw et al.

FOREIGN PATENT DOCUMENTS

| WO | 03/006504 A2 | 1/2003 |
| WO | 03/104381 A | 12/2003 |
| WO | 2007058930 A1 | 5/2007 |

OTHER PUBLICATIONS

Filizola, et al., "BUNDLE: a program for building the transmembrane domains of G-protein-coupled receptors", J. Comput. Aided Mol. Des., 1998, 12:111-8.
Gouldson, et al., "Domain swapping in G-protein coupled receptor dimers", Protein Eng., 1998, 11:1181-93.
Gubitz, et al., "Assignment of the Melatonin-Related Receptor to Human Chromosome X (GPR50) and Mouse Chromosome X (Gpr50)", Genomics, 1999, 55:248-251.
Hebert, et al., "Structural and functional aspects of G protein-coupled receptor oligomerization", Biochem. Cell Biol., 1998, 76:1-11.
Inglese, et al., "Structure and mechanism of the G protein-coupled receptor kinases", J. Biol. Chem., 1993, 268:23735-8.
Ivanova, E., et al. The melatonin-related receptor (GPR50): Pattern of expression and phenotypic analyses in knock-out mice. Online May 1, 2005. Retrieved from the internet: URL: http://www.epbr-society.com/Congress/EPBRS-Congress2005_AbstractBooket_Poster.pdf.
Jackson, "Structure and function of G protein coupled receptors", Pharmacol. Ther., 1991, 50:425-42.
Lerner, M. Tools for investigating functional interactions between ligands and G-protein-coupled receptors. Trends in Neuroscience. 1994, vol. 17, No. 4, pp. 142-146.
Leung, et al., "Gonadotropin-releasing hormone receptor: gene structure, expression and regulation", Biol. Signals., 1996, 5:63-9.
Missale, et al., "Dopamine receptors: from structure to junction", Physiol. Rev., 1998, 78:189-225.
Ostrowski, et al., "Mutagenesis of the beta2-Adrenergic Receptor: How Structure Elucidates Function Annual Review of Pharmacology and Toxicology", 1992, 32:167-183.
Reppert, et al., "Cloning of a melatonin-related receptor from human pituitary", FEBS letters, 1996, 386:219-224.

(Continued)

*Primary Examiner* — Robert Landsman
(74) *Attorney, Agent, or Firm* — James S. Keddie; Bozicevic, Field & Franicis, LLP

(57) ABSTRACT

The present invention relates to methods of using a G protein-coupled receptor (GPCR) to screen one or more candidate compounds as a modulator of body mass or of adiposity or of percentage body fat in a subject or as a pharmaceutical agent for obesity and conditions related thereto. Inverse agonists and antagonists of the invention are useful as therapeutic agents for the prevention or treatment of obesity and conditions related thereto, including hypertension, insulin resistance, metabolic syndrome, Type 2 diabetes, dyslipidemia, atherosclerosis, coronary heart disease, and stroke. Agonists and partial agonists of the invention are useful as therapeutic agents for the prevention or treatment of disorders ameliorated by increasing body mass including, but not limited to, cachexia.

28 Claims, 13 Drawing Sheets

(56) References Cited

OTHER PUBLICATIONS

Sealfon, et al., "Functional domains of the gonadotropin-releasing hormone receptor", Cell Mol. Neurobiol., 1995, 15:25-42.

Wess, et al., "Identification of a small intracellular region of the muscarinic m3 receptor as a determinant of selective coupling to PI turnover", FEBS Letters, 1989, 258:133-6.

Wise, A., et al. Target validation of G-protein coupled receptors. Drug Discovery Today. 2002, vol. 7, No. 4, pp. 235-246.

Wong, et al., "Chimeric muscarinic cholinergic: beta-adrenergic receptors that activate Gs in response to muscarinic agonists", J. Biol. Chem., 1990, 265:6219-24.

Yeagle, et al., "Structure of the G-protein-coupled receptor, rhodopsin: a domain approach", Biochem. Soc. Trans., 1998, 26:520-31.

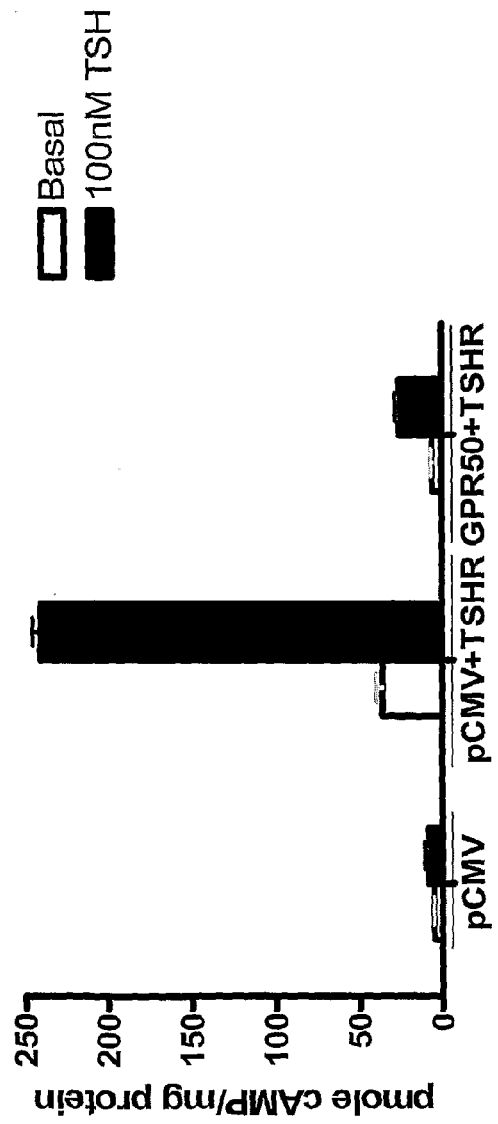
Figure 2. Endogenous GPR50 exhibits constitutive activity for decreasing the level of intracellular cAMP

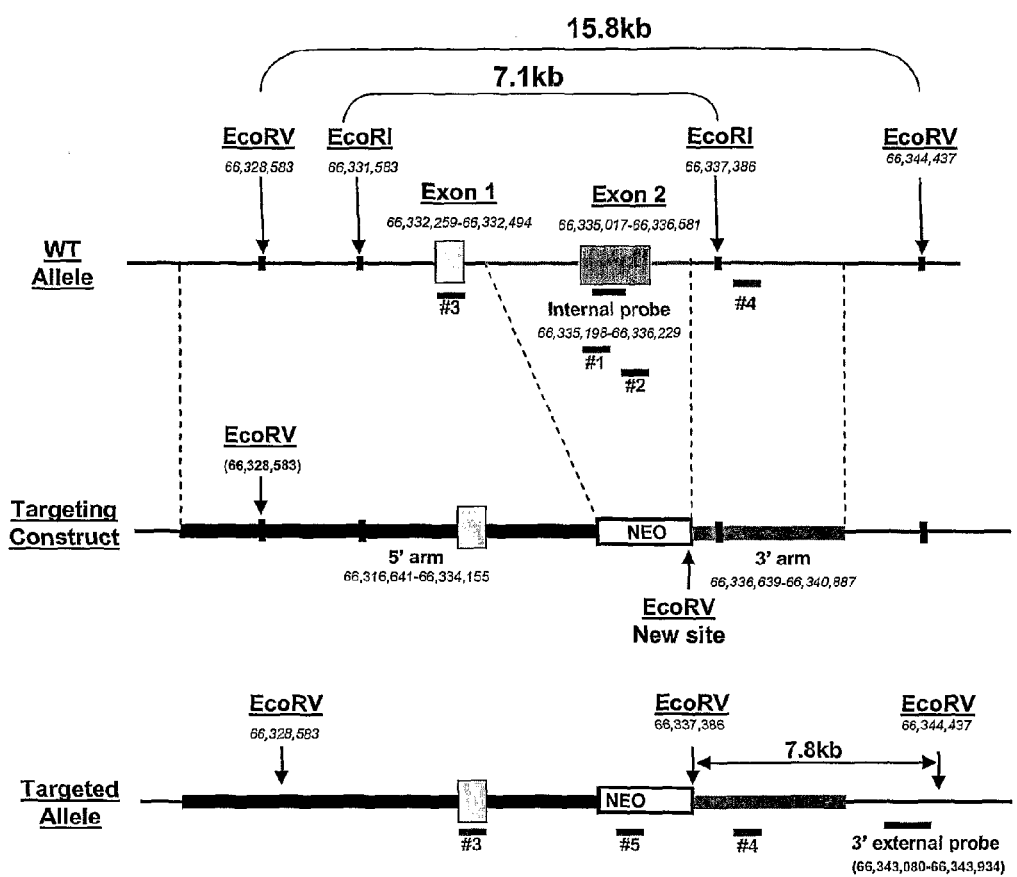
Figure 3A. Targeting strategy

Figure 3B.
Verification of GPR50 exon2 deletion
PCR of GPR50-knockout mouse
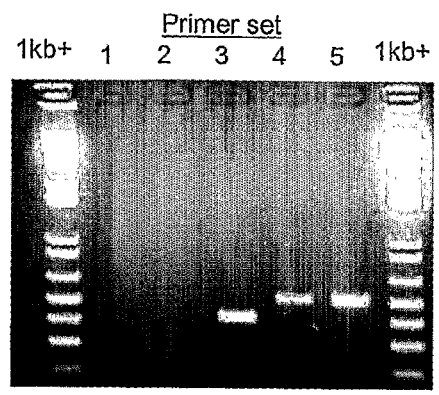
PCR of wild-type mouse
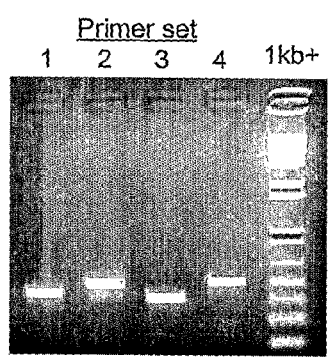

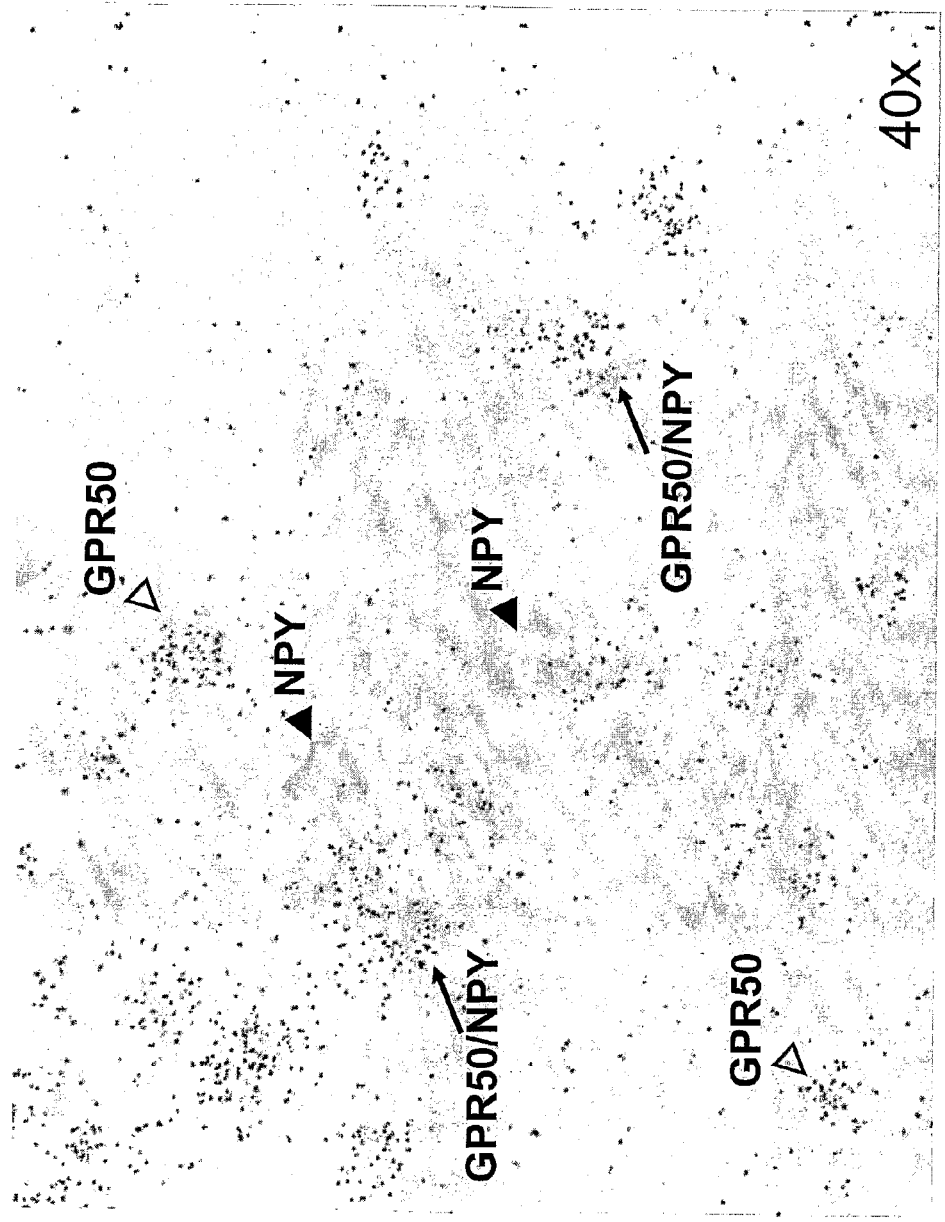

Figure 6B. Analysis of co-expression of GPR50 by NPY neurons in rat DMHc

| Rat # | Slide # | NPY total | double GRP50/NPY | % |
|---|---|---|---|---|
| NR32 | 1a | 47 | 19 | 40.4 |
| NR32 | 1b | 36 | 22 | 61.1 |
| NR32 | 2a | 26 | 14 | 53.8 |
| NR32 | 2b | 18 | 10 | 55.6 |
| | | 127 | 65 | 51.2 |

| Rat # | Slide # | NPY total | double GPR50/NPY | % |
|---|---|---|---|---|
| NR33 | 1a | 26 | 16 | 61.5 |
| NR33 | 1b | 35 | 21 | 60.0 |
| NR33 | 2a | 12 | 7 | 58.3 |
| NR33 | 2b | 16 | 7 | 43.8 |
| | | 89 | 51 | 57.3 |

| | NPY | % double GPR50/NPY |
|---|---|---|
| Total | 216 | 54.3 ± 2.8 |

Figure 7A
Food intake and body weight in the ad libitum fed and in the food-restricted rats over the two-week course of the experiment
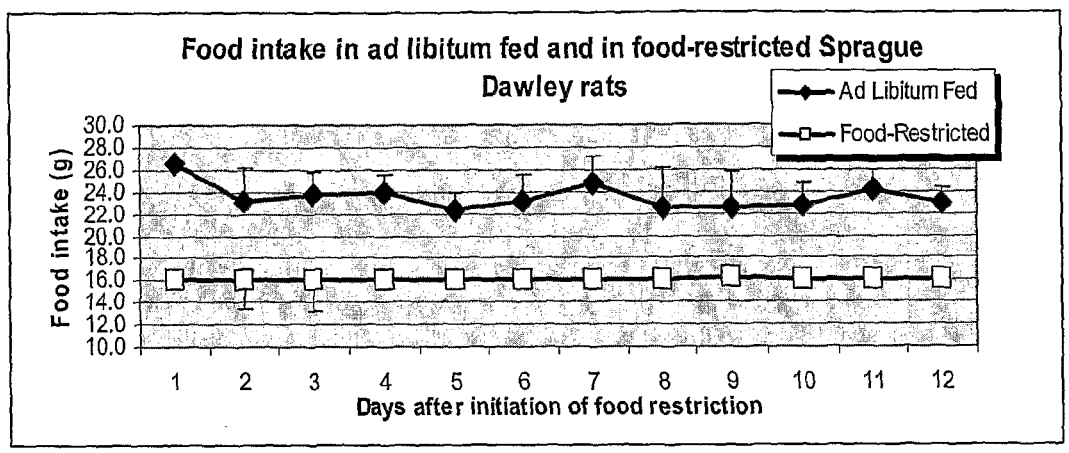
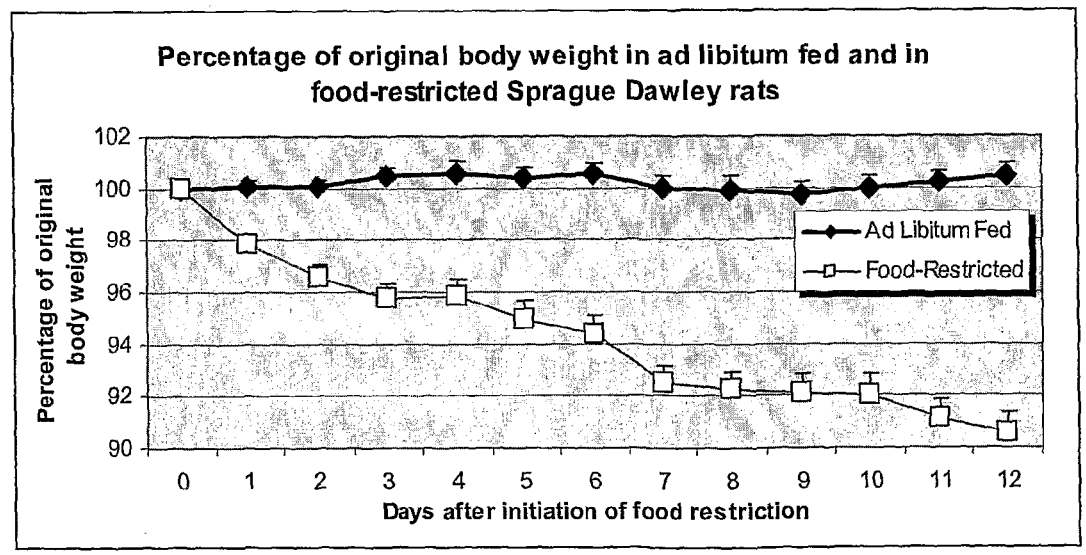

GPR50 mRNA expression in the central part of the
dorsomedial nucleus of the hypothalamus (DMHc) in
the ad libitum fed and in the food-restricted rats Figure 7C
GPR50 mRNA expression and NPY mRNA expression
in the central part of the dorsomedial nucleus of the
hypothalamus (DMHc) in the ad libitum fed and in the
food-restricted rats
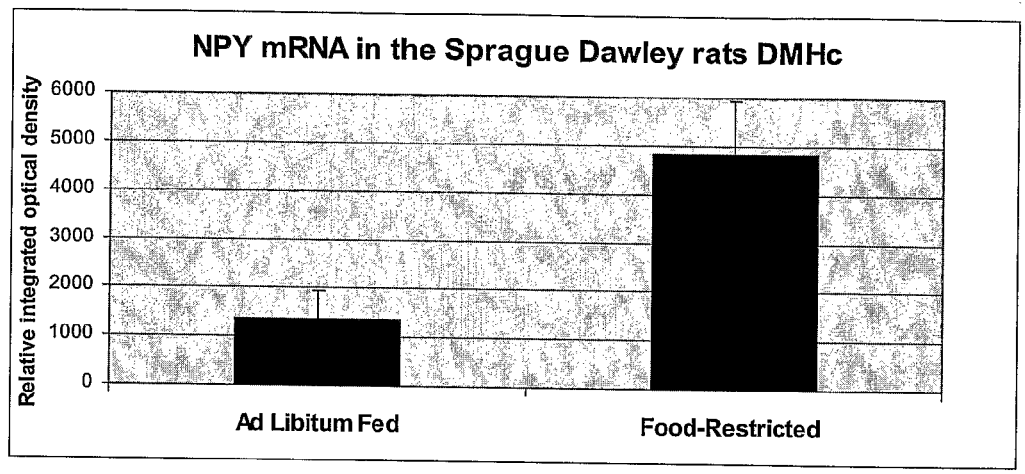
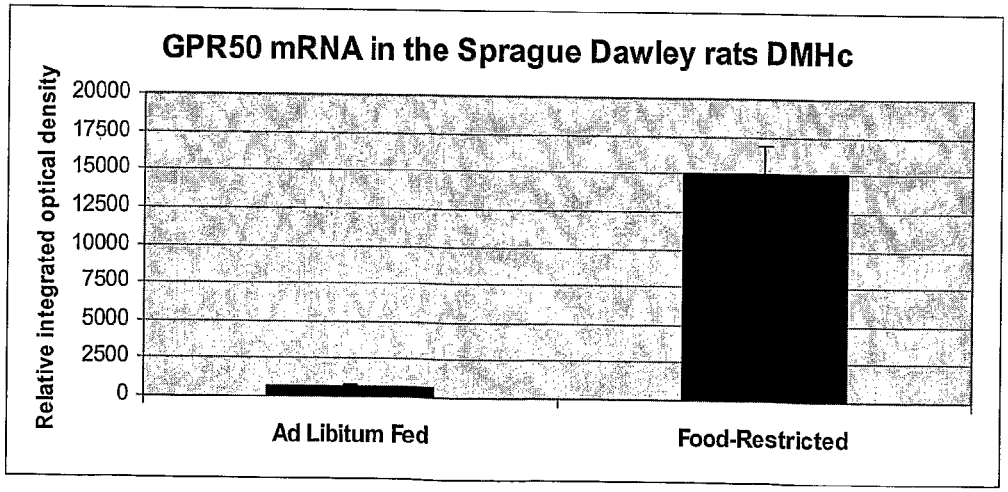

SEQUENCE LISTING

<160> NUMBER OF SEQ ID NOS: 27

<210> SEQ ID NO 1
<211> LENGTH: 1854
<212> TYPE: DNA
<213> ORGANISM: Homo sapiens

<400> SEQUENCE: 1

```
atggggccca ccctagcggt tcccaccccc tatggctgta ttggctgtaa gctacccag      60 ccagaatacc caccggctct aatcatcttt atgttctgcg cgatggttat caccatcgtt    120
gtagacctaa tcggcaactc catggtcatt ttggctgtga cgaagaacaa gaagctccgg    180
aattctggca acatcttcgt ggtcagtctc tctgtggccg atatgctggt ggccatctac    240
ccatacccct tgatgctgca tgccatgtcc attgggggct gggatctgag ccagttacag    300
tgccagatgg tcgggttcat cacagggctg agtgtggtcg gctccatctt caacatcgtg    360
gcaatcgcta tcaaccgtta ctgctacatc tgccacagcc tccagtacga acggatcttc    420
agtgtgcgca ataccgtcat ctacctggtc atcacctgga tcatgaccgt cctggctgtc    480
ctgcccaaca tgtacattgg caccatcgag tacgatcctc gcacctacac ctgcatcttc    540
aactatctga caaccctgt cttcactgtt accatcgtct gcatccactt cgtcctccct    600
ctcctcatcg tgggtttctg ctacgtgagg atctggacca aagtgctggc ggcccgtgac    660
cctgcagggc agaatcctga caaccaactt gctgaggttc gcaattttct aaccatgttt    720
gtgatcttcc tcctctttgc agtgtgctgg tgccctatca acgtgctcac tgtcttggtg    780
gctgtcagtc cgaaggagat ggcaggcaag atccccaact ggctttatct tgcagcctac    840
ttcatagcct acttcaacag ctgcctcaac gctgtgatct acgggctcct caatgagaat    900
ttccgaagag aatactggac catcttccat gctatgcggc accctatcat attcttctct    960
ggcctcatca gtgatattcg tgagatgcag gaggccgta ccctggcccg cgcccgtgcc    1020
catgctcgcg accaagctcg tgaacaagac cgtgcccatg cctgtcctgc tgtggaggaa    1080
accccgatga atgtccggaa tgttccatta cctggtgatg ctgcagctgg ccaccccgac    1140
cgtgcctctg gccaccctaa gccccattcc agatcctcct ctgcctatcg caaatctgcc    1200
tctacccacc acaagtctgt ctttagccac tccaaggctg cctctggtca cctcaagcct    1260
gtctctggcc actccaagcc tgcctctggt caccccaagt ctgccactgt ctaccctaag    1320
cctgcctctg tccatttcaa ggctgactct gtccatttca agggtgactc tgtccatttc    1380
aagcctgact ctgttcattt caagcctgct tccagcaacc ccaagcccat cactggccac    1440
cacgtctctg ctggcagcca ctccaagtct gccttcagtg ctgccaccag ccaccctaaa    1500
cccaccactg gccacatcaa gccagctacc agccatgctg agcccaccac tgctgactat    1560
cccaagcctg ccactaccag ccaccctaag cccactgctg ctgacaaccc tgagctctct    1620
gcctcccatt gccccgagat tcctgccatt gcccaccctg tgtctgacga cagtgacctc    1680
cctgagtcgg cctctagccc tgccgctggg cccaccaagc ctgctgccag ccagctggag    1740
```

-continued

```
tctgacacca tcgctgacct tcctgaccct actgtagtca ctaccagtac caatgattac    1800
catgatgtcg tggttgttga tgttgaagat gatcctgatg aaatggctgt gtga          1854
```

<210> SEQ ID NO 2
<211> LENGTH: 617
<212> TYPE: PRT
<213> ORGANISM: Homo sapiens
<220> FEATURE:
<221> NAME/KEY: VARIANT
<222> LOCATION: 493
<223> OTHER INFORMATION: Polymorphic amino acid Ser or Asn
<220> FEATURE:
<221> NAME/KEY: VARIANT
<222> LOCATION: 532
<223> OTHER INFORMATION: Polymorphic amino acid Thr or Ala
<220> FEATURE:
<221> NAME/KEY: VARIANT
<222> LOCATION: 606
<223> OTHER INFORMATION: Polymorphic amino acid Val or Ile

<400> SEQUENCE: 2

```
Met Gly Pro Thr Leu Ala Val Pro Thr Pro Tyr Gly Cys Ile Gly Cys
  1               5                  10                  15

Lys Leu Pro Gln Pro Glu Tyr Pro Pro Ala Leu Ile Ile Phe Met Phe
             20                  25                  30

Cys Ala Met Val Ile Thr Ile Val Val Asp Leu Ile Gly Asn Ser Met
         35                  40                  45

Val Ile Leu Ala Val Thr Lys Asn Lys Lys Leu Arg Asn Ser Gly Asn
     50                  55                  60

Ile Phe Val Val Ser Leu Ser Val Ala Asp Met Leu Val Ala Ile Tyr
 65                  70                  75                  80

Pro Tyr Pro Leu Met Leu His Ala Met Ser Ile Gly Gly Trp Asp Leu
                 85                  90                  95

Ser Gln Leu Gln Cys Gln Met Val Gly Phe Ile Thr Gly Leu Ser Val
            100                 105                 110

Val Gly Ser Ile Phe Asn Ile Val Ala Ile Ala Ile Asn Arg Tyr Cys
        115                 120                 125

Tyr Ile Cys His Ser Leu Gln Tyr Glu Arg Ile Phe Ser Val Arg Asn
    130                 135                 140

Thr Cys Ile Tyr Leu Val Ile Thr Trp Ile Met Thr Val Leu Ala Val
145                 150                 155                 160

Leu Pro Asn Met Tyr Ile Gly Thr Ile Glu Tyr Asp Pro Arg Thr Tyr
                165                 170                 175

Thr Cys Ile Phe Asn Tyr Leu Asn Asn Pro Val Phe Thr Val Thr Ile
            180                 185                 190

Val Cys Ile His Phe Val Leu Pro Leu Leu Ile Val Gly Phe Cys Tyr
        195                 200                 205

Val Arg Ile Trp Thr Lys Val Leu Ala Ala Arg Asp Pro Ala Gly Gln
    210                 215                 220

Asn Pro Asp Asn Gln Leu Ala Glu Val Arg Asn Phe Leu Thr Met Phe
225                 230                 235                 240

Val Ile Phe Leu Leu Phe Ala Val Cys Trp Cys Pro Ile Asn Val Leu
                245                 250                 255

Thr Val Leu Val Ala Val Ser Pro Lys Glu Met Ala Gly Lys Ile Pro
            260                 265                 270

Asn Trp Leu Tyr Leu Ala Ala Tyr Phe Ile Ala Tyr Phe Asn Ser Cys
        275                 280                 285
```

```
Leu Asn Ala Val Ile Tyr Gly Leu Leu Asn Glu Asn Phe Arg Arg Glu
    290                 295                 300

Tyr Trp Thr Ile Phe His Ala Met Arg His Pro Ile Ile Phe Phe Ser
305                 310                 315                 320

Gly Leu Ile Ser Asp Ile Arg Glu Met Gln Glu Ala Arg Thr Leu Ala
                325                 330                 335

Arg Ala Arg Ala His Ala Arg Asp Gln Ala Arg Glu Gln Asp Arg Ala
                340                 345                 350

His Ala Cys Pro Ala Val Glu Thr Pro Met Asn Val Arg Asn Val
            355                 360                 365

Pro Leu Pro Gly Asp Ala Ala Gly His Pro Asp Arg Ala Ser Gly
    370                 375                 380

His Pro Lys Pro His Ser Arg Ser Ser Ala Tyr Arg Lys Ser Ala
385                 390                 395                 400

Ser Thr His His Lys Ser Val Phe Ser His Ser Lys Ala Ala Ser Gly
                405                 410                 415

His Leu Lys Pro Val Ser Gly His Ser Lys Pro Ala Ser Gly His Pro
                420                 425                 430

Lys Ser Ala Thr Val Tyr Pro Lys Pro Ala Ser Val His Phe Lys Ala
                435                 440                 445

Asp Ser Val His Phe Lys Gly Asp Ser Val His Phe Lys Pro Asp Ser
    450                 455                 460

Val His Phe Lys Pro Ala Ser Ser Asn Pro Lys Pro Ile Thr Gly His
465                 470                 475                 480

His Val Ser Ala Gly Ser His Ser Lys Ser Ala Phe Ser Ala Ala Thr
                485                 490                 495

Ser His Pro Lys Pro Thr Thr Gly His Ile Lys Pro Ala Thr Ser His
                500                 505                 510

Ala Glu Pro Thr Thr Ala Asp Tyr Pro Lys Pro Ala Thr Thr Ser His
                515                 520                 525

Pro Lys Pro Thr Ala Ala Asp Asn Pro Glu Leu Ser Ala Ser His Cys
    530                 535                 540

Pro Glu Ile Pro Ala Ile Ala His Pro Val Ser Asp Asp Ser Asp Leu
545                 550                 555                 560

Pro Glu Ser Ala Ser Ser Pro Ala Ala Gly Pro Thr Lys Pro Ala Ala
                565                 570                 575

Ser Gln Leu Glu Ser Asp Thr Ile Ala Asp Leu Pro Asp Pro Thr Val
                580                 585                 590

Val Thr Thr Ser Thr Asn Asp Tyr His Asp Val Val Val Val Asp Val
                595                 600                 605

Glu Asp Asp Pro Asp Glu Met Ala Val
    610                 615

<210> SEQ ID NO 3
<211> LENGTH: 1842
<212> TYPE: DNA
<213> ORGANISM: Homo sapiens

<400> SEQUENCE: 3
atggggccca ccctagcggt tcccacccccc tatggctgta ttggctgtaa gctacccccag    60 ccagaatacc caccggctct aatcatcttt atgttctgcg cgatggttat caccatcgtt   120
gtagacctaa tcggcaactc catggtcatt ttggctgtga cgaagaacaa gaagctccgg   180
aattctggca acatcttcgt ggtcagtctc tctgtggccg atatgctggt ggccatctac   240
```

| | | |
|---|---|---|
| ccatacccttt tgatgctgca tgccatgtcc attgggggct gggatctgag ccagttacag | 300 |
| tgccagatgg tcgggttcat cacagggctg agtgtggtcg gctccatctt caacatcgtg | 360 |
| gcaatcgcta tcaaccgtta ctgctacatc tgccacagcc tccagtacga acggatcttc | 420 |
| agtgtgcgca atacctgcat ctacctggtc atcacctgga tcatgaccgt cctggctgtc | 480 |
| ctgcccaaca tgtacattgg caccatcgag tacgatcctc gcacctacac ctgcatcttc | 540 |
| aactatctga caaccctgt cttcactgtt accatcgtct gcatccactt cgtcctccct | 600 |
| ctcctcatcg tgggttttctg ctacgtgagg atctggacca aagtgctggc ggcccgtgac | 660 |
| cctgcagggc agaatcctga caaccaactt gctgaggttc gcaattttct aaccatgttt | 720 |
| gtgatcttcc tcctctttgc agtgtgctgg tgccctatca acgtgctcac tgtcttggtg | 780 |
| gctgtcagtc cgaaggagat ggcaggcaag atccccaact ggctttatct tgcagcctac | 840 |
| ttcatagcct acttcaacag ctgcctcaac gctgtgatct acgggctcct caatgagaat | 900 |
| ttccgaagag aatactggac catcttccat gctatgcggc accctatcat attcttctct | 960 |
| ggcctcatca gtgatattcg tgagatgcag gaggcccgta ccctggcccg cgcccgtgcc | 1020 |
| catgctcgcg accaagctcg tgaacaagac cgtgcccatg cctgtcctgc tgtggaggaa | 1080 |
| accccgatga atgtccggaa tgttccatta cctggtgatg ctgcagctgg ccaccccgac | 1140 |
| cgtgcctctg ccacccctaa gccccattcc agatcctcct ctgcctatcg caaatctgcc | 1200 |
| tctaccacc acaagtctgt ctttagccac tccaaggctg cctctggtca cctcaagcct | 1260 |
| gtctctggcc actccaagcc tgcctctggt caccccaagt ctgccactgt ctaccctaag | 1320 |
| cctgcctctg tccatttcaa ggctgactct gtccatttca agggtgactc tgtccatttc | 1380 |
| aagcctgact ctgttcattt caagcctgct tccagcaacc caagcccat cactggccac | 1440 |
| catgtctctg ctggcagcca ctccaagtct gccttcaatg ctgccaccag ccaccctaaa | 1500 |
| cccatcaagc cagctaccag ccatgctgag cccaccactg ctgactatcc caagcctgcc | 1560 |
| actaccagcc accctaagcc cgctgctgct gacaaccctg agctctctgc ctcccattgc | 1620 |
| cccgagattc ctgccattgc ccaccctgtg tctgacgaca gtgacctccc tgagtcggcc | 1680 |
| tctagccctg ccgctgggcc caccaagcct gctgccagcc agctggagtc tgacaccatc | 1740 |
| gctgaccttc ctgaccctac tgtagtcact accagtacca atgattacca tgatgtcgtg | 1800 |
| gttgttgatg ttgaagatga tcctgatgaa atggctgtgt ga | 1842 |

<210> SEQ ID NO 4
<211> LENGTH: 613
<212> TYPE: PRT
<213> ORGANISM: Homo sapiens
<220> FEATURE:
<221> NAME/KEY: VARIANT
<222> LOCATION: 493
<223> OTHER INFORMATION: Polymorphic amino acid Asn or Ser
<220> FEATURE:
<221> NAME/KEY: VARIANT
<222> LOCATION: 528
<223> OTHER INFORMATION: Polymorphic amino acid Ala or Thr
<220> FEATURE:
<221> NAME/KEY: VARIANT
<222> LOCATION: 602
<223> OTHER INFORMATION: Polymorphic amino acid Val or Ile

<400> SEQUENCE: 4

Met Gly Pro Thr Leu Ala Val Pro Thr Pro Tyr Gly Cys Ile Gly Cys
1               5                   10                  15

Lys Leu Pro Gln Pro Glu Tyr Pro Pro Ala Leu Ile Ile Phe Met Phe
            20                  25                  30

-continued

Cys Ala Met Val Ile Thr Ile Val Asp Leu Ile Gly Asn Ser Met
                35                  40                  45

Val Ile Leu Ala Val Thr Lys Asn Lys Lys Leu Arg Asn Ser Gly Asn
 50                  55                  60

Ile Phe Val Val Ser Leu Ser Val Ala Asp Met Leu Val Ala Ile Tyr
 65                  70                  75                  80

Pro Tyr Pro Leu Met Leu His Ala Met Ser Ile Gly Gly Trp Asp Leu
                85                  90                  95

Ser Gln Leu Gln Cys Gln Met Val Gly Phe Ile Thr Gly Leu Ser Val
                100                 105                 110

Val Gly Ser Ile Phe Asn Ile Val Ala Ile Ala Ile Asn Arg Tyr Cys
                115                 120                 125

Tyr Ile Cys His Ser Leu Gln Tyr Glu Arg Ile Phe Ser Val Arg Asn
                130                 135                 140

Thr Cys Ile Tyr Leu Val Ile Thr Trp Ile Met Thr Val Leu Ala Val
145                 150                 155                 160

Leu Pro Asn Met Tyr Ile Gly Thr Ile Glu Tyr Asp Pro Arg Thr Tyr
                165                 170                 175

Thr Cys Ile Phe Asn Tyr Leu Asn Asn Pro Val Phe Thr Val Thr Ile
                180                 185                 190

Val Cys Ile His Phe Val Leu Pro Leu Leu Ile Val Gly Phe Cys Tyr
                195                 200                 205

Val Arg Ile Trp Thr Lys Val Leu Ala Ala Arg Asp Pro Ala Gly Gln
                210                 215                 220

Asn Pro Asp Asn Gln Leu Ala Glu Val Arg Asn Phe Leu Thr Met Phe
225                 230                 235                 240

Val Ile Phe Leu Leu Phe Ala Val Cys Trp Cys Pro Ile Asn Val Leu
                245                 250                 255

Thr Val Leu Val Ala Val Ser Pro Lys Glu Met Ala Gly Lys Ile Pro
                260                 265                 270

Asn Trp Leu Tyr Leu Ala Ala Tyr Phe Ile Ala Tyr Phe Asn Ser Cys
                275                 280                 285

Leu Asn Ala Val Ile Tyr Gly Leu Leu Asn Glu Asn Phe Arg Arg Glu
                290                 295                 300

Tyr Trp Thr Ile Phe His Ala Met Arg His Pro Ile Ile Phe Phe Ser
305                 310                 315                 320

Gly Leu Ile Ser Asp Ile Arg Glu Met Gln Glu Ala Arg Thr Leu Ala
                325                 330                 335

Arg Ala Arg Ala His Ala Arg Asp Gln Ala Arg Glu Gln Asp Arg Ala
                340                 345                 350

His Ala Cys Pro Ala Val Glu Glu Thr Pro Met Asn Val Arg Asn Val
                355                 360                 365

Pro Leu Pro Gly Asp Ala Ala Ala Gly His Pro Asp Arg Ala Ser Gly
                370                 375                 380

His Pro Lys Pro His Ser Arg Ser Ser Ser Ala Tyr Arg Lys Ser Ala
385                 390                 395                 400

Ser Thr His His Lys Ser Val Phe Ser His Ser Lys Ala Ala Ser Gly
                405                 410                 415

His Leu Lys Pro Val Ser Gly His Ser Lys Pro Ala Ser Gly His Pro
                420                 425                 430

Lys Ser Ala Thr Val Tyr Pro Lys Pro Ala Ser Val His Phe Lys Ala
                435                 440                 445

```
Asp Ser Val His Phe Lys Gly Asp Ser Val His Phe Lys Pro Asp Ser
    450                 455                 460
Val His Phe Lys Pro Ala Ser Ser Asn Pro Lys Pro Ile Thr Gly His
465                 470                 475                 480
His Val Ser Ala Gly Ser His Ser Lys Ser Ala Phe Asn Ala Ala Thr
                485                 490                 495
Ser His Pro Lys Pro Ile Lys Pro Ala Thr Ser His Ala Glu Pro Thr
            500                 505                 510
Thr Ala Asp Tyr Pro Lys Pro Ala Thr Thr Ser His Pro Lys Pro Ala
        515                 520                 525
Ala Ala Asp Asn Pro Glu Leu Ser Ala Ser His Cys Pro Glu Ile Pro
530                 535                 540
Ala Ile Ala His Pro Val Ser Asp Asp Ser Asp Leu Pro Glu Ser Ala
545                 550                 555                 560
Ser Ser Pro Ala Ala Gly Pro Thr Lys Pro Ala Ala Ser Gln Leu Glu
                565                 570                 575
Ser Asp Thr Ile Ala Asp Leu Pro Asp Pro Thr Val Val Thr Thr Ser
            580                 585                 590
Thr Asn Asp Tyr His Asp Val Val Val Asp Val Glu Asp Asp Pro
        595                 600                 605
Asp Glu Met Ala Val
    610

<210> SEQ ID NO 5
<211> LENGTH: 1776
<212> TYPE: DNA
<213> ORGANISM: Mus musculus

<400> SEQUENCE: 5
atggccacgg tccccaagag caacatggga cctacaaagg cggttcccac cccattcggc     60
tgcattggct gtaagctgcc aaagcccgac tacccgccag ctctaatcat cttcatgttc    120
tgcgcaatgg tcatcacagt cgtcgtagac ctgatcggga actccatggt cattttggct    180
gtgaccaaga caagaagct ccgaaattct ggcaacatct tgtggccag cctctctgtg      240
gcagacatgc tggtggccat ctaccctac cctttgatgc tgtatgccat gtcagttggg     300
ggctgggatc tgagtcagct ccagtgccag atggtcgggt tggtcacagg actgagcgta    360
gtcggttcca tcttcaacat tactgccatt gccatcaacc gttactgcta catctgccac    420
agcctccaat acaagcggat cttcagcctg cgcaacactt gcatctatct ggtcgttacc    480
tgggtcatga ctgtcctggc tgtcctgcct aacatgtaca ttggcaccat tgagtatgac    540
cctcgcacct acacctgcat cttcaactat gtgaacaatc tgcctttac cgtgaccatt    600
gtctgcatcc acttcgtcct ccctctcatc atagttggtt attgctacac gaaaatctgg    660
atcaaagtgc tggcagcccg tgacccagct ggacagaatc tgacaaacca gtttgctgag    720
gttcgaaatt ttctaaccat gtttgtgatc ttcctccttt ttgcagtgtg ctggtgccct    780
gtcaatgtgc tcactgtgtt ggtggctgtc attccaaagg aaatggcagg caagatcccc    840
aactggcttt atcttgcagc ctactgcata gcctacttca acagctgcct caacgccatc    900
atctacgta tcctcaatga gtttcgga agaatact ggaccatctt ccatgctatg          960
cggcacccta tcctgttcat ctctcacctc atcagtgata ttcgggagac ttgggagacc   1020
cgagctctca ctcgtgcccg tgtccgtgcc cgtgatcaag tccgagagca agagcgtgct   1080
cgtgcctgtg tcgctgtgga ggggacccca aggaacgtcc ggaatgttct actgcctggt   1140
```

```
gatgcatcag cacccactc tgatcgtgcc tctgtccgtc ccaagcccca aaccaggtct   1200
acttctgtct accgcaaacc tgcctctatc caccacaagt ctatttctgg ccacccaag   1260 tctgcctctg tttaccctaa gccagcctcc tctgtccatt gcaagcctgc ctctgtccat   1320
ttcaaacccg cctctgttca tttcaagggt gactctgtct atttcaaggg agacactgtc   1380
cattacaggg ctgcttccaa acttgtcacc agtcaccgta tctctgctgg cccttccacc   1440
agtcacccta catccatggc tggctacatt aaatctggta ccagccaccc tgccaccacc   1500
actgttgact atctcgaacc tgccaccacc agccactctg tgctcactgc tgtcgacctc   1560
cctgaggtct cagcctccca ttgccttgag atgaccagca ctggccacct cagagctgac   1620
atttctgcct ctgtccttcc ttctgtaccc ttcgagcttg ctgccacccc tcctgatacc   1680
actgcaatcc ccattgcctc tggtgattac cgcaaggtcg tgcttattga tgatgattct   1740
gatgattctg attgctctga tgagatggct gtgtga                            1776
```

<210> SEQ ID NO 6
<211> LENGTH: 591
<212> TYPE: PRT
<213> ORGANISM: Mus musculus

<400> SEQUENCE: 6

```
Met Ala Thr Val Pro Lys Ser Asn Met Gly Pro Thr Lys Ala Val Pro
1               5                   10                  15

Thr Pro Phe Gly Cys Ile Gly Cys Lys Leu Pro Lys Pro Asp Tyr Pro
            20                  25                  30

Pro Ala Leu Ile Ile Phe Met Phe Cys Ala Met Val Ile Thr Val Val
        35                  40                  45

Val Asp Leu Ile Gly Asn Ser Met Val Ile Leu Ala Val Thr Lys Asn
    50                  55                  60

Lys Lys Leu Arg Asn Ser Gly Asn Ile Phe Val Ala Ser Leu Ser Val
65                  70                  75                  80

Ala Asp Met Leu Val Ala Ile Tyr Pro Tyr Pro Leu Met Leu Tyr Ala
                85                  90                  95

Met Ser Val Gly Gly Trp Asp Leu Ser Gln Leu Gln Cys Gln Met Val
            100                 105                 110

Gly Leu Val Thr Gly Leu Ser Val Val Gly Ser Ile Phe Asn Ile Thr
        115                 120                 125

Ala Ile Ala Ile Asn Arg Tyr Cys Tyr Ile Cys His Ser Leu Gln Tyr
    130                 135                 140

Lys Arg Ile Phe Ser Leu Arg Asn Thr Cys Ile Tyr Leu Val Val Thr
145                 150                 155                 160

Trp Val Met Thr Val Leu Ala Val Leu Pro Asn Met Tyr Ile Gly Thr
                165                 170                 175

Ile Glu Tyr Asp Pro Arg Thr Tyr Thr Cys Ile Phe Asn Tyr Val Asn
            180                 185                 190

Asn Pro Ala Phe Thr Val Thr Ile Val Cys Ile His Phe Val Leu Pro
        195                 200                 205

Leu Ile Ile Val Gly Tyr Cys Tyr Thr Lys Ile Trp Ile Lys Val Leu
    210                 215                 220

Ala Ala Arg Asp Pro Ala Gly Gln Asn Pro Asp Asn Gln Phe Ala Glu
225                 230                 235                 240

Val Arg Asn Phe Leu Thr Met Phe Val Ile Phe Leu Leu Phe Ala Val
                245                 250                 255

Cys Trp Cys Pro Val Asn Val Leu Thr Val Leu Val Ala Val Ile Pro
```

```
                    260                 265                 270
Lys Glu Met Ala Gly Lys Ile Pro Asn Trp Leu Tyr Leu Ala Ala Tyr
                275                 280                 285
Cys Ile Ala Tyr Phe Asn Ser Cys Leu Asn Ala Ile Ile Tyr Gly Ile
            290                 295                 300
Leu Asn Glu Ser Phe Arg Arg Glu Tyr Trp Thr Ile Phe His Ala Met
305                 310                 315                 320
Arg His Pro Ile Leu Phe Ile Ser His Leu Ile Ser Asp Ile Arg Glu
                325                 330                 335
Thr Trp Glu Thr Arg Ala Leu Thr Arg Ala Arg Val Arg Ala Arg Asp
                340                 345                 350
Gln Val Arg Glu Gln Glu Arg Ala Arg Ala Cys Val Ala Val Glu Gly
                355                 360                 365
Thr Pro Arg Asn Val Arg Asn Val Leu Leu Pro Gly Asp Ala Ser Ala
            370                 375                 380
Pro His Ser Asp Arg Ala Ser Val Arg Pro Lys Pro Gln Thr Arg Ser
385                 390                 395                 400
Thr Ser Val Tyr Arg Lys Pro Ala Ser Ile His His Lys Ser Ile Ser
                405                 410                 415
Gly His Pro Lys Ser Ala Ser Val Tyr Pro Lys Pro Ala Ser Ser Val
                420                 425                 430
His Cys Lys Pro Ala Ser Val His Phe Lys Pro Ala Ser Val His Phe
                435                 440                 445
Lys Gly Asp Ser Val Tyr Phe Lys Gly Asp Thr Val His Tyr Arg Ala
450                 455                 460
Ala Ser Lys Leu Val Thr Ser His Arg Ile Ser Ala Gly Pro Ser Thr
465                 470                 475                 480
Ser His Pro Thr Ser Met Ala Gly Tyr Ile Lys Ser Gly Thr Ser His
                485                 490                 495
Pro Ala Thr Thr Thr Val Asp Tyr Leu Glu Pro Ala Thr Thr Ser His
                500                 505                 510
Ser Val Leu Thr Ala Val Asp Leu Pro Glu Val Ser Ala Ser His Cys
                515                 520                 525
Leu Glu Met Thr Ser Thr Gly His Leu Arg Ala Asp Ile Ser Ala Ser
            530                 535                 540
Val Leu Pro Ser Val Pro Phe Glu Leu Ala Ala Thr Pro Pro Asp Thr
545                 550                 555                 560
Thr Ala Ile Pro Ile Ala Ser Gly Asp Tyr Arg Lys Val Val Leu Ile
                565                 570                 575
Asp Asp Asp Ser Asp Asp Ser Asp Cys Ser Asp Glu Met Ala Val
                580                 585                 590

<210> SEQ ID NO 7
<211> LENGTH: 1785
<212> TYPE: DNA
<213> ORGANISM: Rattus norvegicus

<400> SEQUENCE: 7
atggccacgg tccccaagag caacatggga cctacgaagg caattcccac cccattcggc    60
tgcattagct gtaagctgcc aaagcccgac taccaccag cgctaatcat cttcgtgttc    120
tgcgcaatgg tcatcactgt cgtcgtagac ctgattggaa actccatggt cattttggct    180
gtgaccaaga caagaagct ccgaaattct ggcaacatct ttgtggccag cctctctgtg    240
gcagacatgc tcgtggccat ctaccccgtac cctttgatgc tgtataccat gtcagttggg    300
```

```
ggctgggatc tgagtcagct ccagtgccag atggtcgggt tggtcacagg actgagtgta    360
gtcggttcta tcttcaacat tactgccatt gccatcaacc ggtactgcta catctgccac    420
agcctccagt acaagcggat cttcagcctg cgcaacactt gcatctatct ggttgttacc    480
tgggtcatga ctgttctggc tgtcctgcct aatgtgtaca ttggcaccat tgagtatgac    540
cctcgcacct acacctgcat cttcaactat gtgaacaacc tgcctttac tgtgaccatt    600 gtctgcatcc acttcgtcct ccctctcatc atagtcggtt attgctacac aaaaatctgg    660
atcaaagtgc tggcagcccg ggacccagct ggacagaatc ctgacaacca gtttgctgag    720
gttcgaaatt ttctaaccat gtttgtgatc ttcctccttt ttgcagtgtg ctggtgccct    780
gtcaatgtgc tcactgtgct ggtggctgtc attccaaagg aaatggcagg caagatcccc    840
aactggcttt atcttgcagc ctactgcata gcctacttca acagctgcct caacgccatc    900
atctacggta tcctcaatga gtttccgaa agagaatact ggaccatctt ccatgctatg    960
cggcacccta tcctgttcat ctctcacctc atcagcgcta ttcgggaggc ttgggagacc   1020
cgagttctca ctcgtgcccg cgtccgtgcc cgtgatcaag tccgagaaca agatcgtgct   1080
cgtgcctgtg tcgctgtggc gggaaccccg aggaacgtcc ggaatgttct actgcctggt   1140
gatgcagcag catccccttc tgatcgtgcc tctgtccgtc ccagtcccaa accaggtct    1200 acttctgtct accgcaaacc tgcctctatc caccataagt ctatttctgg tcaccccaag   1260
tctgcctctg tctaccctag gccagcttcc tctgtccatt gcaaacctgc ctctgtccat   1320
ttcaaaccca catctgttca tttcaagggc gactctgtct atttcaaggg agacactgtc   1380
catttcaggg ctgcttccaa acttgtcacc agtcaccgta tctctgctgg cccttccacc   1440
agtcacccta catccatggc tggctacatt aaatctggta ccagccaccg tgcgaccacc   1500
actgttgact atctcgaacc tgccaccacc agccactctg tgctcactgc tgtcgacctc   1560
cctgaggtct cagcctccca ttgccttgag atgaccacct ttggccacct caaacccgac   1620
attcctgcct ccatccttcc cactgtaccc cctgagcttg ctgtcacctc tgccacccct   1680
cctgatgcca ctgtaatccc cattcccact ggtgattacc gcaaggtcgt gcttattgat   1740
gatgattccg atgattctga ttgttctgat gagatggcgg tgtga               1785
```

<210> SEQ ID NO 8
<211> LENGTH: 594
<212> TYPE: PRT
<213> ORGANISM: Rattus norvegicus

<400> SEQUENCE: 8

```
Met Ala Thr Val Pro Lys Ser Asn Met Gly Pro Thr Lys Ala Ile Pro
1               5                   10                  15

Thr Pro Phe Gly Cys Ile Ser Cys Lys Leu Pro Lys Pro Asp Tyr Pro
            20                  25                  30

Pro Ala Leu Ile Ile Phe Val Phe Cys Ala Met Val Ile Thr Val Val
        35                  40                  45

Val Asp Leu Ile Gly Asn Ser Met Val Ile Leu Ala Val Thr Lys Asn
    50                  55                  60

Lys Lys Leu Arg Asn Ser Gly Asn Ile Phe Val Ala Ser Leu Ser Val
65                  70                  75                  80

Ala Asp Met Leu Val Ala Ile Tyr Pro Tyr Pro Leu Met Leu Tyr Thr
                85                  90                  95

Met Ser Val Gly Gly Trp Asp Leu Ser Gln Leu Gln Cys Gln Met Val
            100                 105                 110
```

```
Gly Leu Val Thr Gly Leu Ser Val Val Gly Ser Ile Phe Asn Ile Thr
            115                 120                 125

Ala Ile Ala Ile Asn Arg Tyr Cys Tyr Ile Cys His Ser Leu Gln Tyr
130                 135                 140

Lys Arg Ile Phe Ser Leu Arg Asn Thr Cys Ile Tyr Leu Val Val Thr
145                 150                 155                 160

Trp Val Met Thr Val Leu Ala Val Leu Pro Asn Val Tyr Ile Gly Thr
                165                 170                 175

Ile Glu Tyr Asp Pro Arg Thr Tyr Thr Cys Ile Phe Asn Tyr Val Asn
                180                 185                 190

Asn Pro Ala Phe Thr Val Thr Ile Val Cys Ile His Phe Val Leu Pro
            195                 200                 205

Leu Ile Ile Val Gly Tyr Cys Tyr Thr Lys Ile Trp Ile Lys Val Leu
        210                 215                 220

Ala Ala Arg Asp Pro Ala Gly Gln Asn Pro Asp Asn Gln Phe Ala Glu
225                 230                 235                 240

Val Arg Asn Phe Leu Thr Met Phe Val Ile Phe Leu Leu Phe Ala Val
                245                 250                 255

Cys Trp Cys Pro Val Asn Val Leu Thr Val Leu Val Ala Val Ile Pro
            260                 265                 270

Lys Glu Met Ala Gly Lys Ile Pro Asn Trp Leu Tyr Leu Ala Ala Tyr
        275                 280                 285

Cys Ile Ala Tyr Phe Asn Ser Cys Leu Asn Ala Ile Ile Tyr Gly Ile
290                 295                 300

Leu Asn Glu Ser Phe Arg Arg Glu Tyr Trp Thr Ile Phe His Ala Met
305                 310                 315                 320

Arg His Pro Ile Leu Phe Ile Ser His Leu Ile Ser Ala Ile Arg Glu
                325                 330                 335

Ala Trp Glu Thr Arg Val Leu Thr Arg Ala Arg Val Arg Ala Arg Asp
            340                 345                 350

Gln Val Arg Glu Gln Asp Arg Ala Arg Ala Cys Val Ala Val Ala Gly
        355                 360                 365

Thr Pro Arg Asn Val Arg Asn Val Leu Leu Pro Gly Asp Ala Ala Ala
    370                 375                 380

Ser Pro Ser Asp Arg Ala Ser Val Arg Pro Lys Ser Gln Thr Arg Ser
385                 390                 395                 400

Thr Ser Val Tyr Arg Lys Pro Ala Ser Ile His His Lys Ser Ile Ser
                405                 410                 415

Gly His Pro Lys Ser Ala Ser Val Tyr Pro Arg Pro Ala Ser Ser Val
            420                 425                 430

His Cys Lys Pro Ala Ser Val His Phe Lys Pro Thr Ser Val His Phe
        435                 440                 445

Lys Gly Asp Ser Val Tyr Phe Lys Gly Asp Thr Val His Phe Arg Ala
450                 455                 460

Ala Ser Lys Leu Val Thr Ser His Arg Ile Ser Ala Gly Pro Ser Thr
465                 470                 475                 480

Ser His Pro Thr Ser Met Ala Gly Tyr Ile Lys Ser Gly Thr Ser His
                485                 490                 495

Arg Ala Thr Thr Thr Val Asp Tyr Leu Glu Pro Ala Thr Thr Ser His
            500                 505                 510

Ser Val Leu Thr Ala Val Asp Leu Pro Glu Val Ser Ala Ser His Cys
        515                 520                 525
```

```
Leu Glu Met Thr Thr Phe Gly His Leu Lys Pro Asp Ile Pro Ala Ser
        530                 535                 540

Ile Leu Pro Thr Val Pro Pro Glu Leu Ala Val Thr Ser Ala Thr Pro
545                 550                 555                 560

Pro Asp Ala Thr Val Ile Pro Ile Pro Thr Gly Asp Tyr Arg Lys Val
                565                 570                 575

Val Leu Ile Asp Asp Asp Ser Asp Asp Ser Asp Cys Ser Asp Glu Met
                580                 585                 590

Ala Val

<210> SEQ ID NO 9
<211> LENGTH: 30
<212> TYPE: DNA
<213> ORGANISM: Artificial Sequence
<220> FEATURE:
<223> OTHER INFORMATION: synthetic oligonucleotide

<400> SEQUENCE: 9
ggaaagctta acgatcccca ggagcaacat                                    30

<210> SEQ ID NO 10
<211> LENGTH: 31
<212> TYPE: DNA
<213> ORGANISM: Artificial Sequence
<220> FEATURE:
<223> OTHER INFORMATION: synthetic oligonucleotide

<400> SEQUENCE: 10
ctgggatcct acgagagcat ttttcacaca g                                  31

<210> SEQ ID NO 11
<211> LENGTH: 6
<212> TYPE: PRT
<213> ORGANISM: Artificial Sequence
<220> FEATURE:
<223> OTHER INFORMATION: synthetic peptide

<400> SEQUENCE: 11

Thr Leu Glu Ser Ile Met
1               5

<210> SEQ ID NO 12
<211> LENGTH: 5
<212> TYPE: PRT
<213> ORGANISM: Artificial Sequence
<220> FEATURE:
<223> OTHER INFORMATION: synthetic peptide

<400> SEQUENCE: 12

Glu Tyr Asn Leu Val
1               5

<210> SEQ ID NO 13
<211> LENGTH: 5
<212> TYPE: PRT
<213> ORGANISM: Artificial Sequence
<220> FEATURE:
<223> OTHER INFORMATION: synthatic peptide

<400> SEQUENCE: 13

Asp Cys Gly Leu Phe
1               5

<210> SEQ ID NO 14
```

```
<211> LENGTH: 36
<212> TYPE: DNA
<213> ORGANISM: Artificial Sequence
<220> FEATURE:
<223> OTHER INFORMATION: synthetic oligonucleotide

<400> SEQUENCE: 14
gatcaagctt ccatggcgtg ctgcctgagc gaggag                              36

<210> SEQ ID NO 15
<211> LENGTH: 53
<212> TYPE: DNA
<213> ORGANISM: Artificial Sequence
<220> FEATURE:
<223> OTHER INFORMATION: synthetic oligonucleotide

<400> SEQUENCE: 15
gatcggatcc ttagaacagg ccgcagtcct tcaggttcag ctgcaggatg gtg           53

<210> SEQ ID NO 16
<211> LENGTH: 1062
<212> TYPE: DNA
<213> ORGANISM: Artificial Sequence
<220> FEATURE:
<223> OTHER INFORMATION: synthetic oligonucleotide

<400> SEQUENCE: 16
atggcgtgct gcctgagcga ggaggccaag gaagcccgga ggatcaacga cgagatcgag    60
cggcagctgc gcagggacaa gcgcgacgcc cgccgggagc tcaagctgct gctgctgggg   120
acaggggaga gtggcaagtc gaccttcatc aagcagatga ggatcatcca cgggtcgggc   180
tactctgacg aagacaagcg cggcttcacc aagctggtgt atcagaacat cttcacggcc   240
atgcaggcca tgatcagagc gatggacaca ctcaagatcc catacaagta tgaacacaat   300
aaggctcatg cacaattggt tcgagaggtt gatgtggaga aggtgtctgc ttttgacgtc   360
cccgactacg cggcaataaa gagcttgtgg aatgatcctg aatccaggag tgctacgac   420 agacgacggg aatatcagtt atctgactct accaaatact atctgaatga cttggaccgt   480
gtagccgacc cttcctatct gcctacacaa caagacgtgc ttagagttcg agtccccact   540
acagggatca tcgaatacccc ctttgactta caaagtgtca ttttcagaat ggtcgatgta   600
gggggccaaa ggtcagagag aagaaaatgg atccactgct ttgaaaatgt cacctccatc   660
atgtttctag tagcgcttag cgaatatgat caagttcttg tggagtcaga caatgagaac   720
cgcatggagg agagcaaagc actctttaga acaattatca cctacccctg gttccagaac   780
tcctctgtga ttctgttctt aaacaagaaa gatcttctag aggagaaaat catgtattcc   840
cacctagtcg actacttccc agaatatgat ggacccagag agatgcccca ggcagctcga   900
gaattcatcc tgaaaatgtt cgtggacctg aaccccgaca gtgacaaaat catctactcc   960
cacttcacgt gcgccacaga taccgagaac atccgcttcg tctttgcagc cgtcaaggac  1020
accatcctgc agctgaacct gaaggactgc ggcctgttct aa                     1062

<210> SEQ ID NO 17
<211> LENGTH: 353
<212> TYPE: PRT
<213> ORGANISM: Artificial Sequence
<220> FEATURE:
<223> OTHER INFORMATION: chimeric polypeptide

<400> SEQUENCE: 17

Met Ala Cys Cys Leu Ser Glu Glu Ala Lys Glu Ala Arg Arg Ile Asn
```

```
  1               5                  10                 15
Asp Glu Ile Glu Arg Gln Leu Arg Arg Asp Lys Arg Asp Ala Arg Arg
                 20                  25                 30
Glu Leu Lys Leu Leu Leu Gly Thr Gly Glu Ser Gly Lys Ser Thr
             35                  40                 45
Phe Ile Lys Gln Met Arg Ile Ile His Gly Ser Gly Tyr Ser Asp Glu
         50                  55                 60
Asp Lys Arg Gly Phe Thr Lys Leu Val Tyr Gln Asn Ile Phe Thr Ala
65                  70                  75                 80
Met Gln Ala Met Ile Arg Ala Met Asp Thr Leu Lys Ile Pro Tyr Lys
                 85                  90                 95
Tyr Glu His Asn Lys Ala His Ala Gln Leu Val Arg Glu Val Asp Val
             100                 105                110
Glu Lys Val Ser Ala Phe Asp Val Pro Asp Tyr Ala Ala Ile Lys Ser
             115                 120                125
Leu Trp Asn Asp Pro Gly Ile Gln Glu Cys Tyr Asp Arg Arg Arg Glu
130                 135                 140
Tyr Gln Leu Ser Asp Ser Thr Lys Tyr Tyr Leu Asn Asp Leu Asp Arg
145                 150                 155                160
Val Ala Asp Pro Ser Tyr Leu Pro Thr Gln Gln Asp Val Leu Arg Val
                 165                 170                175
Arg Val Pro Thr Thr Gly Ile Ile Glu Tyr Pro Phe Asp Leu Gln Ser
             180                 185                190
Val Ile Phe Arg Met Val Asp Val Gly Gly Gln Arg Ser Glu Arg Arg
             195                 200                205
Lys Trp Ile His Cys Phe Glu Asn Val Thr Ser Ile Met Phe Leu Val
210                 215                 220
Ala Leu Ser Glu Tyr Asp Gln Val Leu Val Glu Ser Asp Asn Glu Asn
225                 230                 235                240
Arg Met Glu Glu Ser Lys Ala Leu Phe Arg Thr Ile Ile Thr Tyr Pro
                 245                 250                255
Trp Phe Gln Asn Ser Ser Val Ile Leu Phe Leu Asn Lys Lys Asp Leu
             260                 265                270
Leu Glu Glu Lys Ile Met Tyr Ser His Leu Val Asp Tyr Phe Pro Glu
             275                 280                285
Tyr Asp Gly Pro Gln Arg Asp Ala Gln Ala Ala Arg Glu Phe Ile Leu
             290                 295                300
Lys Met Phe Val Asp Leu Asn Pro Asp Ser Asp Lys Ile Ile Tyr Ser
305                 310                 315                320
His Phe Thr Cys Ala Thr Asp Thr Glu Asn Ile Arg Phe Val Phe Ala
                 325                 330                335
Ala Val Lys Asp Thr Ile Leu Gln Leu Asn Leu Lys Asp Cys Gly Leu
             340                 345                350
Phe

<210> SEQ ID NO 18
<211> LENGTH: 22
<212> TYPE: DNA
<213> ORGANISM: Artificial Sequence
<220> FEATURE:
<223> OTHER INFORMATION: primer

<400> SEQUENCE: 18
tgccatcaac cgttactgct ac                                            22
```

```
<210> SEQ ID NO 19
<211> LENGTH: 20
<212> TYPE: DNA
<213> ORGANISM: Artificial Sequence
<220> FEATURE:
<223> OTHER INFORMATION: primer

<400> SEQUENCE: 19
ggggatcttg cctgccattt                                              20

<210> SEQ ID NO 20
<211> LENGTH: 21
<212> TYPE: DNA
<213> ORGANISM: Artificial Sequence
<220> FEATURE:
<223> OTHER INFORMATION: primer

<400> SEQUENCE: 20
gctcgtgcct gtgtcgctgt g                                            21

<210> SEQ ID NO 21
<211> LENGTH: 21
<212> TYPE: DNA
<213> ORGANISM: Artificial Sequence
<220> FEATURE:
<223> OTHER INFORMATION: primer

<400> SEQUENCE: 21
caaggcaatg ggaggctgag a                                            21

<210> SEQ ID NO 22
<211> LENGTH: 22
<212> TYPE: DNA
<213> ORGANISM: Artificial Sequence
<220> FEATURE:
<223> OTHER INFORMATION: primer

<400> SEQUENCE: 22
cattcggctg cattggctgt aa                                           22

<210> SEQ ID NO 23
<211> LENGTH: 22
<212> TYPE: DNA
<213> ORGANISM: Artificial Sequence
<220> FEATURE:
<223> OTHER INFORMATION: primer

<400> SEQUENCE: 23
actccgttcc tgtggcgact tc                                           22

<210> SEQ ID NO 24
<211> LENGTH: 24
<212> TYPE: DNA
<213> ORGANISM: Artificial Sequence
<220> FEATURE:
<223> OTHER INFORMATION: primer

<400> SEQUENCE: 24
gcaggctggg ctcatcttag gtat                                         24

<210> SEQ ID NO 25
<211> LENGTH: 24
<212> TYPE: DNA
<213> ORGANISM: Artificial Sequence
<220> FEATURE:
<223> OTHER INFORMATION: primer
```

```
<400> SEQUENCE: 25
tctgggattt tgggcttgat gtgt                                              24

<210> SEQ ID NO 26
<211> LENGTH: 19
<212> TYPE: DNA
<213> ORGANISM: Artificial Sequence
<220> FEATURE:
<223> OTHER INFORMATION: primer

<400> SEQUENCE: 26
gggcgcccgg ttcttttg                                                     19

<210> SEQ ID NO 27
<211> LENGTH: 21
<212> TYPE: DNA
<213> ORGANISM: Artificial Sequence
<220> FEATURE:
<223> OTHER INFORMATION: primer

<400> SEQUENCE: 27
acacccagcc ggccacagtc g                                                 21
```

METHODS OF IDENTIFYING CANDIDATE COMPOUNDS OF THE HUMAN G PROTEIN-COUPLED RECEPTOR, GPR50, AS MODULATORS OF BODY MASS OR ADIPOSITY

FIELD OF THE INVENTION

The present invention relates to methods of using a G protein-coupled receptor (GPCR) to screen one or more candidate compounds as a modulator of body mass or of adiposity or of percentage body fat in a subject or as a pharmaceutical agent for obesity and conditions related thereto. Inverse agonists and antagonists of the invention are useful as therapeutic agents for the prevention or treatment of obesity and conditions related thereto, including hypertension, insulin resistance, metabolic syndrome, Type 2 diabetes, dyslipidemia, atherosclerosis, coronary heart disease, and stroke. Agonists and partial agonists of the invention are useful as therapeutic agents for the prevention or treatment of disorders ameliorated by increasing body mass including, but not limited to, cachexia.

BACKGROUND OF THE INVENTION

The following discussion is intended to facilitate the understanding of the invention, but is not intended nor admitted to be prior art to the invention.

A. Obesity

Obesity, which is defined as increased mass of adipose tissue, confers a higher risk of cardiovascular and metabolic disorders such as Type 2 diabetes, hyperlipidemia, and coronary heart disease and an associated morbidity and mortality. Metabolic syndrome, a multiplex risk factor for cardiovascular disease, is defined on the basis of five criteria including one related to obesity [Grundy et al, Circulation (2004) 109: 433-438].

Obesity is now a major healthcare issue in the Western World and increasingly in some third world countries. The increase in numbers of obese people is due largely to the increasing preference for high fat content foods but also, and this can be a more important factor, the decrease in activity in most people's lives. In the last 10 years there has been a 30% increase in the incidence of obesity in the USA and that about 30% of the population of the USA is now considered obese. Whether someone is classified as overweight or obese is generally determined on the basis of their body mass index (BMI) which is calculated by dividing body weight (kg) by height squared (m$^2$). Thus, the units of BMI are kg/m$^2$ and it is possible to calculate the BMI range associated with minimum mortality in each decade of life. Overweight is defined as a BMI in the range 25.0-29.9 kg/m$^2$, and obesity as a BMI of 30 kg/m$^2$ or greater (see Table A below).

TABLE A

CLASSIFICATION OF WEIGHT BY BODY MASS INDEX (BMI)

| BMI | CLASSIFICATION |
|---|---|
| <18.5 | Underweight |
| 18.5-24.9 | Normal |
| 25.0-29.9 | Overweight |
| 30.0-34.9 | Obesity (Class I) |
| 35.0-39.9 | Obesity (Class II) |
| >40 | Extreme Obesity (Class III) |

As the BMI increases there is an increased risk of death from a variety of causes that is independent of other risk factors. The most common diseases with obesity are cardiovascular disease (particularly hypertension), diabetes (obesity aggravates the development of diabetes), gallbladder disease, cancer and diseases of reproduction. Research has shown that even a modest reduction in body weight can correspond to a significant reduction in the risk of developing coronary heart disease.

There are problems however with the BMI definition in that it does not take into account the proportion of body mass that is muscle in relation to fat (adipose tissue). To account for this, obesity can also be defined on the basis of body fat content: greater than 25% in males and greater than 30% in females.

Obesity considerably increases the risk of developing cardiovascular diseases as well. Coronary insufficiency, atheromatous disease, and cardiac insufficiency are at the forefront of the cardiovascular complication induced by obesity. It is estimated that if the entire population had an ideal weight, the risk of coronary insufficiency would decrease by 25% and the risk of cardiac insufficiency and of cerebral vascular accidents by 35%. The incidence of coronary diseases is doubled in subjects less than 50 years of age who are 30% overweight. The diabetes patient faces a 30% reduced lifespan. After age 45, people with diabetes are about three times more likely than people without diabetes to have significant heart disease and up to five times more likely to have a stroke. These findings emphasize the inter-relations between risks factors for Type 2 diabetes and coronary heart disease and the potential value of an integrated approach to the prevention of these conditions based on the prevention of obesity [Perry, et al, BMJ (1995) 310:560-564].

Diabetes has also been implicated in the development of kidney disease, eye diseases and nervous-system problems. Kidney disease, also called nephropathy, occurs when the kidney's "filter mechanism" is damaged and protein leaks into urine in excessive amounts and eventually the kidney fails. Diabetes is also a leading cause of damage to the retina at the back of the eye and increases risk of cataracts and glaucoma. Finally, diabetes is associated with nerve damage, especially in the legs and feet, which interferes with the ability to sense pain and contributes to serious infections. Taken together, diabetes complications are one of the nation's leading causes of death.

The first line of treatment is to offer diet and life style advice to patients such as reducing the fat content of their diet and increasing their physical activity. However many patients find this difficult and need additional help from drug therapy to maintain results from these efforts.

Most currently marketed products have been unsuccessful as treatments for obesity owing to a lack of efficacy or unacceptable side-effect profiles. The most successful drug so far was the indirectly acting 5-hydroxytryptamine (5-HT) agonist d-fenfluramine (Redux™) but reports of cardiac valve defects in up to one third of patients led to its withdrawal by the FDA in 1998.

In addition, two drugs have recently been launched in the USA and Europe: Orlistat (Xenical™), a drug that prevents absorption of fat by the inhibition of pancreatic lipase, and Sibutramine (Reductil™), a 5-HT/noradrenaline re-uptake inhibitor. However, side effects associated with these products may limit their long-term utility. Treatment with Xenical™ is reported to induce gastrointestinal distress in some patients, while Sibutramine has been associated with raised blood pressure in some patients.

There is an unmet medical need for agents that safely decrease body weight. The present invention is directed to this, as well as other, important end.

B. GPR50

GPR50 is an orphan GPCR closely related to the G protein-coupled melatonin receptor family. The gene for GPR50 is situated on the X chromosome. Expression of GPR50 is reported to be restricted to hypothalamus and pituitary [Reppert et at, FEBS Letters (1996) 386:219-224]. The coding region for GPR50 spans two exons. Several amino acid polymorphisms of human GPR50 have been described; by reference to GenBank® Accession No. AAI03697, these include the substitutions Thr532Ala, Val606Ile, and the deletion Δ502-505 of four amino acids (Thr.Thr.Gly.His).

C. G Protein-Coupled Receptors

Although a number of receptor classes exist in humans, by far the most abundant and therapeutically relevant is represented by the G protein-coupled receptor (GPCR) class. It is estimated that there are some 30,000-40,000 genes within the human genome, and of these, approximately 2% are estimated to code for GPCRs.

GPCRs represent an important area for the development of pharmaceutical products: from approximately 20 of the 100 known GPCRs, approximately 60% of all prescription pharmaceuticals have been developed. For example, in 1999, of the top 100 brand name prescription drugs, the following drugs interact with GPCRs (the primary diseases and/or disorders treated related to the drug is indicated in parentheses):

Claritin ® (allergies)
Paxil ® (depression)
Cozaar ® (hypertension)
Propulsid ® (reflux disease)
Pepcid ® (reflux)
Effexor ® (depression)
Allegra ® (allergies)
Diprivan ® (anesthesia)
Hytrin ® (hypertension)
Plavix ® (MI/stroke)
Xalatan ® (glaucoma)
Harnal ® (prostatic hyperplasia)
(Med Ad News 1999 Data).
Prozac ® (depression)
Zoloft ® (depression)
Imitrex ® (migraine)
Risperdal ® (schizophrenia)
Gaster ® (ulcers)
Depakote ® (epilepsy)
Lupron ® (prostate cancer)
BuSpar ® (anxiety)
Wellbutrin ® (depression)
Toprol-XL ® (hypertension)
Singulair ® (asthma)
Vasotec ® (hypertension)
Zyprexa ® (psychotic disorder)
Zantac ® (reflux)
Serevent ® (asthma)
Atrovent ® (bronchospasm)
Cardura ® (prostatic hypertrophy)
Zoladex ® (prostate cancer)
Ventolin ® (bronchospasm)
Zyrtec ® (rhinitis)
Tenormin ® (angina)
Diovan ® (hypertension)

GPCRs share a common structural motif, having seven sequences of between 22 to 24 hydrophobic amino acids that form seven alpha helices, each of which spans the membrane (each span is identified by number, i.e., transmembrane-1 (TM-1), transmembrane-2 (TM-2), etc.). The transmembrane helices are joined by strands of amino acids between transmembrane-2 and transmembrane-3, transmembrane-4 and transmembrane-5, and transmembrane-6 and transmembrane-7 on the exterior, or "extracellular" side, of the cell membrane (these are referred to as "extracellular" regions 1, 2 and 3 (EC-1, EC-2 and EC-3), respectively). The transmembrane helices are also joined by strands of amino acids between transmembrane-1 and transmembrane-2, transmembrane-3 and transmembrane-4, and transmembrane-5 and transmembrane-6 on the interior, or "intracellular" side, of the cell membrane (these are referred to as "intracellular" regions 1, 2 and 3 (IC-1, IC-2 and IC-3), respectively). The "carboxy" ("C") terminus of the receptor lies in the intracellular space within the cell, and the "amino" ("N") terminus of the receptor lies in the extracellular space outside of the cell.

Generally, when a ligand binds with the receptor (often referred to as "activation" of the receptor), there is a change in the conformation of the receptor that facilitates coupling between the intracellular region and an intracellular "G-protein." It has been reported that GPCRs are "promiscuous" with respect to G proteins, i.e., that a GPCR can interact with more than one G protein. See, Kenakin, Life Sciences (1988) 43:1095-1101. Although other G proteins exist, currently, Gq, Gs, Gi, Gz and Go are G proteins that have been identified. Ligand-activated GPCR coupling with the G-protein initiates a signaling cascade process (referred to as "signal transduction"). Under normal conditions, signal transduction ultimately results in cellular activation or cellular inhibition. Although not wishing to be bound to theory, it is thought that the IC-3 loop as well as the carboxy terminus of the receptor interact with the G protein.

Gs-coupled GPCRs elevate intracellular cAMP levels. GPCRs coupled to Gi, Go, or Gz lower intracellular cAMP levels. Gq-coupled GPCRs elevate intracellular $IP_3$ and $Ca^{2+}$ levels.

There are also promiscuous G proteins, which appear to couple several classes of GPCRs to the phospholipase C pathway, such as G15 or G16 [Offermanns & Simon, J Biol Chem (1995) 270:15175-80], or chimeric G proteins designed to couple a large number of different GPCRs to the same pathway, e.g. phospholipase C [Milligan & Rees, Trends in Pharmaceutical Sciences (1999) 20:118-24]. A GPCR coupled to the phospholipase C pathway elevates intracellular $IP_3$ and $Ca^{2+}$ levels.

Under physiological conditions, GPCRs exist in the cell membrane in equilibrium between two different conformations: an "inactive" state and an "active" state. A receptor in an inactive state is unable to link to the intracellular signaling transduction pathway to initiate signal transduction leading to a biological response. Changing the receptor conformation to the active state allows linkage to the transduction pathway (via the G-protein) and produces a biological response.

A receptor may be stabilized in an active state by a ligand or a compound such as a drug. Recent discoveries, including but not exclusively limited to modifications to the amino acid sequence of the receptor, provide means other than ligands or drugs to promote and stabilize the receptor in the active state conformation. These means effectively stabilize the receptor in an active state by simulating the effect of a ligand binding to the receptor. Stabilization by such ligand-independent means is termed "constitutive receptor activation."

SUMMARY OF THE INVENTION

Nucleotide sequence encoding human GPR50 polypeptide is given in SEQ ID NO: 1; the amino acid sequence of said encoded human GPR50 polypeptide is given in SEQ ID NO: 2. Nucleotide sequence encoding human GPR50 polypeptide comprising Δ502-505 is given in SEQ ID NO: 3; the amino acid sequence of said encoded human GPR50 polypeptide comprising Δ502-505 is given in SEQ ID NO: 4. Nucleotide sequence encoding mouse GPR50 polypeptide is given in SEQ ID NO: 5; the amino acid sequence of said encoded mouse GPR50 polypeptide is given in SEQ ID NO: 6. Nucleotide sequence encoding rat GPR50 polypeptide is given in SEQ ID NO: 7; the amino acid sequence of said encoded rat GPR50 polypeptide is given in SEQ ID NO: 8.

Applicants have shown that GPR50-deficient mice exhibit protection from body weight gain induced by a high-fat diet. The present invention features methods relating to GPR50 for identifying a candidate compound as a modulator of body mass or of adiposity or of percentage body fat in a subject or as a pharmaceutical agent for obesity and conditions related thereto. Inverse agonists and antagonists of the invention are useful as therapeutic agents for the prevention or treatment of obesity and conditions related thereto, including hypertension, insulin resistance, metabolic syndrome, Type 2 diabetes, dyslipidemia, atherosclerosis, coronary heart disease, and stroke.

In a first aspect, the invention features a method of identifying a candidate compound as a modulator of body mass in a subject, comprising the steps of
 (a) contacting the candidate compound with a GPCR comprising an amino acid sequence selected from the group consisting of
  (i) the amino acid sequence of SEQ ID NO: 2;
  (ii) amino acids 2-617 of SEQ ID NO: 2;
  (iii) amino acids 2-617 of SEQ ID NO: 2, wherein the GPCR does not comprise amino acids 1-617 of SEQ ID NO: 2;
  (iv) the amino acid sequence of (i), (ii) or wherein SEQ ID NO: 2 comprises any combination of a substitution of serine at amino acid position 493 of SEQ ID NO: 2 with asparagine, a substitution of threonine at amino acid position 532 of SEQ ID NO: 2 with alanine, and a substitution of valine at amino acid position 606 of SEQ ID NO: 2 with isoleucine;
  (v) the amino acid sequence of SEQ ID NO: 4;
  (vi) amino acids 2-613 of SEQ ID NO: 4;
  (vii) amino acids 2-613 of SEQ ID NO: 4, wherein the GPCR does not comprise amino acids 1-613 of SEQ ID NO: 4;
  (viii) the amino acid sequence of (v), (vi) or (vii), wherein SEQ ID NO: 4 comprises any combination of a substitution of asparagine at amino acid position 493 of SEQ ID NO: 4 with serine, a substitution of alanine at amino acid position 528 of SEQ ID NO: 4 with threonine, and a substitution of valine at amino acid position 602 of SEQ ID NO: 4 with isoleucine;
  (ix) the amino acid sequence of a G protein-coupled receptor encoded by a polynucleotide that is amplifiable by polymerase chain reaction (PCR) on a human DNA sample using specific primers SEQ ID NO: 9 and SEQ ID NO: 10;
  (x) the amino acid sequence of a G protein-coupled receptor encoded by a polynucleotide hybridizing at high stringency to the complement of SEQ ID NO: 1 or SEQ ID NO: 3;
  (xi) the amino acid sequence of a G protein-coupled receptor having at least about 75%, at least about 80%, at least about 85%, at least about 90% or at least about 95% identity to SEQ ID NO: 2 or SEQ ID NO: 4;
  (xii) the amino acid sequence of SEQ ID NO: 6;
  (xiii) amino acids 2-591 of SEQ ID NO: 6;
  (xiv) amino acids 2-591 of SEQ ID NO: 6 wherein the GPCR does not comprise amino acids 1-591 of SEQ ID NO: 6;
  (xv) the amino acid sequence of a G protein-coupled receptor encoded by a polynucleotide hybridizing at high stringency to the complement of SEQ ID NO: 5;
  (xvi) the amino acid sequence of a G protein-coupled receptor having at least about 75%, at least about 80%, at least about 85%, at least about 90% or at least about 95% identity to SEQ ID NO: 6;
  (xvii) the amino acid sequence of SEQ ID NO: 8;
  (xviii) amino acids 2-594 of SEQ ID NO: 8;
  (xix) amino acids 2-594 of SEQ ID NO: 8, wherein the GPCR does not comprise amino acids 1-594 of SEQ ID NO: 8;
  (xx) the amino acid sequence of a G protein-coupled receptor encoded by a polynucleotide hybridizing at high stringency to the complement of SEQ ID NO: 7;
  (xxi) the amino acid sequence of a G protein-coupled receptor having at least about 75%, at least about 80%, at least about 85%, at least about 90% or at least about 95% identity to SEQ ID NO: 8; and
  (xxii) the amino acid sequence of a G protein-coupled receptor that is a constitutively active version of a receptor having SEQ ID NO: 2 or SEQ ID NO: 4;
  or a variant or biologically active fragment thereof;
 wherein the receptor couples to a G protein; and
 (b) determining the ability of the compound to inhibit or stimulate functionality of the GPCR;
wherein the ability of the compound to inhibit or stimulate functionality of the GPCR is indicative of the compound being a modulator of body mass in the subject.

In some embodiments, the GPCR comprises the amino acid sequence of SEQ ID NO: 2 or SEQ ID NO: 4.

In some embodiments, the GPCR comprises the amino acid sequence of a G protein-coupled receptor having at least about 75%, at least about 80%, at least about 85%, at least about 90% or at least about 95% identity to SEQ ID NO: 2 or SEQ ID NO: 4.

In some embodiments, the body mass comprises weight gain induced by a high fat diet.

In some embodiments, the subject is a mammal. In some embodiments, the mammal is a human.

The invention also features a method of identifying a candidate compound as a modulator of adiposity in a subject, comprising the steps of
 (a) contacting the candidate compound with a GPCR comprising an amino acid sequence selected from the group consisting of:
  (i) the amino acid sequence of SEQ ID NO: 2;
  (ii) amino acids 2-617 of SEQ ID NO: 2;
  (iii) amino acids 2-617 of SEQ ID NO: 2, wherein the GPCR does not comprise amino acids 1-617 of SEQ ID NO: 2;
  (iv) the amino acid sequence of (i), (ii) or (iii), wherein SEQ ID NO: 2 comprises any combination of a substitution of serine at amino acid position 493 of SEQ ID NO: 2 with asparagine, a substitution of threonine at amino acid position 532 of SEQ ID NO: 2 with alanine, and a substitution of valine at amino acid position 606 of SEQ ID NO: 2 with isoleucine;
  (v) the amino acid sequence of SEQ ID NO: 4;
  (vi) amino acids 2-613 of SEQ ID NO: 4;
  (vii) amino acids 2-613 of SEQ ID NO: 4, wherein the GPCR does not comprise amino acids 1-613 of SEQ ID NO: 4;

(viii) the amino acid sequence of (v), (vi) or (vii), wherein SEQ ID NO: 4 comprises any combination of a substitution of asparagine at amino acid position 493 of SEQ ID NO: 4 with serine, a substitution of alanine at amino acid position 528 of SEQ ID NO: 4 with threonine, and a substitution of valine at amino acid position 602 of SEQ ID NO: 4 with isoleucine;
(ix) the amino acid sequence of a G protein-coupled receptor encoded by a polynucleotide that is amplifiable by polymerase chain reaction (PCR) on a human DNA sample using specific primers SEQ ID NO: 9 and SEQ ID NO: 10;
(x) the amino acid sequence of a G protein-coupled receptor encoded by a polynucleotide hybridizing at high stringency to the complement of SEQ ID NO: 1 or SEQ ID NO: 3;
(xi) the amino acid sequence of a G protein-coupled receptor having at least about 75%, at least about 80%, at least about 85%, at least about 90% or at least about 95% identity to SEQ ID NO: 2 or SEQ ID NO: 4;
(xii) the amino acid sequence of SEQ ID NO: 6;
(xiii) amino acids 2-591 of SEQ ID NO: 6;
(xiv) amino acids 2-591 of SEQ ID NO: 6 wherein the GPCR does not comprise amino acids 1-591 of SEQ ID NO: 6;
(xv) the amino acid sequence of a G protein-coupled receptor encoded by a polynucleotide hybridizing at high stringency to the complement of SEQ ID NO: 5;
(xvi) the amino acid sequence of a G protein-coupled receptor having at least about 75%, at least about 80%, at least about 85%, at least about 90% or at least about 95% identity to SEQ ID NO: 6;
(xvii) the amino acid sequence of SEQ ID NO: 8;
(xviii) amino acids 2-594 of SEQ ID NO: 8;
(xix) amino acids 2-594 of SEQ ID NO: 8, wherein the GPCR does not comprise amino acids 1-594 of SEQ ID NO: 8;
(xx) the amino acid sequence of a G protein-coupled receptor encoded by a polynucleotide hybridizing at high stringency to the complement of SEQ ID NO: 7;
(xxi) the amino acid sequence of a G protein-coupled receptor having at least about 75%, at least about 80%, at least about 85%, at least about 90% or at least about 95% identity to SEQ ID NO: 8; and
(xxii) the amino acid sequence of a G protein-coupled receptor that is a constitutively active version of a receptor having SEQ ID NO: 2 or SEQ ID NO: 4;
or a variant or biologically active fragment thereof; wherein the receptor couples to a G protein; and
(b) determining the ability of the compound to inhibit or stimulate functionality of the GPCR;
wherein the ability of the compound to inhibit or stimulate functionality of the GPCR is indicative of the compound being a modulator of adiposity in the subject.

In some embodiments, the GPCR comprises the amino acid sequence of SEQ ID NO: 2 or SEQ ID NO: 4.

In some embodiments, the GPCR comprises the amino acid sequence of a G protein-coupled receptor having at least about 75%, at least about 80%, at least about 85%, at least about 90% or at least about 95% identity to SEQ ID NO: 2 or SEQ ID NO: 4.

In some embodiments, the adiposity comprises increased adiposity induced by a high fat diet.

In some embodiments, the subject is a mammal. In some embodiments, the mammal is a human.

The invention also features a method of identifying a candidate compound as a modulator of percentage body fat in a subject, comprising the steps of:
(a) contacting the candidate compound with a GPCR comprising an amino acid sequence selected from the group consisting of:
(i) the amino acid sequence of SEQ ID NO: 2;
(ii) amino acids 2-617 of SEQ ID NO: 2;
(iii) amino acids 2-617 of SEQ ID NO: 2, wherein the GPCR does not comprise amino acids 1-617 of SEQ ID NO: 2;
(iv) the amino acid sequence of (i), (ii) or (iii), wherein SEQ ID NO: 2 comprises any combination of a substitution of serine at amino acid position 493 of SEQ ID NO: 2 with asparagine, a substitution of threonine at amino acid position 532 of SEQ ID NO: 2 with alanine, and a substitution of valine at amino acid position 606 of SEQ ID NO: 2 with isoleucine;
(v) the amino acid sequence of SEQ ID NO: 4;
(vi) amino acids 2-613 of SEQ ID NO: 4;
(vii) amino acids 2-613 of SEQ ID NO: 4, wherein the GPCR does not comprise amino acids 1-613 of SEQ ID NO: 4;
(viii) the amino acid sequence of (v), (vi) or (vii), wherein SEQ ID NO: 4 comprises any combination of a substitution of asparagine at amino acid position 493 of SEQ ID NO: 4 with serine, a substitution of alanine at amino acid position 528 of SEQ ID NO: 4 with threonine, and a substitution of valine at amino acid position 602 of SEQ ID NO: 4 with isoleucine;
(ix) the amino acid sequence of a G protein-coupled receptor encoded by a polynucleotide that is amplifiable by polymerase chain reaction (PCR) on a human DNA sample using specific primers SEQ ID NO: 9 and SEQ ID NO: 10;
(x) the amino acid sequence of a G protein-coupled receptor encoded by a polynucleotide hybridizing at high stringency to the complement of SEQ ID NO: 1 or SEQ ID NO: 3;
(xi) the amino acid sequence of a G protein-coupled receptor having at least about 75%, at least about 80%, at least about 85%, at least about 90% or at least about 95% identity to SEQ ID NO: 2 or SEQ ID NO: 4;
(xii) the amino acid sequence of SEQ ID NO: 6;
(xiii) amino acids 2-591 of SEQ ID NO: 6;
(xiv) amino acids 2-591 of SEQ ID NO: 6 wherein the GPCR does not comprise amino acids 1-591 of SEQ ID NO: 6;
(xv) the amino acid sequence of a G protein-coupled receptor encoded by a polynucleotide hybridizing at high stringency to the complement of SEQ ID NO: 5;
(xvi) the amino acid sequence of a G protein-coupled receptor having at least about 75%, at least about 80%, at least about 85%, at least about 90% or at least about 95% identity to SEQ ID NO: 6;
(xvii) the amino acid sequence of SEQ ID NO: 8;
(xviii) amino acids 2-594 of SEQ ID NO: 8;
(xix) amino acids 2-594 of SEQ ID NO: 8, wherein the GPCR does not comprise amino acids 1-594 of SEQ ID NO: 8;
(xx) the amino acid sequence of a G protein-coupled receptor encoded by a polynucleotide hybridizing at high stringency to the complement of SEQ ID NO: 7;
(xxi) the amino acid sequence of a G protein-coupled receptor having at least about 75%, at least about 80%, at least about 85%, at least about 90% or at least about 95% identity to SEQ ID NO: 8; and
(xxii) the amino acid sequence of a G protein-coupled receptor that is a constitutively active version of a receptor having SEQ ID NO: 2 or SEQ ID NO: 4;
or a variant or biologically active fragment thereof;
wherein the receptor couples to a G protein; and
(b) determining the ability of the compound to inhibit or stimulate functionality of the GPCR;
wherein the ability of the compound to inhibit or stimulate functionality of the GPCR is indicative of the compound being a modulator of percentage body fat in the subject.

In some embodiments, the GPCR comprises the amino acid sequence of SEQ ID NO: 2 or SEQ ID NO: 4.

In some embodiments, the GPCR comprises the amino acid sequence of a G protein-coupled receptor having at least about 75%, at least about 80%, at least about 85%, at least about 90% or at least about 95% identity to SEQ ID NO: 2 or SEQ ID NO: 4.

In some embodiments, percentage body fat comprises increased percentage body fat induced by a high fat diet.

In some embodiments, the subject is a mammal. In some embodiments, the mammal is a human.

The invention also features a method of identifying a candidate compound as a pharmaceutical agent for obesity or a condition related thereto, comprising the steps of
(a') contacting the candidate compound with a GPCR comprising an amino acid sequence selected from the group consisting of:
(i) the amino acid sequence of SEQ ID NO: 2;
(ii) amino acids 2-617 of SEQ ID NO: 2;
(iii) amino acids 2-617 of SEQ ID NO: 2, wherein the GPCR does not comprise amino acids 1-617 of SEQ ID NO: 2;
(iv) the amino acid sequence of (i), (ii) or wherein SEQ ID NO: 2 comprises any combination of a substitution of serine at amino acid position 493 of SEQ ID NO: 2 with asparagine, a substitution of threonine at amino acid position 532 of SEQ ID NO: 2 with alanine, and a substitution of valine at amino acid position 606 of SEQ ID NO: 2 with isoleucine;
(v) the amino acid sequence of SEQ ID NO: 4;
(vi) amino acids 2-613 of SEQ ID NO: 4;
(vii) amino acids 2-613 of SEQ ID NO: 4, wherein the GPCR does not comprise amino acids 1-613 of SEQ ID NO: 4;
(viii) the amino acid sequence of (v), (vi) or (vii), wherein SEQ ID NO: 4 comprises any combination of a substitution of asparagine at amino acid position 493 of SEQ ID NO: 4 with serine, a substitution of alanine at amino acid position 528 of SEQ ID NO: 4 with threonine, and a substitution of valine at amino acid position 602 of SEQ ID NO: 4 with isoleucine;
(ix) the amino acid sequence of a G protein-coupled receptor encoded by a polynucleotide that is amplifiable by polymerase chain reaction (PCR) on a human DNA sample using specific primers SEQ ID NO: 9 and SEQ ID NO: 10;
(x) the amino acid sequence of a G protein-coupled receptor encoded by a polynucleotide hybridizing at high stringency to the complement of SEQ ID NO: 1 or SEQ ID NO: 3;
(xi) the amino acid sequence of a G protein-coupled receptor having at least about 75%, at least about 80%, at least about 85%, at least about 90% or at least about 95% identity to SEQ ID NO: 2 or SEQ ID NO: 4;
(xii) the amino acid sequence of SEQ ID NO: 6;
(xiii) amino acids 2-591 of SEQ ID NO: 6;
(xiv) amino acids 2-591 of SEQ ID NO: 6 wherein the GPCR does not comprise amino acids 1-591 of SEQ ID NO: 6;
(xv) the amino acid sequence of a G protein-coupled receptor encoded by a polynucleotide hybridizing at high stringency to the complement of SEQ ID NO: 5;
(xvi) the amino acid sequence of a G protein-coupled receptor having at least about 75%, at least about 80%, at least about 85%, at least about 90% or at least about 95% identity to SEQ ID NO: 6;
(xvii) the amino acid sequence of SEQ ID NO: 8;
(xviii) amino acids 2-594 of SEQ ID NO: 8;
(xix) amino acids 2-594 of SEQ ID NO: 8, wherein the GPCR does not comprise amino acids 1-594 of SEQ ID NO: 8;
(xx) the amino acid sequence of a G protein-coupled receptor encoded by a polynucleotide hybridizing at high stringency to the complement of SEQ ID NO: 7;
(xxi) the amino acid sequence of a G protein-coupled receptor having at least about 75%, at least about 80%, at least about 85%, at least about 90% or at least about 95% identity to SEQ ID NO: 8; and
(xxii) the amino acid sequence of a G protein-coupled receptor that is a constitutively active version of a receptor having SEQ ID NO: 2 or SEQ ID NO: 4;
or a variant or biologically active fragment thereof;
wherein the receptor couples to a G protein; and
(b') determining the ability of the compound to inhibit functionality of the GPCR; wherein the ability of the compound to inhibit functionality of the GPCR is indicative of the compound being a pharmaceutical agent for obesity or the condition related thereto.

The invention additionally features a method of identifying a candidate compound as a pharmaceutical agent for obesity or a condition related thereto, comprising steps (a') and (b') of this first aspect, and further comprising:
(c') optionally synthesizing a compound which inhibits functionality of the GPCR in step (b');
(d') administering a compound which inhibits functionality of the GPCR in step (b') to a mammal; and
(e') determining whether the compound confers protection from weight gain in the mammal;
wherein the ability of the candidate compound to confer protection from weight gain in the mammal is indicative of the candidate compound being a pharmaceutical agent for obesity or a condition related thereto.

In some embodiments, said protection from weight gain in the mammal comprises protection from weight gain in the mammal induced by a high fat diet.

In some embodiments, the candidate compound is shown to confer protection from weight gain in the mammal induced by a high fat diet.

In some embodiments, the pharmaceutical agent for obesity or a condition related thereto is a compound for preventing or treating obesity or a condition related thereto.

In some embodiments, the compound which inhibits functionality of the GPCR in step (b') is an inverse agonist or antagonist of the GPCR.

In some embodiments, the mammal is a non-human mammal. In some embodiments, the mammal is a laboratory animal. In some embodiments, the mammal is a non-human primate. In some embodiments, the mammal is a rodent. In some embodiments, the mammal is a rat. In some embodiments, the mammal is a mouse.

In some embodiments, the GPCR comprises the amino acid sequence of SEQ ID NO: 2 or SEQ ID NO: 4.

In some embodiments, the GPCR comprises the amino acid sequence of a G protein-coupled receptor having at least about 75%, at least about 80%, at least about 85%, at least about 90% or at least about 95% identity to SEQ ID NO: 2 or SEQ ID NO: 4.

In some embodiments, the G protein-coupled receptor having at least about 75%, at least about 80%, at least about 85%, at least about 90% or at least about 95% identity to SEQ ID NO: 2, SEQ ID NO: 4, SEQ ID NO: 6 or SEQ ID NO: 8 is an endogenous GPCR. In some embodiments, the G protein-coupled receptor having at least about 75%, at least about 80%, at least about 85%, at least about 90% or at least about 95% identity to SEQ ID NO: 2, SEQ ID NO: 4, SEQ ID NO: 6 or SEQ ID NO: 8 is a mammalian endogenous GPCR. In some embodiments, the G protein-coupled receptor having at least about 75%, at least about 80%, at least about 85%, at least about 90% or at least about 95% identity to SEQ ID NO: 2, SEQ ID NO: 4, SEQ ID NO: 6 or SEQ ID NO: 8 is a non-endogenous GPCR.

In some embodiments, the G protein-coupled receptor that is a constitutively active version of a receptor having SEQ ID NO: 2 or SEQ ID NO: 4 is an endogenous G protein-coupled receptor. In some embodiments, the G protein-coupled receptor that is a constitutively active version of a receptor having SEQ ID NO: 2 or SEQ ID NO: 4 is a non-endogenous G protein-coupled receptor.

In some embodiments, the obesity comprises weight gain induced by a high fat diet.

In some embodiments, the condition related to obesity is selected from the group consisting of hypertension, insulin resistance, metabolic syndrome, Type 2 diabetes, dyslipidemia, atherosclerosis, coronary heart disease, and stroke.

In some embodiments, the pharmaceutical agent for obesity or a condition related thereto is a compound for preventing or treating obesity or a condition related thereto.

In some embodiments, the compound that inhibits functionality of the GPCR is an inverse agonist or antagonist of the GPCR. In some embodiments, the compound that inhibits functionality of the GPCR is an inverse agonist of the GPCR. In some embodiments, the compound that inhibits functionality of the GPCR is an antagonist of the GPCR.

In some embodiments, the GPCR exhibits a detectable level of constitutive activity. In some embodiments, the constitutive activity is for lowering a level of intracellular cAMP. In some embodiments, the constitutive activity is for causing melanophore cells to undergo pigment aggregation.

In some embodiments, said contacting comprises contacting in the presence of a known agonist of the GPCR. In some embodiments, the known agonist of the GPCR is a known agonist of endogenous human GPR50. In some embodiments relating to said contacting comprising contacting in the presence of a known agonist of the GPCR, the candidate compound is contacted with the GPCR prior to the known agonist being contacted with the GPCR. In some embodiments relating to said contacting comprising contacting in the presence of a known agonist of the GPCR, the candidate compound is contacted with the GPCR for a period of up to several minutes prior to the known agonist being contacted with the GPCR. In some embodiments relating to said contacting comprising contacting in the presence of a known agonist of the GPCR, the candidate compound is contacted with the GPCR for a period of up to about 5 min, of up to about 10 min or of up to about 30 min prior to the known agonist being contacted with the GPCR.

In some embodiments, said contacting comprises contacting in the absence of a known ligand of the GPCR. In some embodiments, said contacting comprises contacting in the absence of a known ligand of endogenous human GPR50. In some embodiments, said contacting comprises contacting in the absence of a known agonist of the GPCR. In some embodiments, said contacting comprises contacting in the absence of a known agonist of endogenous human GPR50.

In some embodiments, PCR is RT-PCR.

In some embodiments, the human DNA is human cDNA derived from a tissue or cell type that expresses GPR50. In some embodiments, the human cDNA is derived from hypothalamus or pituitary.

In some embodiments, the G protein-coupled receptor encoded by a polynucleotide that is amplifiable by polymerase chain reaction (PCR) on a human DNA sample using specific primers SEQ ID NO: 9 and SEQ ID NO: 10 is an endogenous GPR50 G protein-coupled receptor.

In some embodiments, the subject is a mammal. In some embodiments, the subject is a mammal selected from the group consisting of mouse, rat and human. In some embodiments, the subject is a human.

In some embodiments, the subject is overweight or obese. In some embodiments, the subject is overweight. In some embodiments, the subject is obese.

In some embodiments, the ability of the compound to inhibit functionality of the GPCR is indicative of the compound being a compound that decreases body mass in the subject.

In some embodiments, the ability of the compound to inhibit functionality of the GPCR is indicative of the compound being a compound that decreases adiposity in the subject.

In some embodiments, the ability of the compound to inhibit functionality of the GPCR is indicative of the compound being a compound that decreases percentage body fat in the subject.

In some embodiments, the condition related to obesity is selected from the group consisting of hypertension, congestive cardiomyopathy, varicosities, pulmonary embolism, coronary heart disease, stroke, idiopathic intracranial hypertension, meralgia parethetica, dyspnea, obstructive sleep apnea, hypoventilation syndrome, Pickwickian syndrome, asthma, immobility, degenerative osteoarthritis, low back pain, striae distensae or "stretch marks," venous stasis of the lower extremities, lymphedema, cellulitis, intertrigo, carbuncles, acanthosis nigricans, skin tags, gastro-esophageal reflux disorder, nonalcoholic fatty liver/steatohepatitis, cholelithiasis, hernias, colon cancer, stress incontinence, obesity-related glomerulopathy, breast and uterine cancer, depression and low self-esteem, impaired quality of life, metabolic syndrome, insulin resistance, Type 2 diabetes, dyslipidemia, atherosclerosis, hyperandrogenemia in women, polycystic ovarian syndrome, dysmenorrhea, infertility, pregnancy complications, and male hypogonadism. In some embodiments, the condition related to obesity is selected from the group consisting of hypertension, insulin resistance, metabolic syndrome, Type 2 diabetes, dyslipidemia, atherosclerosis, coronary heart disease, and stroke.

In some embodiments, the GPCR is recombinant.

In some embodiments, the GPCR is endogenous. In some embodiments, the GPCR that is endogenous is a mammalian endogenous GPCR. In some embodiments, the GPCR that is a mammalian endogenous GPCR is a mammalian endogenous GPR50. In some embodiments, the GPCR is non-endogenous.

In some embodiments, the GPCR is a mammalian GPR50.

In some embodiments, the G protein-coupled receptor encoded by a polynucleotide hybridizing at high stringency to the complement of SEQ ID NO: 1, SEQ ID NO: 3, SEQ ID NO: 5 or SEQ ID NO: 7 is an endogenous GPCR. In some embodiments, the G protein-coupled receptor encoded by a polynucleotide hybridizing at high stringency to the complement of SEQ ID NO: 1, SEQ ID NO: 3, SEQ ID NO: 5 or SEQ ID NO: 7 that is an endogenous GPCR is a mammalian GPCR. In some embodiments, the G protein-coupled receptor encoded by a polynucleotide hybridizing at high stringency to the complement of SEQ ID NO: 1, SEQ ID NO: 3, SEQ ID NO: 5 or SEQ ID NO: 7 exhibits a detectable level of constitutive activity. In some embodiments, the constitutive activity is for lowering a level of intracellular cAMP. In some embodiments, the constitutive activity is for causing melanophore cells to undergo pigment aggregation. In certain embodiments, the G protein-coupled receptor encoded by a polynucleotide hybridizing at high stringency to the complement of SEQ ID NO: 1, SEQ ID NO: 3, SEQ ID NO: 5 or SEQ ID NO: 7 specifically binds an antibody that recognizes an mammalian endogenous GPR50 (an antibody that recognizes an endogenous mammalian GPR50 can be obtained commercially from, e.g., Advanced Targeting Systems, San Diego, Calif.; and CHEMICON International, Inc., Temecula, Calif.) or specifically binds a known ligand of an mammalian endogenous GPR50. In certain embodiments, the known ligand of the mammalian endogenous GPR50 is an endogenous ligand of the mammalian endogenous GPR50.

In some embodiments, the G protein-coupled receptor having at least about 75% identity, at least about 80%, at least about 85%, at least about 90% or at least about 95% identity to SEQ ID NO: 2 or SEQ ID NO: 4 is an endogenous G protein-coupled receptor. In some embodiments, the G protein-coupled receptor having at least about 75% identity, at least about 80%, at least about 85%, at least about 90% or at least about 95% identity to SEQ ID NO: 2 or SEQ ID NO: 4 is a non-endogenous G protein-coupled receptor. In some embodiments, the G protein-coupled receptor having at least about 75% identity, at least about 80%, at least about 85%, at least about 90% or at least about 95% identity to SEQ ID NO: 6 is an endogenous G protein-coupled receptor. In some embodiments, the G protein-coupled receptor having at least about 75% identity, at least about 80%, at least about 85%, at least about 90% or at least about 95% identity to SEQ ID NO: 6 is a non-endogenous G protein-coupled receptor. In some embodiments, the G protein-coupled receptor having at least about 75% identity, at least about 80%, at least about 85%, at least about 90% or at least about 95% identity to SEQ ID NO: 8 is an endogenous G protein-coupled receptor. In some embodiments, the G protein-coupled receptor having at least about 75% identity, at least about 80%, at least about 85%, at least about 90% or at least about 95% identity to SEQ ID NO: 8 is a non-endogenous G protein-coupled receptor.

In some embodiments, said contacting comprises contacting the candidate compound with a host cell or with membrane of a host cell that expresses the GPCR, wherein said host cell comprises an expression vector comprising a polynucleotide encoding the GPCR.

In some embodiments, the method comprises co-transfecting a host cell with the GPCR and with thyroid-stimulating hormone receptor (TSHR).

In some embodiments, said determining is carried out with membrane comprising the GPCR.

In some embodiments, the method comprises detecting a second messenger.

In some embodiments, said determining is by a process comprising the measurement of a level of a second messenger selected from the group consisting of cyclic AMP (cAMP), cyclic GMP (cGMP), inositol 1,4,5-triphosphate ($IP_3$), diacylglycerol (DAG), MAP kinase activity, MAPK/ERK kinase kinase-1 (MEKK1) activity, and $Ca^{2+}$. In some embodiments, said second messenger is cAMP. In some embodiments, the level of intracellular cAMP is increased.

In some embodiments, said determining is by a process comprising the use of a Melanophore assay. In some embodiments, the melanophore cells undergo pigment aggregation. In some embodiments, the candidate compound inhibits agonist induced pigment aggregation. In some embodiments, the candidate compound inhibits a level of constitutively induced pigment aggregation.

In some embodiments, said determining is by a process comprising the measurement of GTPγS binding to membrane comprising the GPCR. In some embodiments, GTPγS binding to membrane comprising the GPCR is decreased.

In some embodiments, the modulator of body mass or adiposity or percentage body fat in the subject is a modulator of the GPCR selected from the group consisting of agonist, partial agonist, inverse agonist and antagonist. In some embodiments, the modulator of body mass or adiposity or percentage body fat in the subject is an inverse agonist or antagonist of the GPCR. In some embodiments, the modulator of body mass or adiposity or percentage body fat in the subject is an inverse agonist of the GPCR. In some embodiments, the modulator of body mass or adiposity or percentage body fat in the subject is an antagonist of the GPCR. In some embodiments, the modulator of body mass or adiposity or percentage body fat in the subject is a modulator of a mammalian GPR50. In some embodiments, the modulator of body mass or adiposity or percentage body fat in the subject is a modulator of a human GPR50.

In some embodiments, the candidate compound is a small molecule.

In some embodiments, the candidate compound is a polypeptide. In some embodiments, the candidate compound is not an antibody or an antigen-binding fragment thereof. In some embodiments, the candidate compound is a polypeptide, provided that the polypeptide is not an antibody or an antigen-binding fragment thereof. In some embodiments, the candidate compound is an antibody or an antigen-binding fragment thereof. In some embodiments, the candidate compound is a lipid. In some embodiments, the candidate compound is not a polypeptide. In some embodiments, the candidate compound is not a lipid. In some embodiments, the candidate compound is non-endogenous. In some embodiments, the candidate compound is not endogenous. In some embodiments, the candidate compound is not material that a prokaryote or eukaryote naturally produces. In some embodiments, the candidate compound is not material that a prokaryote naturally produces. In some embodiments, the candidate compound is not material that a eukaryote naturally produces. In some embodiments, the candidate compound is not material that a mammal naturally produces. In some embodiments, the candidate compound is a compound not known to inhibit or stimulate functionality of the GPCR. In some embodiments, the candidate compound is a compound not known to be an agonist of the GPCR. In some embodiments, the candidate compound is a compound not known to be a partial agonist of the GPCR. In some embodiments, the candidate compound is a compound not known to be an inverse agonist of the GPCR. In some embodiments, the candidate compound is a compound not known to be an antagonist of the GPCR.

In some embodiments, the modulator of body mass or adiposity or percentage body fat in the subject is an agonist, partial agonist, inverse agonist or antagonist of the GPCR. In some embodiments, the modulator of body mass or adiposity or percentage body fat in the subject is an inverse agonist or antagonist of the GPCR.

In some embodiments, the pharmaceutical agent is an inverse agonist or antagonist of the GPCR.

In some embodiments, the method further comprises the step of comparing the modulation of the receptor caused by the candidate compound to a second modulation of the receptor caused by contacting the receptor with a known modulator of the receptor.

In some embodiments, said method further comprises the step of formulating the modulator or the pharmaceutical agent into a pharmaceutical composition. In some embodiments, the modulator or the pharmaceutical agent is an inverse agonist or an antagonist of the GPCR.

In some embodiments, said method further comprises synthesis of the modulator or the pharmaceutical agent. In some embodiments, the modulator or the pharmaceutical agent is an inverse agonist or an antagonist of the GPCR.

In some embodiments, said method further comprises: optionally, determining the structure of the modulator or the pharmaceutical agent; and providing the modulator or the pharmaceutical agent or the name or structure of the modulator or the pharmaceutical agent. In some embodiments, the modulator or the pharmaceutical agent is an inverse agonist or an antagonist of the GPCR.

In some embodiments, said method further comprises: optionally, determining the structure of the modulator or the pharmaceutical agent; optionally, providing the modulator or the pharmaceutical agent or the name or structure of the modulator or the pharmaceutical agent; and producing or synthesizing the modulator or the pharmaceutical agent. In some embodiments, the modulator or the pharmaceutical agent is an inverse agonist or an antagonist of the GPCR.

In some embodiments, the method comprises identifying an agonist of the GPCR. In some embodiments, the method further comprises formulating said agonist as a pharmaceutical. In some embodiments, the method comprises identifying a partial agonist of the GPCR. In some embodiments, the method further comprises formulating said partial agonist as a pharmaceutical. In some embodiments, the method comprises identifying an inverse agonist of the GPCR. In some embodiments, the method further comprises formulating said inverse agonist as a pharmaceutical. In some embodiments, the method comprises identifying an antagonist of the GPCR. In some embodiments, the method further comprises formulating said antagonist as a pharmaceutical.

In some embodiments, the baseline intracellular response (e.g., the response in the absence of a known agonist) is inhibited in the presence of the inverse agonist by at least about 10%, at least about 20%, at least about 30%, at least about 40%, at least about 50%, at least about 60%, at least about 70%, at least about 75%, at least about 80%, at least about 85%, at least about 90%, or at least about 95% as compared with the baseline response in the absence of the inverse agonist.

In some embodiments, the baseline intracellular response (e.g., the response in the presence of a known agonist) is inhibited in the presence of the antagonist by at least about 10%, at least about 20%, at least about 30%, at least about 40%, at least about 50%, at least about 60%, at least about 70%, at least about 75%, at least about 80%, at least about 85%, at least about 90%, or at least about 95% as compared with the baseline response in the absence of the antagonist.

In some embodiments, said contacting of the candidate compound with a GPCR comprises contacting the candidate compound with a eukaryotic host cell comprising the GPCR or with membrane thereof comprising the GPCR. In some embodiments, the eukaryotic host cell is a mammalian host cell. In some embodiments, the mammalian host cell is a CHO cell, a COS-7 cell, an MCB3901 cell, a 293 cell or a 293T cell. In some embodiments, the eukaryotic host cell is a melanophore host cell. In some embodiments, the eukaryotic host cell is a yeast host cell. In some embodiments, the eukaryotic host cell is a recombinant eukaryotic host cell.

In a second aspect, the invention features a modulator or a pharmaceutical agent identifiable according to a method of the first aspect.

In some embodiments, the modulator or the pharmaceutical agent is identified according to a method of the first aspect.

In some embodiments, the modulator or the pharmaceutical agent is an agonist, a partial agonist, an inverse agonist, or an antagonist of the GPCR. In some embodiments, the agonist, partial agonist, inverse agonist, or antagonist of the GPCR is an agonist, partial agonist, inverse agonist, or antagonist of a mammalian GPR50. In some embodiments, the mammalian GPR50 is a human GPR50.

In some embodiments, the modulator or the pharmaceutical agent is an inverse agonist or antagonist of the GPCR. In some embodiments, the modulator or the pharmaceutical agent is an inverse agonist of the GPCR. In some embodiments, the modulator or the pharmaceutical agent is an antagonist of the GPCR. In some embodiments, the inverse agonist or antagonist of the GPCR is an inverse agonist or antagonist of a mammalian GPR50. In some embodiments, the mammalian GPR50 is a human GPR50.

In some embodiments, the modulator or the pharmaceutical agent is a small molecule.

In some embodiments, the modulator or the pharmaceutical agent is a polypeptide. In some embodiments, the modulator or the pharmaceutical agent is not an antibody or an antigen-binding fragment thereof. In some embodiments, the modulator or the pharmaceutical agent is a polypeptide, provided that the polypeptide is not an antibody or an antigen-binding fragment thereof. In some embodiments, the modulator or the pharmaceutical agent is an antibody or an antigen-binding fragment thereof. In some embodiments, the modulator or the pharmaceutical agent is a lipid. In some embodiments, the modulator or the pharmaceutical agent is not a polypeptide. In some embodiments, the modulator or the pharmaceutical agent is not a lipid. In some embodiments, the modulator or the pharmaceutical agent is non-endogenous. In some embodiments, the modulator or the pharmaceutical agent is not endogenous. In some embodiments, the modulator or the pharmaceutical agent is not material that a prokaryote or eukaryote naturally produces. In some embodiments, the modulator or the pharmaceutical agent is not material that a prokaryote naturally produces. In some embodiments, the modulator or the pharmaceutical agent is not material that a eukaryote naturally produces. In some embodiments, the modulator or the pharmaceutical agent is not material that a mammal naturally produces.

In some embodiments, the modulator or the pharmaceutical agent is an inverse agonist or antagonist with an $IC_{50}$ of less than about 10 μM, of less than about 1 μM, of less than about 100 nM, or of less than about 10 nM at human, mouse or rat GPR50, preferably at human GPR50. In some embodiments, the modulator or the pharmaceutical agent is an inverse agonist or antagonist with an $IC_{50}$ of less than a value selected from the interval of about 10 nM to 10 μM. In some embodiments, the modulator or the pharmaceutical agent is an inverse agonist or antagonist with an $IC_{50}$ of less than a value selected from the interval of about 10 nM to 1 μM. In some embodiments, the modulator or the pharmaceutical agent is an inverse agonist or antagonist with an $IC_{50}$ of less than a value selected from the interval of about 10 nM to 100 nM. In some embodiments, the modulator or the pharmaceutical agent is an inverse agonist or antagonist with an $IC_{50}$ of less than about 10 µM, of less than about 1 µM, of less than about 100 nM, or of less than about 10 nM in GTPγS binding assay carried out with membrane from transfected CHO cells, or in pigment aggregation assay carried out in transfected melanophores, or in cAMP assay carried out in transfected 293 cells optionally co-transfected with TSHR, wherein the transfected CHO cells or the transfected melanophore cells or the transfected 293 cells express a recombinant GPR50 having an amino acid sequence selected from SEQ ID NO: 2, SEQ ID NO: 4, SEQ ID NO: 6 and SEQ ID NO: 8. In some embodiments, the recombinant GPR50 has the amino acid sequence of SEQ ID NO: 2. In some embodiments, the recombinant GPR50 has the amino acid sequence of SEQ ID NO: 4. In some embodiments, the modulator or the pharmaceutical agent is an inverse agonist or antagonist with an $IC_{50}$ of less than about 10 µM, of less than about 1 µM, of less than about 100 nM, or of less than about 10 nM in said assay. In some embodiments, the modulator or the pharmaceutical agent is an inverse agonist or antagonist with an $IC_{50}$ in said assay of less than a value selected from the interval of about 10 nM to 10 µM. In some embodiments, the modulator or the pharmaceutical agent is an inverse agonist or antagonist with an $IC_{50}$ in said assay of less than a value selected from the interval of about 10 nM to 1 µM. In some embodiments, the modulator or the pharmaceutical agent is an inverse agonist or antagonist with an $IC_{50}$ in said assay of less than a value selected from the interval of about 10 nM to 100 nM.

In some embodiments, the modulator or the pharmaceutical agent is orally active.

In a third aspect, the invention features a pharmaceutical composition comprising a modulator of a mammalian GPR50 and a pharmaceutically acceptable carrier.

In some embodiments, the modulator of the mammalian GPR50 is a modulator of a human GPR50. In some embodiments, the modulator of the human GPR50 is a modulator of human GPR50 having the amino acid sequence of SEQ ID NO: 2 or SEQ ID NO: 4. In some embodiments, the modulator of the human GPR50 is a modulator of human GPR50 having the amino acid sequence of SEQ ID NO: 2. In some embodiments, the modulator of the human GPR50 is a modulator of human GPR50 having the amino acid sequence of SEQ ID NO: 4.

In some embodiments, the modulator is according to the second aspect.

In some embodiments, the modulator of the mammalian GPR50 is an agonist, partial agonist, inverse agonist, or antagonist of the mammalian GPR50.

In some embodiments, the modulator of the mammalian GPR50 is an inverse agonist or antagonist. In some embodiments, the modulator of the mammalian GPR50 is an inverse agonist. In some embodiments, the modulator of the mammalian GPR50 is an antagonist.

In some embodiments, the modulator is a small molecule.

In some embodiments, the modulator is a polypeptide. In some embodiments, the modulator is not an antibody or an antigen-binding fragment thereof. In some embodiments, the modulator is a polypeptide, provided that the polypeptide is not an antibody or an antigen-binding fragment thereof. In some embodiments, the modulator is an antibody or an antigen-binding fragment thereof. In some embodiments, the modulator is a lipid. In some embodiments, the modulator is not a polypeptide. In some embodiments, the modulator is not a lipid. In some embodiments, the modulator is non-endogenous. In some embodiments, the modulator is not endogenous. In some embodiments, the modulator is not material that a prokaryote or eukaryote naturally produces. In some embodiments, the modulator is not material that a prokaryote naturally produces. In some embodiments, the modulator is not material that a eukaryote naturally produces. In some embodiments, the modulator is not material that a mammal naturally produces.

In some embodiments, the modulator is an inverse agonist or antagonist with an $IC_{50}$ of less than about 10 µM, of less than about 1 µM, of less than about 100 nM, or of less than about 10 nM at human, mouse or rat GPR50, preferably at human GPR50. In some embodiments, the modulator is an inverse agonist or antagonist with an $IC_{50}$ of less than a value selected from the interval of about 10 nM to 10 µM. In some embodiments, the modulator is an inverse agonist or antagonist with an $IC_{50}$ of less than a value selected from the interval of about 10 nM to 1 µM. In some embodiments, the modulator is an inverse agonist or antagonist with an $IC_{50}$ of less than a value selected from the interval of about 10 nM to 100 nM. In some embodiments, the modulator is an inverse agonist or antagonist with an $IC_{50}$ of less than about 10 µM, of less than about 1 µM, of less than about 100 nM, or of less than about 10 nM in GTPγS binding assay carried out with membrane from transfected CHO cells, or in pigment aggregation assay carried out in transfected melanophores, or in cAMP assay carried out in transfected 293 cells optionally co-transfected with TSHR, wherein the transfected CHO cells or the transfected melanophore cells or the transfected 293 cells express a recombinant GPR50 having an amino acid sequence selected from SEQ ID NO: 2, SEQ ID NO: 4, SEQ ID NO: 6 and SEQ ID NO: 8. In some embodiments, the recombinant GPR50 has the amino acid sequence of SEQ ID NO: 2. In some embodiments, the recombinant GPR50 has the amino acid sequence of SEQ ID NO: 4. In some embodiments, the modulator is an inverse agonist or antagonist with an $IC_{50}$ of less than about 10 µM, of less than about 1 µM, of less than about 100 nM, or of less than about 10 nM in said assay. In some embodiments, the modulator is an inverse agonist or antagonist with an $IC_{50}$ in said assay of less than a value selected from the interval of about 10 nM to 10 µM. In some embodiments, the modulator is an inverse agonist or antagonist with an $IC_{50}$ in said assay of less than a value selected from the interval of about 10 nM to 1 µM. In some embodiments, the modulator is an inverse agonist or antagonist with an $IC_{50}$ in said assay of less than a value selected from the interval of about 10 nM to 100 nM.

In some embodiments, the modulator is orally active.

In a fourth aspect, the invention features a method of preparing a pharmaceutical composition comprising admixing a modulator of a mammalian GPR50 and a pharmaceutically acceptable carrier.

In some embodiments, the modulator is according to the second aspect.

In some embodiments, the modulator of the mammalian GPR50 is a modulator of a human GPR50. In some embodiments, the modulator of the human GPR50 is a modulator of human GPR50 having the amino acid sequence of SEQ ID NO: 2 or SEQ ID NO: 4. In some embodiments, the modulator of the human GPR50 is a modulator of human GPR50 having the amino acid sequence of SEQ ID NO: 2. In some embodiments, the modulator of the human GPR50 is a modulator of human GPR50 having the amino acid sequence of SEQ ID NO: 4.

In some embodiments, the modulator of the mammalian GPR50 is an agonist, partial agonist, inverse agonist, or antagonist of the mammalian GPR50.

In some embodiments, the modulator of the mammalian GPR50 is an inverse agonist or antagonist. In some embodiments, the modulator of the mammalian GPR50 is an inverse agonist. In some embodiments, the modulator of the mammalian GPR50 is an antagonist.

In some embodiments, the modulator is a small molecule.

In some embodiments, the modulator is a polypeptide. In some embodiments, the modulator is not an antibody or an antigen-binding fragment thereof. In some embodiments, the modulator is a polypeptide, provided that the polypeptide is not an antibody or an antigen-binding fragment thereof. In some embodiments, the modulator is an antibody or an antigen-binding fragment thereof. In some embodiments, the modulator is a lipid. In some embodiments, the modulator is not a polypeptide. In some embodiments, the modulator is not a lipid. In some embodiments, the modulator is non-endogenous. In some embodiments, the modulator is not endogenous. In some embodiments, the modulator is not material that a prokaryote or eukaryote naturally produces. In some embodiments, the modulator is not material that a prokaryote naturally produces. In some embodiments, the modulator is not material that a eukaryote naturally produces. In some embodiments, the modulator is not material that a mammal naturally produces.

In some embodiments, the modulator is an inverse agonist or antagonist with an $IC_{50}$ of less than about 10 µM, of less than about 1 µM, of less than about 100 nM, or of less than about 10 nM at human, mouse or rat GPR50, preferably at human GPR50. In some embodiments, the modulator is an inverse agonist or antagonist with an $IC_{50}$ of less than a value selected from the interval of about 10 nM to 10 µM. In some embodiments, the modulator is an inverse agonist or antagonist with an $IC_{50}$ of less than a value selected from the interval of about 10 nM to 1 µM. In some embodiments, the modulator is an inverse agonist or antagonist with an $IC_{50}$ of less than a value selected from the interval of about 10 nM to 100 nM. In some embodiments, the modulator is an inverse agonist or antagonist with an $IC_{50}$ of less than about 10 of less than about 1 µM, of less than about 100 nM, or of less than about 10 nM in GTPγS binding assay carried out with membrane from transfected CHO cells, or in pigment aggregation assay carried out in transfected melanophores, or in cAMP assay carried out in transfected 293 cells optionally co-transfected with TSHR, wherein the transfected CHO cells or the transfected melanophore cells or the transfected 293 cells express a recombinant GPR50 having an amino acid sequence selected from SEQ ID NO: 2, SEQ ID NO: 4, SEQ ID NO: 6 and SEQ ID NO: 8. In some embodiments, the recombinant GPR50 has the amino acid sequence of SEQ ID NO: 2. In some embodiments, the recombinant GPR50 has the amino acid sequence of SEQ ID NO: 4. In some embodiments, the modulator is an inverse agonist or antagonist with an $IC_{50}$ of less than about 10 µM, of less than about 1 µM, of less than about 100 nM, or of less than about 10 nM in said assay. In some embodiments, the modulator is an inverse agonist or antagonist with an $IC_{50}$ in said assay of less than a value selected from the interval of about 10 nM to 10 µM. In some embodiments, the modulator is an inverse agonist or antagonist with an $IC_{50}$ in said assay of less than a value selected from the interval of about 10 nM to 10 µM. In some embodiments, the modulator is an inverse agonist or antagonist with an $IC_{50}$ in said assay of less than a value selected from the interval of about 10 nM to 100 nM.

In some embodiments, the modulator is orally active.

In a fifth aspect, the invention features a method of decreasing body mass or of decreasing adiposity or of decreasing percentage body fat comprising administering to a mammal in need thereof a therapeutically effective amount of a modulator of the mammalian GPR50 or a pharmaceutical composition comprising the modulator and a pharmaceutically acceptable carrier.

In some embodiments, the method is a method of decreasing body mass.

In some embodiments, the method is a method of decreasing adiposity.

In some embodiments, the method is a method of decreasing percentage body fat.

In some embodiments, the mammal is overweight or obese. In some embodiments, the mammal is overweight. In some embodiments, the mammal is obese.

In some embodiments, the modulator of the mammalian GPR50 is a modulator of a human GPR50. In some embodiments, the modulator of the human GPR50 is a modulator of human GPR50 having the amino acid sequence of SEQ ID NO: 2 or SEQ ID NO: 4. In some embodiments, the modulator of the human GPR50 is a modulator of human GPR50 having the amino acid sequence of SEQ ID NO: 2. In some embodiments, the modulator of the human GPR50 is a modulator of human GPR50 having the amino acid sequence of SEQ ID NO: 4.

In some embodiments, the modulator is according to the second aspect.

In some embodiments, the modulator is an agonist, partial agonist, inverse agonist, or antagonist of the mammalian GPR50.

In some embodiments, the modulator is an inverse agonist or antagonist of the mammalian GPR50. In some embodiments, the modulator is an inverse agonist. In some embodiments, the modulator is an antagonist.

In some embodiments, the modulator is a small molecule.

In some embodiments, the modulator is a polypeptide. In some embodiments, the modulator is not an antibody or an antigen-binding fragment thereof. In some embodiments, the modulator is a polypeptide, provided that the polypeptide is not an antibody or an antigen-binding fragment thereof. In some embodiments, the modulator is an antibody or an antigen-binding fragment thereof. In some embodiments, the modulator is a lipid. In some embodiments, the modulator is not a polypeptide. In some embodiments, the modulator is not a lipid. In some embodiments, the modulator is non-endogenous. In some embodiments, the modulator is not endogenous. In some embodiments, the modulator is not material that a prokaryote or eukaryote naturally produces. In some embodiments, the modulator is not material that a prokaryote naturally produces. In some embodiments, the modulator is not material that a eukaryote naturally produces. In some embodiments, the modulator is not material that a mammal naturally produces.

In some embodiments, the mammal is a mouse, a rat, or a human. In some embodiments, the mammal is a human.

In some embodiments, the modulator is an inverse agonist or antagonist with an $IC_{50}$ of less than about 10 µM, of less than about 1 µM, of less than about 100 nM, or of less than about 10 nM at human, mouse or rat GPR50, preferably at human GPR50. In some embodiments, the modulator is an inverse agonist or antagonist with an $IC_{50}$ of less than a value selected from the interval of about 10 nM to 10 µM. In some embodiments, the modulator is an inverse agonist or antagonist with an $IC_{50}$ of less than a value selected from the interval of about 10 nM to 1 µM. In some embodiments, the modulator is an inverse agonist or antagonist with an $IC_{50}$ of less than a value selected from the interval of about 10 nM to 100 nM. In some embodiments, the modulator is an inverse agonist or antagonist with an $IC_{50}$ of less than about 10 µM, of less than about 1 µM, of less than about 100 nM, or of less than about 10 nM in GTPγS binding assay carried out with membrane from transfected CHO cells, or in pigment aggregation assay carried out in transfected melanophores, or in cAMP assay carried out in transfected 293 cells optionally co-transfected with TSHR, wherein the transfected CHO cells or the transfected melanophore cells or the transfected 293 cells express a recombinant GPR50 having an amino acid sequence selected from SEQ ID NO: 2, SEQ ID NO: 4, SEQ ID NO: 6 and SEQ ID NO: 8. In some embodiments, the recombinant GPR50 has the amino acid sequence of SEQ ID NO: 2. In some embodiments, the recombinant GPR50 has the amino acid sequence of SEQ ID NO: 4. In some embodiments, the modulator is an inverse agonist or antagonist with an $IC_{50}$ of less than about 10 µM, of less than about 1 µM, of less than about 100 nM, or of less than about 10 nM in said assay. In some embodiments, the modulator is an inverse agonist or antagonist with an $IC_{50}$ in said assay of less than a value selected from the interval of about 10 nM to 10 µM. In some embodiments, the modulator is an inverse agonist or antagonist with an $IC_{50}$ in said assay of less than a value selected from the interval of about 10 nM to 1 µM. In some embodiments, the modulator is an inverse agonist or antagonist with an $IC_{50}$ in said assay of less than a value selected from the interval of about 10 nM to 100 nM.

In some embodiments, said administering is oral.

In a sixth aspect, the invention features a method of preventing or treating obesity or a condition related thereto comprising administering to a mammal in need thereof a therapeutically effective amount of a modulator of the mammalian GPR50 or a pharmaceutical composition comprising the modulator and a pharmaceutically acceptable carrier.

In some embodiments, the modulator of the mammalian GPR50 is a modulator of a human GPR50. In some embodiments, the modulator of the human GPR50 is a modulator of human GPR50 having the amino acid sequence of SEQ ID NO: 2 or SEQ ID NO: 4. In some embodiments, the modulator of the human GPR50 is a modulator of human GPR50 having the amino acid sequence of SEQ ID NO: 2. In some embodiments, the modulator of the human GPR50 is a modulator of human GPR50 having the amino acid sequence of SEQ ID NO: 4.

In some embodiments, the condition related to obesity is selected from the group consisting of hypertension, congestive cardiomyopathy, varicosities, pulmonary embolism, coronary heart disease, stroke, idiopathic intracranial hypertension, meralgia parethetica, dyspnea, obstructive sleep apnea, hypoventilation syndrome, Pickwickian syndrome, asthma, immobility, degenerative osteoarthritis, low back pain, striae distensae or "stretch marks," venous stasis of the lower extremities, lymphedema, cellulitis, intertrigo, carbuncles, acanthosis nigricans, skin tags, gastro-esophageal reflux disorder, nonalcoholic fatty liver/steatohepatitis, cholelithiasis, hernias, colon cancer, stress incontinence, obesity-related glomerulopathy, breast and uterine cancer, depression and low self-esteem, impaired quality of life, metabolic syndrome, insulin resistance, Type 2 diabetes, dyslipidemia, atherosclerosis, hyperandrogenemia in women, polycystic ovarian syndrome, dysmenorrhea, infertility, pregnancy complications, and male hypogonadism. In some embodiments, the condition related to obesity is selected from the group consisting of hypertension, insulin resistance, metabolic syndrome, Type 2 diabetes, dyslipidemia, atherosclerosis, coronary heart disease, and stroke.

In some embodiments, the modulator is according to the second aspect.

In some embodiments, the modulator is an agonist, partial agonist, inverse agonist, or antagonist of the mammalian GPR50.

In some embodiments, the modulator is an inverse agonist or antagonist of the mammalian GPR50. In some embodiments, the modulator is an inverse agonist. In some embodiments, the modulator is an antagonist.

In some embodiments, the modulator is a small molecule.

In some embodiments, the modulator is a polypeptide. In some embodiments, the modulator is not an antibody or an antigen-binding fragment thereof. In some embodiments, the modulator is a polypeptide, provided that the polypeptide is not an antibody or an antigen-binding fragment thereof. In some embodiments, the modulator is an antibody or an antigen-binding fragment thereof. In some embodiments, the modulator is a lipid. In some embodiments, the modulator is not a polypeptide. In some embodiments, the modulator is not a lipid. In some embodiments, the modulator is non-endogenous. In some embodiments, the modulator is not endogenous. In some embodiments, the modulator is not material that a prokaryote or eukaryote naturally produces. In some embodiments, the modulator is not material that a prokaryote naturally produces. In some embodiments, the modulator is not material that a eukaryote naturally produces. In some embodiments, the modulator is not material that a mammal naturally produces.

In some embodiments, the mammal is a mouse, a rat, or a human. In some embodiments, the mammal is a human.

In some embodiments, the modulator is an inverse agonist or antagonist with an $IC_{50}$ of less than about 10 µM, of less than about 1 µM, of less than about 100 nM, or of less than about 10 nM at human, mouse or rat GPR50, preferably at human GPR50. In some embodiments, the modulator is an inverse agonist or antagonist with an $IC_{50}$ of less than a value selected from the interval of about 10 nM to 10 µM. In some embodiments, the modulator is an inverse agonist or antagonist with an $IC_{50}$ of less than a value selected from the interval of about 10 nM to 1 µM. In some embodiments, the modulator is an inverse agonist or antagonist with an $IC_{50}$ of less than a value selected from the interval of about 10 nM to 100 nM. In some embodiments, the modulator is an inverse agonist or antagonist with an $IC_{50}$ of less than about 10 of less than about 1 µM, of less than about 100 nM, or of less than about 10 nM in GTPγS binding assay carried out with membrane from transfected CHO cells, or in pigment aggregation assay carried out in transfected melanophores, or in cAMP assay carried out in transfected 293 cells optionally co-transfected with TSHR, wherein the transfected CHO cells or the transfected melanophore cells or the transfected 293 cells express a recombinant GPR50 having an amino acid sequence selected from SEQ ID NO: 2, SEQ ID NO: 4, SEQ ID NO: 6 and SEQ ID NO: 8. In some embodiments, the recombinant GPR50 has the amino acid sequence of SEQ ID NO: 2. In some embodiments, the recombinant GPR50 has the amino acid sequence of SEQ ID NO: 4. In some embodiments, the modulator is an inverse agonist or antagonist with an $IC_{50}$ of less than about 10 µM, of less than about 1 of less than about 100 nM, or of less than about 10 nM in said assay. In some embodiments, the modulator is an inverse agonist or antagonist with an $IC_{50}$ in said assay of less than a value selected from the interval of about 10 nM to 10 µM. In some embodiments, the modulator is an inverse agonist or antagonist with an $IC_{50}$ in said assay of less than a value selected from the interval of about 10 nM to 1 µM. In some embodiments, the modulator is an inverse agonist or antagonist with an $IC_{50}$ in said assay of less than a value selected from the interval of about 10 nM to 100 nM.

In some embodiments, said administering is oral.

In a seventh aspect, the invention features a use of a modulator of a mammalian GPR50 in the manufacture of a medicament for decreasing body mass or for decreasing adiposity or for decreasing percentage body fat in the mammal.

In some embodiments, the medicament is for decreasing body mass in the mammal.

In some embodiments, the medicament is for decreasing adiposity in the mammal.

In some embodiments, the medicament is for decreasing percentage body fat in the mammal.

In some embodiments, the mammal is overweight or obese. In some embodiments, the mammal is overweight. In some embodiments, the mammal is obese.

In some embodiments, the modulator of the mammalian GPR50 is a modulator of a human GPR50. In some embodiments, the modulator of the human GPR50 is a modulator of human GPR50 having the amino acid sequence of SEQ ID NO: 2 or SEQ ID NO: 4. In some embodiments, the modulator of the human GPR50 is a modulator of human GPR50 having the amino acid sequence of SEQ ID NO: 2. In some embodiments, the modulator of the human GPR50 is a modulator of human GPR50 having the amino acid sequence of SEQ ID NO: 4.

In some embodiments, the modulator is according to the second aspect.

In some embodiments, the modulator is an agonist, partial agonist, inverse agonist, or antagonist of the mammalian GPR50.

In some embodiments, the modulator is an inverse agonist or antagonist of the mammalian GPR50. In some embodiments, the modulator is an inverse agonist. In some embodiments, the modulator is an antagonist.

In some embodiments, the modulator is a small molecule.

In some embodiments, the modulator is a polypeptide. In some embodiments, the modulator is not an antibody or an antigen-binding fragment thereof. In some embodiments, the modulator is a polypeptide, provided that the polypeptide is not an antibody or an antigen-binding fragment thereof. In some embodiments, the modulator is an antibody or an antigen-binding fragment thereof. In some embodiments, the modulator is a lipid. In some embodiments, the modulator is not a polypeptide. In some embodiments, the modulator is not a lipid. In some embodiments, the modulator is non-endogenous. In some embodiments, the modulator is not endogenous. In some embodiments, the modulator is not material that a prokaryote or eukaryote naturally produces. In some embodiments, the modulator is not material that a prokaryote naturally produces. In some embodiments, the modulator is not material that a eukaryote naturally produces. In some embodiments, the modulator is not material that a mammal naturally produces.

In some embodiments, the mammal is a mouse, a rat, a non-human primate, or a human. In some embodiments, the mammal is a human.

In some embodiments, the modulator is an inverse agonist or antagonist with an $IC_{50}$ of less than about 10 µM, of less than about 1 µM, of less than about 100 nM, or of less than about 10 nM at human, mouse or rat GPR50, preferably at human GPR50. In some embodiments, the modulator is an inverse agonist or antagonist with an $IC_{50}$ of less than a value selected from the interval of about 10 nM to 10 µM. In some embodiments, the modulator is an inverse agonist or antagonist with an $IC_{50}$ of less than a value selected from the interval of about 10 nM to 1 µM. In some embodiments, the modulator is an inverse agonist or antagonist with an $IC_{50}$ of less than a value selected from the interval of about 10 nM to 100 nM. In some embodiments, the modulator is an inverse agonist or antagonist with an $IC_{50}$ of less than about 10 µM, of less than about 1 µM, of less than about 100 nM, or of less than about 10 nM in GTPγS binding assay carried out with membrane from transfected CHO cells, or in pigment aggregation assay carried out in transfected melanophores, or in cAMP assay carried out in transfected 293 cells optionally co-transfected with TSHR, wherein the transfected CHO cells or the transfected melanophore cells or the transfected 293 cells express a recombinant GPR50 having an amino acid sequence selected from SEQ ID NO: 2, SEQ ID NO: 4, SEQ ID NO: 6 and SEQ ID NO: 8. In some embodiments, the recombinant GPR50 has the amino acid sequence of SEQ ID NO: 2. In some embodiments, the recombinant GPR50 has the amino acid sequence of SEQ ID NO: 4. In some embodiments, the modulator is an inverse agonist or antagonist with an $IC_{50}$ of less than about 10 µM, of less than about 1 µM, of less than about 100 nM, or of less than about 10 nM in said assay. In some embodiments, the modulator is an inverse agonist or antagonist with an $IC_{50}$ in said assay of less than a value selected from the interval of about 10 nM to 10 µM. In some embodiments, the modulator is an inverse agonist or antagonist with an $IC_{50}$ in said assay of less than a value selected from the interval of about 10 nM to 1 µM. In some embodiments, the modulator is an inverse agonist or antagonist with an $IC_{50}$ in said assay of less than a value selected from the interval of about 10 nM to 100 nM.

In some embodiments, the modulator is orally active.

In an eighth aspect, the invention features a use of a modulator of a mammalian GPR50 in the manufacture of a medicament for preventing or treating obesity or a condition related thereto in the mammal.

In some embodiments, the condition related to obesity is selected from the group consisting of hypertension, congestive cardiomyopathy, varicosities, pulmonary embolism, coronary heart disease, stroke, idiopathic intracranial hypertension, meralgia parethetica, dyspnea, obstructive sleep apnea, hypoventilation syndrome, Pickwickian syndrome, asthma, immobility, degenerative osteoarthritis, low back pain, striae distensae or "stretch marks," venous stasis of the lower extremities, lymphedema, cellulitis, intertrigo, carbuncles, acanthosis nigricans, skin tags, gastro-esophageal reflux disorder, nonalcoholic fatty liver/steatohepatitis, cholelithiasis, hernias, colon cancer, stress incontinence, obesity-related glomerulopathy, breast and uterine cancer, depression and low self-esteem, impaired quality of life, metabolic syndrome, insulin resistance, Type 2 diabetes, dyslipidemia, atherosclerosis, hyperandrogenemia in women, polycystic ovarian syndrome, dysmenorrhea, infertility, pregnancy complications, and male hypogonadism. In some embodiments, the condition related to obesity is selected from the group consisting of hypertension, insulin resistance, metabolic syndrome, Type 2 diabetes, dyslipidemia, atherosclerosis, coronary heart disease, and stroke.

In some embodiments, the modulator of the mammalian GPR50 is a modulator of a human GPR50. In some embodiments, the modulator of the human GPR50 is a modulator of human GPR50 having the amino acid sequence of SEQ ID NO: 2 or SEQ ID NO: 4. In some embodiments, the modulator of the human GPR50 is a modulator of human GPR50 having the amino acid sequence of SEQ ID NO: 2. In some embodiments, the modulator of the human GPR50 is a modulator of human GPR50 having the amino acid sequence of SEQ ID NO: 4.

In some embodiments, the modulator is according to the second aspect.

In some embodiments, the modulator is an agonist, partial agonist, inverse agonist, or antagonist of the mammalian GPR50.

In some embodiments, the modulator is an inverse agonist or antagonist of the mammalian GPR50. In some embodiments, the modulator is an inverse agonist. In some embodiments, the modulator is an antagonist.

In some embodiments, the modulator is a small molecule.

In some embodiments, the modulator is a polypeptide. In some embodiments, the modulator is not an antibody or an antigen-binding fragment thereof. In some embodiments, the modulator is a polypeptide, provided that the polypeptide is not an antibody or an antigen-binding fragment thereof. In some embodiments, the modulator is an antibody or an antigen-binding fragment thereof. In some embodiments, the modulator is a lipid. In some embodiments, the modulator is not a polypeptide. In some embodiments, the modulator is not a lipid. In some embodiments, the modulator is non-endogenous. In some embodiments, the modulator is not endogenous. In some embodiments, the modulator is not material that a prokaryote or eukaryote naturally produces. In some embodiments, the modulator is not material that a prokaryote naturally produces. In some embodiments, the modulator is not material that a eukaryote naturally produces. In some embodiments, the modulator is not material that a mammal naturally produces.

In some embodiments, the mammal is a mouse, a rat, a non-human primate, or a human. In some embodiments, the mammal is a human.

In some embodiments, the modulator is an inverse agonist or antagonist with an $IC_{50}$ of less than about 10 μM, of less than about 1 μM, of less than about 100 nM, or of less than about 10 nM at human, mouse or rat GPR50, preferably at human GPR50. In some embodiments, the modulator is an inverse agonist or antagonist with an $IC_{50}$ of less than a value selected from the interval of about 10 nM to 10 μM. In some embodiments, the modulator is an inverse agonist or antagonist with an $IC_{50}$ of less than a value selected from the interval of about 10 nM to 1 μM. In some embodiments, the modulator is an inverse agonist or antagonist with an $IC_{50}$ of less than a value selected from the interval of about 10 nM to 100 nM. In some embodiments, the modulator is an inverse agonist or antagonist with an $IC_{50}$ of less than about 10 of less than about 1 μM, of less than about 100 nM, or of less than about 10 nM in GTPγS binding assay carried out with membrane from transfected CHO cells, or in pigment aggregation assay carried out in transfected melanophores, or in cAMP assay carried out in transfected 293 cells optionally co-transfected with TSHR, wherein the transfected CHO cells or the transfected melanophore cells or the transfected 293 cells express a recombinant GPR50 having an amino acid sequence selected from SEQ ID NO: 2, SEQ ID NO: 4, SEQ ID NO: 6 and SEQ ID NO: 8. In some embodiments, the recombinant GPR50 has the amino acid sequence of SEQ ID NO: 2. In some embodiments, the recombinant GPR50 has the amino acid sequence of SEQ ID NO: 4. In some embodiments, the modulator is an inverse agonist or antagonist with an $IC_{50}$ of less than about 10 μM, of less than about 1 μM, of less than about 100 nM, or of less than about 10 nM in said assay. In some embodiments, the modulator is an inverse agonist or antagonist with an $IC_{50}$ in said assay of less than a value selected from the interval of about 10 nM to 10 μM. In some embodiments, the modulator is an inverse agonist or antagonist with an $IC_{50}$ in said assay of less than a value selected from the interval of about 10 nM to 1 μM. In some embodiments, the modulator is an inverse agonist or antagonist with an $IC_{50}$ in said assay of less than a value selected from the interval of about 10 nM to 100 nM.

In some embodiments, the modulator is orally active.

In a ninth aspect, the invention features a modulator of a mammalian GPR50 for use to decrease body mass in the mammal, for use to decrease adiposity in the mammal, for use to decrease percentage body fat in the mammal, or for use to prevent or treat obesity or a condition related thereto in the mammal.

In some embodiments, the condition related to obesity is selected from the group consisting of hypertension, congestive cardiomyopathy, varicosities, pulmonary embolism, coronary heart disease, stroke, idiopathic intracranial hypertension, meralgia parethetica, dyspnea, obstructive sleep apnea, hypoventilation syndrome, Pickwickian syndrome, asthma, immobility, degenerative osteoarthritis, low back pain, striae distensae or "stretch marks," venous stasis of the lower extremities, lymphedema, cellulitis, intertrigo, carbuncles, acanthosis nigricans, skin tags, gastro-esophageal reflux disorder, nonalcoholic fatty liver/steatohepatitis, cholelithiasis, hernias, colon cancer, stress incontinence, obesity-related glomerulopathy, breast and uterine cancer, depression and low self-esteem, impaired quality of life, metabolic syndrome, insulin resistance, Type 2 diabetes, dyslipidemia, atherosclerosis, hyperandrogenemia in women, polycystic ovarian syndrome, dysmenorrhea, infertility, pregnancy complications, and male hypogonadism. In some embodiments, the condition related to obesity is selected from the group consisting of hypertension, insulin resistance, metabolic syndrome, Type 2 diabetes, dyslipidemia, atherosclerosis, coronary heart disease, and stroke.

In some embodiments, the modulator of the mammalian GPR50 is a modulator of a human GPR50. In some embodiments, the modulator of the human GPR50 is a modulator of human GPR50 having the amino acid sequence of SEQ ID NO: 2 or SEQ ID NO: 4. In some embodiments, the modulator of the human GPR50 is a modulator of human GPR50 having the amino acid sequence of SEQ ID NO: 2. In some embodiments, the modulator of the human GPR50 is a modulator of human GPR50 having the amino acid sequence of SEQ ID NO: 4.

In some embodiments, the modulator is according to the second aspect.

In some embodiments, the modulator is an agonist, partial agonist, inverse agonist, or antagonist of the mammalian GPR50.

In some embodiments, the modulator is an inverse agonist or antagonist of the mammalian GPR50. In some embodiments, the modulator is an inverse agonist. In some embodiments, the modulator is an antagonist.

In some embodiments, the modulator is a small molecule.

In some embodiments, the modulator is a polypeptide. In some embodiments, the modulator is not an antibody or an antigen-binding fragment thereof. In some embodiments, the modulator is a polypeptide, provided that the polypeptide is not an antibody or an antigen-binding fragment thereof. In some embodiments, the modulator is an antibody or an antigen-binding fragment thereof. In some embodiments, the modulator is a lipid. In some embodiments, the modulator is not a polypeptide. In some embodiments, the modulator is not a lipid. In some embodiments, the modulator is non-endogenous. In some embodiments, the modulator is not endogenous. In some embodiments, the modulator is not material that a prokaryote or eukaryote naturally produces. In some embodiments, the modulator is not material that a prokaryote naturally produces. In some embodiments, the modulator is not material that a eukaryote naturally produces. In some embodiments, the modulator is not material that a mammal naturally produces.

In some embodiments, the mammal is a mouse, a rat, a non-human primate, or a human. In some embodiments, the mammal is a human.

In some embodiments, the modulator is an inverse agonist or antagonist with an $IC_{50}$ of less than about 10 µM, of less than about 1 µM, of less than about 100 nM, or of less than about 10 nM at human, mouse or rat GPR50, preferably at human GPR50. In some embodiments, the modulator is an inverse agonist or antagonist with an $IC_{50}$ of less than a value selected from the interval of about 10 nM to 10 µM. In some embodiments, the modulator is an inverse agonist or antagonist with an $IC_{50}$ of less than a value selected from the interval of about 10 nM to 1 µM. In some embodiments, the modulator is an inverse agonist or antagonist with an $IC_{50}$ of less than a value selected from the interval of about 10 nM to 100 nM. In some embodiments, the modulator is an inverse agonist or antagonist with an $IC_{50}$ of less than about 10 µM, of less than about 1 µM, of less than about 100 nM, or of less than about 10 nM in GTPγS binding assay carried out with membrane from transfected CHO cells, or in pigment aggregation assay carried out in transfected melanophores, or in cAMP assay carried out in transfected 293 cells optionally co-transfected with TSHR, wherein the transfected CHO cells or the transfected melanophore cells or the transfected 293 cells express a recombinant GPR50 having an amino acid sequence selected from SEQ ID NO: 2, SEQ ID NO: 4, SEQ ID NO: 6 and SEQ ID NO: 8. In some embodiments, the recombinant GPR50 has the amino acid sequence of SEQ ID NO: 2. In some embodiments, the recombinant GPR50 has the amino acid sequence of SEQ ID NO: 4. In some embodiments, the modulator is an inverse agonist or antagonist with an $IC_{50}$ of less than about 10 µM, of less than about 1 µM, of less than about 100 nM, or of less than about 10 nM in said assay. In some embodiments, the modulator is an inverse agonist or antagonist with an $IC_{50}$ in said assay of less than a value selected from the interval of about 10 nM to 10 µM. In some embodiments, the modulator is an inverse agonist or antagonist with an $IC_{50}$ in said assay of less than a value selected from the interval of about 10 nM to 1 µM. In some embodiments, the modulator is an inverse agonist or antagonist with an $IC_{50}$ in said assay of less than a value selected from the interval of about 10 nM to 100 nM.

In some embodiments, the modulator is orally active.

In a tenth aspect, the invention features a pharmaceutical composition comprising a modulator of a mammalian GPR50 and a pharmaceutically acceptable carrier for use to decrease body mass in the mammal, for use to decrease adiposity in the mammal, for use to decrease percentage body fat in the mammal, or for use to prevent or treat obesity or a condition related thereto in the mammal.

In some embodiments, the condition related to obesity is selected from the group consisting of hypertension, congestive cardiomyopathy, varicosities, pulmonary embolism, coronary heart disease, stroke, idiopathic intracranial hypertension, meralgia parethetica, dyspnea, obstructive sleep apnea, hypoventilation syndrome, Pickwickian syndrome, asthma, immobility, degenerative osteoarthritis, low back pain, striae distensae or "stretch marks," venous stasis of the lower extremities, lymphedema, cellulitis, intertrigo, carbuncles, acanthosis nigricans, skin tags, gastro-esophageal reflux disorder, nonalcoholic fatty liver/steatohepatitis, cholelithiasis, hernias, colon cancer, stress incontinence, obesity-related glomerulopathy, breast and uterine cancer, depression and low self-esteem, impaired quality of life, metabolic syndrome, insulin resistance, Type 2 diabetes, dyslipidemia, atherosclerosis, hyperandrogenemia in women, polycystic ovarian syndrome, dysmenorrhea, infertility, pregnancy complications, and male hypogonadism. In some embodiments, the condition related to obesity is selected from the group consisting of hypertension, insulin resistance, metabolic syndrome, Type 2 diabetes, dyslipidemia, atherosclerosis, coronary heart disease, and stroke.

In some embodiments, the modulator of the mammalian GPR50 is a modulator of a human GPR50. In some embodiments, the modulator of the human GPR50 is a modulator of human GPR50 having the amino acid sequence of SEQ ID NO: 2 or SEQ ID NO: 4. In some embodiments, the modulator of the human GPR50 is a modulator of human GPR50 having the amino acid sequence of SEQ ID NO: 2. In some embodiments, the modulator of the human GPR50 is a modulator of human GPR50 having the amino acid sequence of SEQ ID NO: 4.

In some embodiments, the modulator is according to the second aspect.

In some embodiments, the modulator is an agonist, partial agonist, inverse agonist, or antagonist of the mammalian GPR50.

In some embodiments, the modulator is an inverse agonist or antagonist of the mammalian GPR50. In some embodiments, the modulator is an inverse agonist. In some embodiments, the modulator is an antagonist.

In some embodiments, the modulator is a small molecule.

In some embodiments, the modulator is a polypeptide. In some embodiments, the modulator is not an antibody or an antigen-binding fragment thereof. In some embodiments, the modulator is a polypeptide, provided that the polypeptide is not an antibody or an antigen-binding fragment thereof. In some embodiments, the modulator is an antibody or an antigen-binding fragment thereof. In some embodiments, the modulator is a lipid. In some embodiments, the modulator is not a polypeptide. In some embodiments, the modulator is not a lipid. In some embodiments, the modulator is non-endogenous. In some embodiments, the modulator is not endogenous. In some embodiments, the modulator is not material that a prokaryote or eukaryote naturally produces. In some embodiments, the modulator is not material that a prokaryote naturally produces. In some embodiments, the modulator is not material that a eukaryote naturally produces. In some embodiments, the modulator is not material that a mammal naturally produces.

In some embodiments, the mammal is a mouse, a rat, a non-human primate, or a human. In some embodiments, the mammal is a human.

In some embodiments, the modulator is an inverse agonist or antagonist with an $IC_{50}$ of less than about 10 µM, of less than about 1 µM, of less than about 100 nM, or of less than about 10 nM at human, mouse or rat GPR50, preferably at human GPR50. In some embodiments, the modulator is an inverse agonist or antagonist with an $IC_{50}$ of less than a value selected from the interval of about 10 nM to 10 µM. In some embodiments, the modulator is an inverse agonist or antagonist with an $IC_{50}$ of less than a value selected from the interval of about 10 nM to 1 µM. In some embodiments, the modulator is an inverse agonist or antagonist with an $IC_{50}$ of less than a value selected from the interval of about 10 nM to 100 nM. In some embodiments, the modulator is an inverse agonist or antagonist with an $IC_{50}$ of less than about 10 µM, of less than about 1 µM, of less than about 100 nM, or of less than about 10 nM in GTPγS binding assay carried out with membrane from transfected CHO cells, or in pigment aggregation assay carried out in transfected melanophores, or in cAMP assay carried out in transfected 293 cells optionally co-transfected with TSHR, wherein the transfected CHO cells or the transfected melanophore cells or the transfected 293 cells express a recombinant GPR50 having an amino acid sequence selected from SEQ ID NO: 2, SEQ ID NO: 4, SEQ ID NO: 6 and SEQ ID NO: 8. In some embodiments, the recombinant GPR50 has the amino acid sequence of SEQ ID NO: 2. In some embodiments, the recombinant GPR50 has the amino acid sequence of SEQ ID NO: 4. In some embodiments, the modulator is an inverse agonist or antagonist with an $IC_{50}$ of less than about 10 µM, of less than about 1 µM, of less than about 100 nM, or of less than about 10 nM in said assay. In some embodiments, the modulator is an inverse agonist or antagonist with an $IC_{50}$ in said assay of less than a value selected from the interval of about 10 nM to 10 µM. In some embodiments, the modulator is an inverse agonist or antagonist with an $IC_{50}$ in said assay of less than a value selected from the interval of about 10 nM to 1 µM. In some embodiments, the modulator is an inverse agonist or antagonist with an $IC_{50}$ in said assay of less than a value selected from the interval of about 10 nM to 100 nM.

In some embodiments, the modulator is orally active.

In an eleventh aspect, the invention features a method of identifying a candidate compound as a ligand of a GPCR comprising an amino acid sequence selected from the group consisting of (a) the amino acid sequence of SEQ ID NO: 2;
(b) amino acids 2-617 of SEQ ID NO: 2;
(c) amino acids 2-617 of SEQ ID NO:2, wherein the GPCR does not comprise amino acids 1-617 of SEQ ID NO: 2;
(d) the amino acid sequence of (a), (b) or (c), wherein SEQ ID NO: 2 comprises any combination of a substitution of serine at amino acid position 493 of SEQ ID NO: 2 with asparagine, a substitution of threonine at amino acid position 532 of SEQ ID NO: 2 with alanine, and a substitution of valine at amino acid position 606 of SEQ ID NO: 2 with isoleucine;
(c) the amino acid sequence of SEQ ID NO: 4;
(d) amino acids 2-613 of SEQ ID NO: 4;
(e) amino acids 2-613 of SEQ ID NO: 4, wherein the GPCR does not comprise amino acids 1-613 of SEQ ID NO: 4;
(f) the amino acid sequence of (e), (f) or (g), wherein SEQ ID NO: 4 comprises any combination of a substitution of asparagine at amino acid position 493 of SEQ ID NO: 4 with serine, a substitution of alanine at amino acid position 528 of SEQ ID NO: 4 with threonine, and a substitution of valine at amino acid position 602 of SEQ ID NO: 4 with isoleucine;
(g) the amino acid sequence of a G protein-coupled receptor encoded by a polynucleotide that is amplifiable by polymerase chain reaction (PCR) on a human DNA sample using specific primers SEQ ID NO: 9 and SEQ ID NO: 10;
(h) the amino acid sequence of a G protein-coupled receptor encoded by a polynucleotide hybridizing at high stringency to the complement of SEQ ID NO: 1 or SEQ ID NO: 3;
(i) the amino acid sequence of a G protein-coupled receptor having at least about 75%, at least about 80%, at least about 85%, at least about 90% or at least about 95% identity to SEQ ID NO: 2 or SEQ ID NO: 4;
(j) the amino acid sequence of SEQ ID NO: 6;
(k) amino acids 2-591 of SEQ ID NO: 6;
(l) amino acids 2-591 of SEQ ID NO: 6 wherein the GPCR does not comprise amino acids 1-591 of SEQ ID NO: 6;
(m) the amino acid sequence of a G protein-coupled receptor encoded by a polynucleotide hybridizing at high stringency to the complement of SEQ ID NO: 5;
(n) the amino acid sequence of a G protein-coupled receptor having at least about 75%, at least about 80%, at least about 85%, at least about 90% or at least about 95% identity to SEQ ID NO: 6;
(o) the amino acid sequence of SEQ ID NO:8;
(p) amino acids 2-594 of SEQ ID NO:8;
(q) amino acids 2-594 of SEQ ID NO:8, wherein the GPCR does not comprise amino acids 1-594 of SEQ ID NO:8;
(r) the amino acid sequence of a G protein-coupled receptor encoded by a polynucleotide hybridizing at high stringency to the complement of SEQ ID NO: 7;
(s) the amino acid sequence of a G protein-coupled receptor having at least about 75%, at least about 80%, at least about 85%, at least about 90% or at least about 95% identity to SEQ ID NO: 8; and
(t) the amino acid sequence of a G protein-coupled receptor that is a constitutively active version of a receptor having SEQ ID NO: 2 or SEQ ID NO: 4;
or a variant or biologically active fragment thereof;
comprising the steps of:
(a') contacting said GPCR with an optionally labeled known ligand to the GPCR in the presence or absence of the candidate compound;
(b') detecting the complex between the known ligand and said GPCR; and
(c') determining whether less of said complex is formed in the presence of the candidate compound than in the absence of the candidate compound;
wherein said determination is indicative of the candidate compound being a ligand of said receptor.

In some embodiments, the GPCR comprises the amino acid sequence of a G protein-coupled receptor having at least about 75%, at least about 80%, at least about 85%, at least about 90% or at least about 95% identity to SEQ ID NO: 2 or SEQ ID NO: 4.

In some embodiments, the G protein-coupled receptor having at least about 75%, at least about 80%, at least about 85%, at least about 90% or at least about 95% identity to SEQ ID NO: 2, SEQ ID NO: 4, SEQ ID NO: 6 or SEQ ID NO: 8 is an endogenous GPCR. In some embodiments, the G protein-coupled receptor having at least about 75%, at least about 80%, at least about 85%, at least about 90% or at least about 95% identity to SEQ ID NO: 2, SEQ ID NO: 4, SEQ ID NO: 6 or SEQ ID NO: 8 is a mammalian endogenous GPCR. In some embodiments, the G protein-coupled receptor having at least about 75%, at least about 80%, at least about 85%, at least about 90% or at least about 95% identity to SEQ ID NO: 2, SEQ ID NO: 4, SEQ ID NO: 6 or SEQ ID NO: 8 is a non-endogenous GPCR.

In some embodiments, the G protein-coupled receptor that is a constitutively active version of a receptor having SEQ ID NO: 2 or SEQ ID NO: 4 is an endogenous G protein-coupled receptor. In some embodiments, the G protein-coupled receptor that is a constitutively active version of a receptor having SEQ ID NO: 2 or SEQ ID NO: 4 is a non-endogenous G protein-coupled receptor.

In some embodiments, PCR is RT-PCR.

In some embodiments, the human DNA is human cDNA derived from a tissue or cell type that expresses GPR50. In some embodiments, the human cDNA is derived from hypothalamus or pituitary.

In some embodiments, the G protein-coupled receptor encoded by a polynucleotide that is amplifiable by polymerase chain reaction (PCR) on a human DNA sample using specific primers SEQ ID NO: 9 and SEQ ID NO: 10 is an endogenous GPR50 G protein-coupled receptor.

In some embodiments, the GPCR is recombinant.

In some embodiments, the GPCR is endogenous. In some embodiments, the GPCR that is endogenous is a mammalian endogenous GPCR. In some embodiments, the mammalian endogenous GPCR is a mammalian endogenous GPR50. In some embodiments, the GPCR is non-endogenous.

In some embodiments, the GPCR is a mammalian GPR50.

In some embodiments, the G protein-coupled receptor encoded by a polynucleotide hybridizing at high stringency to the complement of SEQ ID NO: 1, SEQ ID NO: 3, SEQ ID NO: 5 or SEQ ID NO: 7 is an endogenous GPCR. In some embodiments, the G protein-coupled receptor encoded by a polynucleotide hybridizing at high stringency to the complement of SEQ ID NO: 1, SEQ ID NO: 3, SEQ ID NO: 5 or SEQ ID NO: 7 that is an endogenous GPCR is a mammalian GPCR. In some embodiments, the G protein-coupled receptor encoded by a polynucleotide hybridizing at high stringency to the complement of SEQ ID NO: 1, SEQ ID NO: 3, SEQ ID NO: 5 or SEQ ID NO: 7 exhibits a detectable level of constitutive activity. In some embodiments, the constitutive activity is for lowering a level of intracellular cAMP. In some embodiments, the constitutive activity is for causing melanophore cells to undergo pigment aggregation. In certain embodiments, the G protein-coupled receptor encoded by a polynucleotide hybridizing at high stringency to the complement of SEQ ID NO: 1, SEQ ID NO: 3, SEQ ID NO: 5 or SEQ ID NO: 7 specifically binds an antibody that recognizes an mammalian endogenous GPR50 (an antibody that recognizes an endogenous mammalian GPR50 can be obtained commercially from, e.g., Advanced Targeting Systems, San Diego, Calif.; and CHEMICON International, Inc., Temecula, Calif.) or specifically binds a known ligand of an mammalian endogenous GPR50. In certain embodiments, the known ligand of the mammalian endogenous GPR50 is an endogenous ligand of the mammalian endogenous GPR50.

In some embodiments, the known ligand to the GPCR is a known ligand to a mammalian GPR50. In some embodiments, the known ligand to the GPCR is a known ligand to a human GPR50.

In some embodiments, the known ligand to the GPCR is a known ligand to SEQ ID NO: 2. In some embodiments, the known ligand to the GPCR is a known ligand to SEQ ID NO: 4. In some embodiments, the known ligand to the GPCR is a known ligand to SEQ ID NO: 6. In some embodiments, the known ligand to the GPCR is a known ligand to SEQ ID NO: 8.

In some embodiments, the known ligand is not an antibody or an antigen-binding fragment thereof.

In some embodiments, the known ligand is radiolabeled.

In some embodiments, the candidate compound is a small molecule.

In some embodiments, the candidate compound is a polypeptide. In some embodiments, the candidate compound is not an antibody or an antigen-binding fragment thereof. In some embodiments, the candidate compound is a polypeptide, provided that the polypeptide is not an antibody or an antigen-binding fragment thereof. In some embodiments, the candidate compound is an antibody or an antigen-binding fragment thereof. In some embodiments, the candidate compound is a lipid. In some embodiments, the candidate compound is not a polypeptide. In some embodiments, the candidate compound is not a lipid. In some embodiments, the candidate compound is non-endogenous. In some embodiments, the candidate compound is not endogenous. In some embodiments, the candidate compound is not material that a prokaryote or eukaryote naturally produces. In some embodiments, the candidate compound is not material that a prokaryote naturally produces. In some embodiments, the candidate compound is not material that a eukaryote naturally produces. In some embodiments, the candidate compound is not material that a mammal naturally produces. In some embodiments, the candidate compound is a compound not known to be a ligand of the GPCR.

In some embodiments, the method is for screening candidate compounds as modulators of body mass or of adiposity or of percentage body fat in a subject or as pharmaceutical agents for obesity or a condition related thereto. In some embodiments, the condition related to obesity is selected from the group consisting of hypertension, congestive cardiomyopathy, varicosities, pulmonary embolism, coronary heart disease, stroke, idiopathic intracranial hypertension, meralgia parethetica, dyspnea, obstructive sleep apnea, hypoventilation syndrome, Pickwickian syndrome, asthma, immobility, degenerative osteoarthritis, low back pain, striae distensae or "stretch marks," venous stasis of the lower extremities, lymphedema, cellulitis, intertrigo, carbuncles, acanthosis nigricans, skin tags, gastro-esophageal reflux disorder, nonalcoholic fatty liver/steatohepatitis, cholelithiasis, hernias, colon cancer, stress incontinence, obesity-related glomerulopathy, breast and uterine cancer, depression and low self-esteem, impaired quality of life, metabolic syndrome, insulin resistance, Type 2 diabetes, dyslipidemia, atherosclerosis, hyperandrogenemia in women, polycystic ovarian syndrome, dysmenorrhea, infertility, pregnancy complications, and male hypogonadism. In some embodiments, the condition related to obesity is selected from the group consisting of hypertension, insulin resistance, metabolic syndrome, Type 2 diabetes, dyslipidemia, atherosclerosis, coronary heart disease, and stroke. In some embodiments, the subject is a mammal. In some embodiments, the subject is a mammal selected from the group consisting of mouse, rat and human. In some embodiments, the subject is a human.

In some embodiments, the method is for screening candidate compounds as compounds useful in radio-imaging for identifying a subject at risk for obesity or a condition related thereto. In some embodiments, the subject is a human.

In a twelfth aspect, the invention features a transgenic non-human mammal comprising a disruption in an endogenous GPR50 gene, wherein the disruption is homozygous, the transgenic non-human mammal lacks production of functional GPR50 protein and exhibits, relative to the wild-type mammal, a decreased weight gain induced by a high fat diet.

In some embodiments, the transgenic non-human mammal is a mouse, a rat or a pig. In some embodiments, the transgenic non-human mammal is a mouse.

In an thirteenth aspect, the invention features a method of identifying a candidate compound as a modulator of body mass or of adiposity or of percentage body fat in a subject, the method comprising:
providing a transgenic non-human mammal according to the twelfth aspect;
administering the candidate compound to the transgenic non-human mammal; and
determining whether the decreased weight gain induced by a high-fat diet is modulated by the candidate compound, thereby identifying the candidate compound as a modulator of body mass or of adiposity or of percentage body fat in the subject.

In some embodiments, the modulator of body mass or of adiposity or of percentage body fat in a subject is a modulator of body mass in the subject.

In some embodiments, the modulator of body mass or of adiposity or of percentage body fat in a subject is a modulator of adiposity in the subject.

In some embodiments, the modulator of body mass or of adiposity or of percentage body fat in a subject is a modulator of percentage body fat in the subject.

In some embodiments, the transgenic non-human mammal is a mouse, a rat or a pig. In some embodiments, the transgenic non-human mammal is a mouse.

In some embodiments, the candidate compound is a small molecule.

In some embodiments, the candidate compound is a polypeptide. In some embodiments, the candidate compound is not an antibody or an antigen-binding fragment thereof. In some embodiments, the candidate compound is a polypeptide, provided that the polypeptide is not an antibody or an antigen-binding fragment thereof. In some embodiments, the candidate compound is an antibody or an antigen-binding fragment thereof. In some embodiments, the candidate compound is a lipid. In some embodiments, the candidate compound is not a polypeptide. In some embodiments, the candidate compound is not a lipid. In some embodiments, the candidate compound is non-endogenous. In some embodiments, the candidate compound is not endogenous. In some embodiments, the candidate compound is not material that a prokaryote or eukaryote naturally produces. In some embodiments, the candidate compound is not material that a prokaryote naturally produces. In some embodiments, the candidate compound is not material that a eukaryote naturally produces. In some embodiments, the candidate compound is not material that a mammal naturally produces.

In some embodiments, the subject is a mammal. In some embodiments, the subject that is a mammal is selected from the group consisting of mouse, rat and human. In some embodiments, the subject that is a mammal is a human.

In a fourteenth aspect, the invention features use of a GPCR to screen candidate compounds as modulators of body mass or of adiposity or of percentage body fat in a mammal or as pharmaceutical agents for obesity or a condition related thereto, wherein the GPCR comprises an amino acid sequence selected from the group consisting of:

(a) the amino acid sequence of SEQ ID NO: 2;
(b) amino acids 2-617 of SEQ ID NO: 2;
(c) amino acids 2-617 of SEQ ID NO:2, wherein the GPCR does not comprise amino acids 1-617 of SEQ ID NO: 2;
(d) the amino acid sequence of (a), (b) or (c), wherein SEQ ID NO: 2 comprises any combination of a substitution of serine at amino acid position 493 of SEQ ID NO: 2 with asparagine, a substitution of threonine at amino acid position 532 of SEQ ID NO: 2 with alanine, and a substitution of valine at amino acid position 606 of SEQ ID NO: 2 with isoleucine;
(e) the amino acid sequence of SEQ ID NO: 4;
(f) amino acids 2-613 of SEQ ID NO: 4;
(g) amino acids 2-613 of SEQ ID NO: 4, wherein the GPCR does not comprise amino acids 1-613 of SEQ ID NO: 4;
(h) the amino acid sequence of (e), (f) or (g), wherein SEQ ID NO: 4 comprises any combination of a substitution of asparagine at amino acid position 493 of SEQ ID NO: 4 with serine, a substitution of alanine at amino acid position 528 of SEQ ID NO: 4 with threonine, and a substitution of valine at amino acid position 602 of SEQ ID NO: 4 with isoleucine;
(i) the amino acid sequence of a G protein-coupled receptor encoded by a polynucleotide that is amplifiable by polymerase chain reaction (PCR) on a human DNA sample using specific primers SEQ ID NO: 9 and SEQ ID NO: 10;
(j) the amino acid sequence of a G protein-coupled receptor encoded by a polynucleotide hybridizing at high stringency to the complement of SEQ ID NO: 1 or SEQ ID NO: 3;
(k) the amino acid sequence of an endogenous G protein-coupled receptor having at least about 95% identity to SEQ ID NO: 2 or SEQ ID NO: 4;
(l) the amino acid sequence of SEQ ID NO: 6;
(m) amino acids 2-591 of SEQ ID NO: 6;
(n) amino acids 2-591 of SEQ ID NO: 6 wherein the GPCR does not comprise amino acids 1-591 of SEQ ID NO: 6;
(o) the amino acid sequence of a G protein-coupled receptor encoded by a polynucleotide hybridizing at high stringency to the complement of SEQ ID NO: 5;
(p) the amino acid sequence of a G protein-coupled receptor having at least about 75%, at least about 80%, at least about 85%, at least about 90% or at least about 95% identity to SEQ ID NO: 6;
(q) the amino acid sequence of SEQ ID NO:8;
(r) amino acids 2-594 of SEQ ID NO:8;
(s) amino acids 2-594 of SEQ ID NO:8, wherein the GPCR does not comprise amino acids 1-594 of SEQ ID NO:8;
(t) the amino acid sequence of a G protein-coupled receptor encoded by a polynucleotide hybridizing at high stringency to the complement of SEQ ID NO: 7;
(u) the amino acid sequence of a G protein-coupled receptor having at least about 75%, at least about 80%, at least about 85%, at least about 90% or at least about 95% identity to SEQ ID NO: 8; and
(v) the amino acid sequence of a G protein-coupled receptor that is a constitutively active version of a receptor having SEQ ID NO: 2 or SEQ ID NO: 4;
or a variant or biologically active fragment thereof.

In some embodiments, the GPCR comprises the amino acid sequence of SEQ ID NO: 2 or SEQ ID NO: 4.

In some embodiments, the GPCR comprises the amino acid sequence of a G protein-coupled receptor having at least about 75%, at least about 80%, at least about 85%, at least about 90% or at least about 95% identity to SEQ ID NO: 2 or SEQ ID NO: 4.

In some embodiments, the G protein-coupled receptor having at least about 75%, at least about 80%, at least about 85%, at least about 90% or at least about 95% identity to SEQ ID NO: 2, SEQ ID NO: 4, SEQ ID NO: 6 or SEQ ID NO: 8 is an endogenous GPCR. In some embodiments, the G protein-coupled receptor having at least about 75%, at least about 80%, at least about 85%, at least about 90% or at least about 95% identity to SEQ ID NO: 2, SEQ ID NO: 4, SEQ ID NO: 6 or SEQ ID NO: 8 is a mammalian endogenous GPCR. In some embodiments, the G protein-coupled receptor having at least about 75%, at least about 80%, at least about 85%, at least about 90% or at least about 95% identity to SEQ ID NO: 2, SEQ ID NO: 4, SEQ ID NO: 6 or SEQ ID NO: 8 is a non-endogenous GPCR.

In some embodiments, the G protein-coupled receptor that is a constitutively active version of a receptor having SEQ ID NO: 2 or SEQ ID NO: 4 is an endogenous G protein-coupled receptor. In some embodiments, the G protein-coupled receptor that is a constitutively active version of a receptor having SEQ ID NO: 2 or SEQ ID NO: 4 is a non-endogenous G protein-coupled receptor.

In some embodiments, the modulator of body mass in a mammal is a compound that decreases body mass in a mammal. In some embodiments, the modulator of adiposity in a mammal is a compound that decreases adiposity in a mammal. In some embodiments, the modulator of percentage body fat in a mammal is a compound that decreases percentage body fat in a mammal. In some embodiments, the mammal is a human.

In some embodiments, the modulator of body mass in a mammal is a compound that increases body mass in a mammal. In some embodiments, the modulator of adiposity in a mammal is a compound that increases adiposity in a mammal. In some embodiments, the modulator of percentage body fat in a mammal is a compound that increases percentage body fat in a mammal. In some embodiments, the mammal is a human. In some embodiments, the compound that increases body mass or increases adiposity or increases percentage body fat in a mammal is a compound for preventing or treating cachexia, wasting, AIDS-related weight loss, cancer-related weight loss, anorexia, or bulimia in the mammal. In some embodiments, the compound that increases body mass or increases adiposity or increases percentage body fat in a mammal is a compound for use to prevent or treat cachexia, wasting, AIDS-related weight loss, cancer-related weight loss, anorexia, or bulimia in the mammal.

In some embodiments, PCR is RT-PCR.

In some embodiments, the human DNA is human cDNA derived from a tissue or cell type that expresses GPR50. In some embodiments, the human cDNA is derived from hypothalamus or pituitary.

In some embodiments, the G protein-coupled receptor encoded by a polynucleotide that is amplifiable by polymerase chain reaction (PCR) on a human DNA sample using specific primers SEQ ID NO: 9 and SEQ ID NO: 10 is an endogenous GPR50 G protein-coupled receptor.

In some embodiments, the G protein-coupled receptor encoded by a polynucleotide hybridizing at high stringency to the complement of SEQ ID NO: 1, SEQ ID NO: 3, SEQ ID NO: 5 or SEQ ID NO: 7 is an endogenous GPCR. In some embodiments, the G protein-coupled receptor encoded by a polynucleotide hybridizing at high stringency to the complement of SEQ ID NO: 1, SEQ ID NO: 3, SEQ ID NO: 5 or SEQ ID NO: 7 that is an endogenous GPCR is a mammalian GPCR. In some embodiments, the G protein-coupled receptor encoded by a polynucleotide hybridizing at high stringency to the complement of SEQ ID NO: 1, SEQ ID NO: 3, SEQ ID NO: 5 or SEQ ID NO: 7 exhibits a detectable level of constitutive activity. In some embodiments, the constitutive activity is for lowering a level of intracellular cAMP. In some embodiments, the constitutive activity is for causing melanophore cells to undergo pigment aggregation. In certain embodiments, the G protein-coupled receptor encoded by a polynucleotide hybridizing at high stringency to the complement of SEQ ID NO: 1, SEQ ID NO: 3, SEQ ID NO: 5 or SEQ ID NO: 7 specifically binds an antibody that recognizes an mammalian endogenous GPR50 (an antibody that recognizes an endogenous mammalian GPR50 can be obtained commercially from, e.g., Advanced Targeting Systems, San Diego, Calif.; and CHEMICON International, Inc., Temecula, Calif.) or specifically binds a known ligand of an mammalian endogenous GPR50. In certain embodiments, the known ligand of the mammalian endogenous GPR50 is an endogenous ligand of the mammalian endogenous GPR50.

In some embodiments, the GPCR is recombinant.

In some embodiments, the GPCR is endogenous. In some embodiments, the GPCR that is endogenous is a mammalian endogenous GPCR. In some embodiments, the mammalian endogenous GPCR is a mammalian endogenous GPR50. In some embodiments, the GPCR is non-endogenous.

In some embodiments, the GPCR is a mammalian GPR50.

In some embodiments, the candidate compound is a small molecule.

In some embodiments, the candidate compound is a polypeptide. In some embodiments, the candidate compound is not an antibody or an antigen-binding fragment thereof. In some embodiments, the candidate compound is a polypeptide, provided that the polypeptide is not an antibody or an antigen-binding fragment thereof. In some embodiments, the candidate compound is an antibody or an antigen-binding fragment thereof. In some embodiments, the candidate compound is a lipid. In some embodiments, the candidate compound is not a polypeptide. In some embodiments, the candidate compound is not a lipid. In some embodiments, the candidate compound is non-endogenous. In some embodiments, the candidate compound is not endogenous. In some embodiments, the candidate compound is not material that a prokaryote or eukaryote naturally produces. In some embodiments, the candidate compound is not material that a prokaryote naturally produces. In some embodiments, the candidate compound is not material that a eukaryote naturally produces. In some embodiments, the candidate compound is not material that a mammal naturally produces. In some embodiments, the candidate compound is a compound not known to be a ligand of the GPCR. In some embodiments, the candidate compound is a compound not known to inhibit or stimulate functionality of the GPCR. In some embodiments, the candidate compound is a compound not known to be an agonist of the GPCR. In some embodiments, the candidate compound is a compound not known to be a partial agonist of the GPCR. In some embodiments, the candidate compound is a compound not known to be an inverse agonist of the GPCR. In some embodiments, the candidate compound is a compound not known to be an antagonist of the GPCR.

In some embodiments, the condition related to obesity is selected from the group consisting of hypertension, congestive cardiomyopathy, varicosities, pulmonary embolism, coronary heart disease, stroke, idiopathic intracranial hypertension, meralgia parethetica, dyspnea, obstructive sleep apnea, hypoventilation syndrome, Pickwickian syndrome, asthma, immobility, degenerative osteoarthritis, low back pain, striae distensae or "stretch marks," venous stasis of the lower extremities, lymphedema, cellulitis, intertrigo, carbuncles, acanthosis nigricans, skin tags, gastro-esophageal reflux disorder, nonalcoholic fatty liver/steatohepatitis, cholelithiasis, hernias, colon cancer, stress incontinence, obesity-related glomerulopathy, breast and uterine cancer, depression and low self-esteem, impaired quality of life, metabolic syndrome, insulin resistance, Type 2 diabetes, dyslipidemia, atherosclerosis, hyperandrogenemia in women, polycystic ovarian syndrome, dysmenorrhea, infertility, pregnancy complications, and male hypogonadism. In some embodiments, the condition related to obesity is selected from the group consisting of hypertension, insulin resistance, metabolic syndrome, Type 2 diabetes, dyslipidemia, atherosclerosis, coronary heart disease, and stroke.

In some embodiments, the screen is for an agonist of the GPCR. In some embodiments, the screen is for a partial agonist of the GPCR. In some embodiments, the screen is for an inverse agonist of the GPCR. In some embodiments, the screen is for an antagonist of the GPCR.

In some embodiments, the mammal is selected from the group consisting of mouse, rat, non-human primate, and human. In some embodiments, the mammal is a human.

Applicant reserves the right to exclude any one or more candidate compounds from any of the embodiments of the invention. Applicant reserves the right to exclude any one or more modulators from any of the embodiments of the invention. By way of example and not limitation, Applicant reserves the right to exclude any one or more inverse agonists or antagonists from any of the embodiments of the invention. Applicant reserves the right to exclude any polynucleotide or polypeptide from any of the embodiments of the invention. Applicant additionally reserves the right to exclude any condition related to obesity from any of the embodiments of the invention. It is also expressly contemplated that conditions related to obesity of the invention can be included in an embodiment either individually or in any combination. Applicant additionally reserves the right to exclude any disorder ameliorated by increasing body mass from any of the embodiments of the invention. It is also expressly contemplated that disorders ameliorated by increasing body mass of the invention can be included in an embodiment either individually or in any combination.

Without further elaboration, it is believed that one skilled in the art can, using the preceding description, practice the present invention to its fullest extent. The foregoing detailed description is given for clearness of understanding only, and no unnecessary limitation should be understood therefrom, as modifications within the scope of the invention may become apparent to those skilled in the art.

Throughout this application, various publications, patents and published patent applications are cited. The disclosures of these publications, patents and published patent applications referenced in this application are herein incorporated by reference in their entirety into the present disclosure. Citation herein by Applicant of a publication, patent, or published patent application is not an admission by Applicant of said publication, patent, or published patent application as prior art.

This application claims the benefit of priority from the following provisional patent application, filed via U.S. Express mail with the United States Patent and Trademark Office on the indicated date: U.S. Provisional Patent Application No. 60/735,346, filed Nov. 10, 2005. The disclosure of the foregoing provisional patent application is herein incorporated by reference in its entirety.

BRIEF DESCRIPTION OF THE DRAWINGS

FIG. 1 depicts results from a primary screen of candidate compounds against a "target receptor" which is a Gsα Fusion Protein construct of an endogenous, constitutively active Gs-coupled GPCR unrelated to GPR50. Results for "Compound A" are provided in well A2. Results for "Compound "B" are provided in well G9. (See, Example 6.)

FIG. 2. GPR50 exhibits detectable constitutive activity for lowering a level of intracellular cAMP. (See, Example 11.)

FIGS. 3A and 3B. Establishment of GPR50-knockout ("deficient") mice. A. Gene-targeting strategy for generating GPR50-knockout mice. B. Genotyping of GPR50-knockout mice (top panel) and wild-type mice (lower panel) by genomic PCR. (See, Example 12.)

FIGS. 6A and 6B. Analysis of co-expression of GPR50 by NPY neurons in the central part of the dorsomedial nucleus of the hypothalamus (DMHc) in rat. A. Representative photomicrographic image illustrating the expression of GPR50 and NPY in rat DMHc. B. Percentage of NPY neurons in rat DMHc co-expressing GPR50. (See, Example 17.)

FIGS. 7A-7C. Effect of food restriction on GPR50 expression in the central part of the dorsomedial nucleus of the hypothalamus (DMHc) in Sprague Dawley rats. A. Upper panel. Food intake in ad libitum fed and in food-restricted rats. Lower panel. Percentage original body weight in ad libitum fed and in food-restricted rats. B. Representative photomicrographic images illustrating expression of GPR50 in DMHc in ad libitum fed and in food-restricted rats. C. Relative levels of NPY mRNA (upper panel) and GPR50 mRNA (lower panel) in ad libitum fed and in food-restricted rats. (See, Example 20.)

DETAILED DESCRIPTION

Definitions

Figure 1:
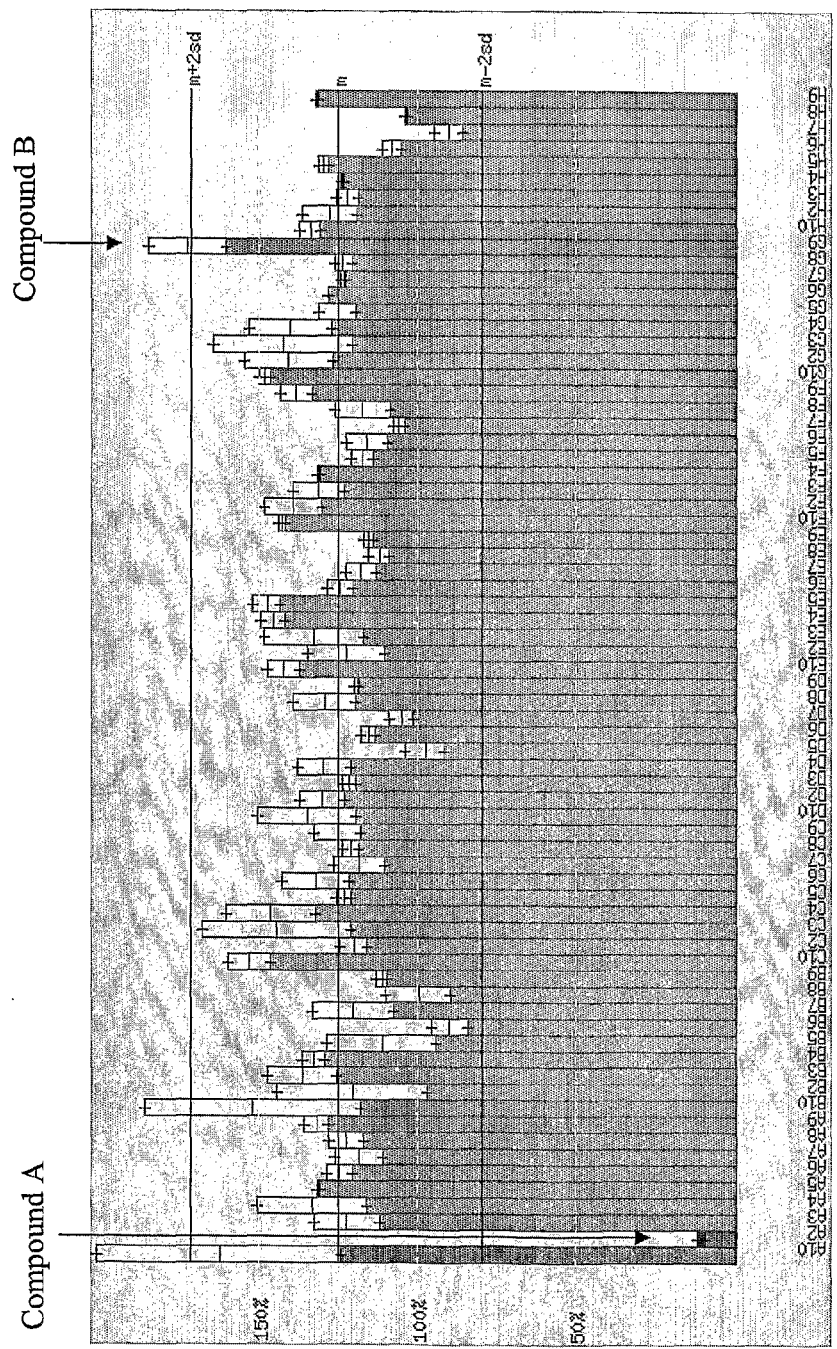
FIG. 1. By way of illustration and not limitation.

ADIPOSITY as used herein shall refer to body fat.

AGONIST shall mean an agent (e.g., ligand, candidate compound) that by virtue of binding to a GPCR activates the GPCR so as to elicit an intracellular response mediated by the GPCR.

AMINO ACID ABBREVIATIONS used herein are set out in Table B:

TABLE B

| ALANINE | ALA | A |
| --- | --- | --- |
| ARGININE | ARG | R |
| ASPARAGINE | ASN | N |
| ASPARTIC ACID | ASP | D |
| CYSTEINE | CYS | C |
| GLUTAMIC ACID | GLU | E |
| GLUTAMINE | GLN | Q |
| GLYCINE | GLY | G |
| HISTIDINE | HIS | H |
| ISOLEUCINE | ILE | I |
| LEUCINE | LEU | L |
| LYSINE | LYS | K |
| METHIONINE | MET | M |
| PHENYLALANINE | PHE | F |
| PROLINE | PRO | P |
| SERINE | SER | S |
| THREONINE | THR | T |
| TRYPTOPHAN | TRP | W |
| TYROSINE | TYR | Y |
| VALINE | VAL | V |

ANTAGONIST shall mean an agent (e.g., ligand, candidate compound) that binds, and preferably binds competitively, to a GPCR at about the same site as an agonist or partial agonist but which does not activate an intracellular response initiated by the active form of the GPCR, and can thereby inhibit the intracellular response by agonist or partial agonist. An antagonist typically does not diminish the baseline intracellular response in the absence of an agonist or partial agonist.

ANTIBODY is intended herein to encompass monoclonal antibody and polyclonal antibody. Antibodies of the present invention may be prepared by any suitable method known in the art.

BIOLOGICALLY ACTIVE FRAGMENT of a GPCR polypeptide or amino acid sequence shall mean a fragment of the polypeptide or amino acid sequence having structural and biochemical functions of a naturally occurring GPCR. In certain embodiments, the biologically active fragment couples to a G protein. In certain embodiments, the biologically active fragment binds to a ligand.

CANDIDATE COMPOUND shall mean a molecule (for example, and not limitation, a chemical compound) that is amenable to a screening technique and is used interchangeably herein with TEST COMPOUND.

CODON shall mean a grouping of three nucleotides (or equivalents to nucleotides) which generally comprise a nucleoside [adenosine (A), guanosine (G), cytidine (C), uridine (U) and thymidine (T)] coupled to a phosphate group and which, when translated, encodes an amino acid.

COMPOSITION means a material comprising at least one component.

COMPOUND EFFICACY or EFFICACY shall mean the ability of a compound to inhibit or stimulate one or more GPCR functions, e.g. by measurement of cAMP level in the presence or absence of a candidate compound. Exemplary means of measuring compound efficacy are disclosed in the Examples section of this patent document.

CONDITION RELATED TO OBESITY is intended to include but not be limited to hypertension, congestive cardiomyopathy, varicosities, pulmonary embolism, coronary heart disease, stroke, idiopathic intracranial hypertension, meralgia parethetica, dyspnea, obstructive sleep apnea, hypoventilation syndrome, Pickwickian syndrome, asthma, immobility, degenerative osteoarthritis, low back pain, striae distensae or "stretch marks," venous stasis of the lower extremities, lymphedema, cellulitis, intertrigo, carbuncles, acanthosis nigricans, skin tags, gastro-esophageal reflux disorder, nonalcoholic fatty liver/steatohepatitis, cholelithiasis, hernias, colon cancer, stress incontinence, obesity-related glomerulopathy, breast and uterine cancer, depression and low self-esteem, impaired quality of life, metabolic syndrome, insulin resistance, Type 2 diabetes, dyslipidemia, atherosclerosis, hyperandrogenemia in women, polycystic ovarian syndrome, dysmenorrhea, infertility, pregnancy complications, and male hypogonadism. In some embodiments, the condition related to obesity is selected from the group consisting of hypertension, insulin resistance, metabolic syndrome, Type 2 diabetes, dyslipidemia, atherosclerosis, coronary heart disease, and stroke.

CONSTITUTIVELY ACTIVE RECEPTOR shall mean a receptor stabilized in an active state by means other than through binding of the receptor to its ligand or a chemical equivalent thereof. A constitutively active receptor may be endogenous or non-endogenous.

CONSTITUTIVELY ACTIVATED RECEPTOR shall mean an endogenous receptor that has been modified so as to be constitutively active or to be more constitutively active.

CONSTITUTIVE RECEPTOR ACTIVATION shall mean activation of a receptor in the absence of binding to its ligand or a chemical equivalent thereof.

CONTACT or CONTACTING shall mean bringing at least two moieties together, whether in an in vitro system or an in vivo system.

DIRECTLY IDENTIFYING or DIRECTLY IDENTIFIED, in relationship to the phrase "candidate compound" or "test compound", shall mean the screening of a compound against a G protein-coupled receptor in the absence of a known ligand (e.g., a known agonist) to the G protein-coupled receptor.

DYSLIPIDEMIA as used herein refers to abnormal concentrations of serum lipids such as HDL (low), LDL (high), VLDL (high), triglycerides (high), lipoprotein (a) (high), free fatty acids (high) and other serum lipids, or combinations thereof.

ENDOGENOUS shall mean a material that a mammal naturally produces. Endogenous in reference to, for example and not limitation, the term "receptor," shall mean that which is naturally produced by a mammal (for example, and not limitation, a human). Endogenous shall be understood to encompass allelic variants of a gene as well as the allelic polypeptide variants so encoded. As used herein, "endogenous GPCR" and "native GPCR" are used interchangeably. By contrast, the term NON-ENDOGENOUS in this context shall mean that which is not naturally produced by a mammal (for example, and not limitation, a human).

EXPRESSION VECTOR shall mean a DNA sequence that is required for the transcription of cloned DNA and translation of the transcribed mRNA in an appropriate host cell recombinant for the expression vector. An appropriately constructed expression vector should contain an origin of replication for autonomous replication in host cells, selectable markers, a limited number of useful restriction enzyme sites, a potential for high copy number, and active promoters. The cloned DNA to be transcribed is operably linked to a constitutively or conditionally active promoter within the expression vector.

G PROTEIN-COUPLED RECEPTOR FUSION PROTEIN and GPCR FUSION PROTEIN, in the context of the invention disclosed herein, each mean a non-endogenous protein comprising an endogenous, constitutively active GPCR or a non-endogenous, constitutively activated GPCR fused to at least one G protein, most preferably the alpha ($\alpha$) subunit of such G protein (this being the subunit that binds GTP), with the G protein preferably being of the same type as the G protein that naturally couples with endogenous GPCR. In the preferred form, the G protein can be fused directly to the C-terminus of the GPCR or there may be spacers between the two.

HOST CELL shall mean a cell capable of having a vector incorporated therein. In the present context, the vector will typically contain nucleic acid encoding a GPCR or GPCR fusion protein in operable connection with a suitable promoter sequence to permit expression of the GPCR or GPCR fusion protein to occur.

IN NEED OF PREVENTION OR TREATMENT as used herein refers to a judgement made by a caregiver (e.g. physician, nurse, nurse practitioner, etc. in the case of humans; veterinarian in the case of animals, including non-human mammals) that a subject or animal requires or will benefit from treatment. This judgement is made based on a variety of factors that are in the realm of a caregiver's expertise, but that include the knowledge that the subject or animal is ill, or will be ill, as the result of a condition that is treatable by the compounds of the invention.

INHIBIT or INHIBITING, in relationship to the term "response" shall mean that a response is decreased or prevented in the presence of a compound as opposed to in the absence of the compound.

INVERSE AGONIST shall mean an agent (e.g., ligand, candidate compound) which binds to a GPCR and which inhibits the baseline intracellular response initiated by the active form of the receptor below the normal base level activity which is observed in the absence of an agonist or partial agonist.

LIGAND as used herein shall mean a molecule that specifically binds to a GPCR. An endogenous ligand is an endogenous molecule that binds to a native GPCR. A ligand of a GPCR may be, but is not limited to, an agonist, a partial agonist, an inverse agonist or an antagonist of the GPCR.

METABOLIC SYNDROME as defined herein, and according to the Adult Treatment Panel III (ATP III; National Institutes of Health: Third Report of the National Cholesterol Education Program Expert Panel on Detection, Evaluation, and Treatment of High Blood Cholesterol in Adults (Adult Treatment Panel III), Executive Summary; Bethesda, Md., National Institutes of Health, National Heart, Lung and Blood Institute, 2001 (NIH pub. No 01-3670), occurs when a person meets three or more of five criteria related to obesity, hypertriglyceridemia, low HDL cholesterol, high blood pressure, and high fasting glucose.

As used herein, the terms MODULATE or MODIFY are meant to refer to an increase or decrease in the amount, quality, or effect of a particular activity, function or molecule.

MODULATOR shall be understood to encompass agonist, partial agonist, inverse agonist and antagonist as hereinbefore defined.

OBESITY, as used herein, is defined as a body-mass index (BMI) of 30.0 or greater, in accordance with the WHO classifications of weight [Kopelman, Nature (2000) 404:635-643; the disclosure of which is herein incorporated by reference in its entirety]. In certain embodiments, obesity is defined on the basis of body fat content: greater than 25% in males and greater than 30% in females.

OVERWEIGHT, as used herein, is defined as a body mass index (BMI) of 27-29.9.

PARTIAL AGONIST shall mean an agent (e.g., ligand, candidate compound) that by virtue of binding to a GPCR activates the GPCR so as to elicit an intracellular response mediated by the GPCR, albeit to a lesser extent or degree than does a full agonist.

PHARMACEUTICAL COMPOSITION shall mean a composition comprising at least one active ingredient, whereby the composition is amenable to investigation for a specified, efficacious outcome in a mammal (for example, and not limited to a human). Those of ordinary skill in the art will understand and appreciate the techniques appropriate for determining whether an active ingredient has a desired efficacious outcome e.g., based upon the needs of the artisan.

POLYNUCLEOTIDE shall refer to RNA, DNA, or RNA/DNA hybrid sequence of more than one nucleotide in either single chain or duplex form. The polynucleotides of the invention may be prepared by any known method, including synthetic, recombinant, ex vivo generation, or a combination thereof, as well as utilizing any purification methods known in the art.

POLYPEPTIDE shall refer to a polymer of amino acids without regard to the length of the polymer. Thus, PEPTIDES, oligopeptides, and proteins are included within the definition of polypeptide. This term also does not specify or exclude post-expression modifications of polypeptides. For example, polypeptides that include the covalent attachment of glycosyl groups, acetyl groups, phosphate groups, lipid groups and the like are expressly encompassed by the term polypeptide.

PRIMER is used herein to denote a specific oligonucleotide sequence which is complementary to a target nucleotide sequence and used to hybridize to the target nucleotide sequence. A primer serves as an initiation point for nucleotide polymerization catalyzed by DNA polymerase, RNA polymerase, or reverse transcriptase.

RECEPTOR FUNCTIONALITY shall refer to the normal operation of a receptor to receive a stimulus and moderate an effect in the cell, including, but not limited to regulating gene transcription, regulating the influx or efflux of ions, effecting a catalytic reaction, and/or modulating activity through G-proteins, such as eliciting a second messenger response.

SECOND MESSENGER shall mean an intracellular response produced as a result of receptor activation. A second messenger can include, for example, inositol 1,4,5-triphosphate ($IP_3$), diacylglycerol (DAG), cyclic AMP (cAMP), cyclic GMP (cGMP), MAP kinase activity, MAPK/ERK kinase kinase-1 (MEKK1) activity, and $Ca^{2+}$. Second messenger response can be measured for a determination of receptor activation. In addition, second messenger response can be measured for the identification of candidate compounds as, for example, inverse agonists, partial agonists, agonists, and antagonists of the receptor.

SELECTIVE GPR50 MODULATOR, as used herein, refers to a modulator of GPR50 having selectivity for GPR50 receptor over one or more closely related receptors, such as melatonin receptor 1A (MTNR1A) or melatonin receptor 1B (MTNR1B).

SMALL MOLECULE shall be taken to mean a compound having a molecular weight of less than about 10,000 grams per mole, including a peptide, peptidomimetic, amino acid, amino acid analogue, polynucleotide, polynucleotide analogue, nucleotide, nucleotide analogue, organic compound or inorganic compound (i.e. including a heterorganic compound or organometallic compound), and salts, esters and other pharmaceutically acceptable forms thereof. In certain preferred embodiments, small molecules are organic or inorganic compounds having a molecular weight of less than about 5,000 grams per mole. In certain preferred embodiments, small molecules are organic or inorganic compounds having molecular weight of less than about 1,000 grams per mole. In certain preferred embodiments, small molecules are organic or inorganic compounds having a molecular weight of less than about 500 grams per mole.

STIMULATE or STIMULATING, in relationship to the term "response" shall mean that a response is increased in the presence of a compound as opposed to in the absence of the compound.

SUBJECT as used herein shall preferably refer to a mammal, including but not limited to a mouse, a rat, a rabbit, a pig, a dog, a cat, a non-human primate, a non-human mammal and a human, more preferably to a mouse or rat, most preferably to a human.

THERAPEUTICALLY EFFECTIVE AMOUNT as used herein refers to the amount of active compound or pharmaceutical agent that elicits the biological or medicinal response in a tissue, system, animal, subject or human that is being sought by a researcher, veterinarian, medical doctor or other clinician, which includes one or more of the following:

(1) Preventing the disease; for example, preventing a disease, condition or disorder in a subject that may be predisposed to the disease, condition or disorder but does not yet experience or display the pathology or symptomatology of the disease, (2) Inhibiting the disease; for example, inhibiting a disease, condition or disorder in a subject that is experiencing or displaying the pathology or symptomatology of the disease, condition or disorder (i.e., arresting further development of the pathology and/or symptomatology), and (3) Ameliorating the disease; for example, ameliorating a disease, condition or disorder in a subject that is experiencing or displaying the pathology or symptomatology of the disease, condition or disorder (i.e., reversing the pathology and/or symptomatology).

VARIANT as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. A typical variant of a polypeptide differs in amino acid sequence from another, reference polypeptide. A variant and reference polypeptide may differ in amino acid sequence by one or more substitutions, additions, deletions in any combination. A variant of a polynucleotide or polypeptide may be a naturally occurring one such as an ALLELIC VARIANT, or it may be a variant that is not known to occur naturally. Non-naturally occurring variants of polynucleotides and polypeptides may be made by mutagenesis techniques or by direct synthesis.

A. Introduction

The order of the following sections is set forth for presentational efficiency and is not intended, nor should be construed, as a limitation on the disclosure or the claims to follow.

B. Receptor Expression

1. GPCR Polypeptides of Interest

A GPCR of the invention may comprise an amino acid sequence selected from the group consisting of:

(a) the amino acid sequence of SEQ ID NO: 2;
(b) amino acids 2-617 of SEQ ID NO: 2;
(c) amino acids 2-617 of SEQ ID NO: 2, wherein the GPCR does not comprise amino acids 1-617 of SEQ ID NO: 2;
(d) the amino acid sequence of (a), (b) or (c), wherein SEQ ID NO: 2 comprises any combination of a substitution of serine at amino acid position 493 of SEQ ID NO: 2 with asparagine, a substitution of threonine at amino acid position 532 of SEQ ID NO: 2 with alanine, and a substitution of valine at amino acid position 606 of SEQ ID NO: 2 with isoleucine;
(e) the amino acid sequence of SEQ ID NO: 4;
(f) amino acids 2-613 of SEQ ID NO: 4;
(g) amino acids 2-613 of SEQ ID NO: 4, wherein the GPCR does not comprise amino acids 1-613 of SEQ ID NO: 4;
(h) the amino acid sequence of (i), (ii) or wherein SEQ ID NO: 4 comprises any combination of a substitution of asparagine at amino acid position 493 of SEQ ID NO: 4 with serine, a substitution of alanine at amino acid position 528 of SEQ ID NO: 4 with threonine, and a substitution of valine at amino acid position 602 of SEQ ID NO: 4 with isoleucine;
(i) the amino acid sequence of a G protein-coupled receptor encoded by a polynucleotide that is amplifiable by polymerase chain reaction (PCR) on a human DNA sample using specific primers SEQ ID NO: 9 and SEQ ID NO: 10;
(j) the amino acid sequence of a G protein-coupled receptor encoded by a polynucleotide hybridizing at high stringency to the complement of SEQ ID NO: 1 or SEQ ID NO: 3;
(k) the amino acid sequence of a G protein-coupled receptor having at least about 75%, at least about 80%, at least about 85%, at least about 90% or at least about 95% identity to SEQ ID NO: 2 or SEQ ID NO: 4;
(l) the amino acid sequence of SEQ ID NO: 6;
(m) amino acids 2-591 of SEQ ID NO: 6;
(n) amino acids 2-591 of SEQ ID NO: 6 wherein the GPCR does not comprise amino acids 1-591 of SEQ ID NO: 6;
(o) the amino acid sequence of a G protein-coupled receptor encoded by a polynucleotide hybridizing at high stringency to the complement of SEQ ID NO: 5;
(p) the amino acid sequence of a G protein-coupled receptor having at least about 75%, at least about 80%, at least about 85%, at least about 90% or at least about 95% identity to SEQ ID NO: 6;
(q) the amino acid sequence of SEQ ID NO: 8;
(r) amino acids 2-594 of SEQ ID NO: 8;
(s) amino acids 2-594 of SEQ ID NO: 8, wherein the GPCR does not comprise amino acids 1-594 of SEQ ID NO: 8;
(t) the amino acid sequence of a G protein-coupled receptor encoded by a polynucleotide hybridizing at high stringency to the complement of SEQ ID NO: 7;
(u) the amino acid sequence of a G protein-coupled receptor having at least about 75%, at least about 80%, at least about 85%, at least about 90% or at least about 95% identity to SEQ ID NO: 8; and
(v) the amino acid sequence of a G protein-coupled receptor that is a constitutively active version of a receptor having SEQ ID NO: 2 or SEQ ID NO: 4;

or a variant or biologically active fragment thereof.

In some embodiments, the GPCR comprises the amino acid sequence of a G protein-coupled receptor having at least about 75%, at least about 80%, at least about 85%, at least about 90% or at least about 95% identity to SEQ ID NO: 2 or SEQ ID NO: 4.

In some embodiments, the G protein-coupled receptor having at least about 75%, at least about 80%, at least about 85%, at least about 90% or at least about 95% identity to SEQ ID NO: 2, SEQ ID NO: 4, SEQ ID NO: 6 or SEQ ID NO: 8 is an endogenous GPCR. In some embodiments, the G protein-coupled receptor having at least about 75%, at least about 80%, at least about 85%, at least about 90% or at least about 95% identity to SEQ ID NO: 2, SEQ ID NO: 4, SEQ ID NO: 6 or SEQ ID NO: 8 is a mammalian endogenous GPCR. In some embodiments, the G protein-coupled receptor having at least about 75%, at least about 80%, at least about 85%, at least about 90% or at least about 95% identity to SEQ ID NO: 2, SEQ ID NO: 4, SEQ ID NO: 6 or SEQ ID NO: 8 is a non-endogenous GPCR.

In some embodiments, the G protein-coupled receptor that is a constitutively active version of a receptor having SEQ ID NO: 2 or SEQ ID NO: 4 is an endogenous G protein-coupled receptor. In some embodiments, the G protein-coupled receptor that is a constitutively active version of a receptor having SEQ ID NO: 2 or SEQ ID NO: 4 is a non-endogenous G protein-coupled receptor.

In some embodiments, the human DNA is human cDNA derived from a tissue or cell type that expresses GPR50. In some embodiments, the human cDNA is derived from hypothalamus. In some embodiments, the human cDNA is derived from pituitary.

In some embodiments, a GPCR of the invention is recombinant. In some embodiments, the recombinant GPCR is recombinant human GPR50.

In some embodiments, a GPCR of the invention is endogenous.

In some embodiments, a GPCR of the invention is non-endogenous.

In some embodiments, a GPCR of the invention is a mammalian GPR50.

In some embodiments, that is endogenous is a mammalian GPR50.

In some embodiments, a GPCR of the invention is constitutively active. In some embodiments, an endogenous GPCR of the invention is constitutively active. In some embodiments, a non-endogenous GPCR of the invention is constitutively active. In some embodiments, a mammalian GPR50 of the invention is constitutively active. In some embodiments, the mammalian GPR50 is human GPR50. In some embodiments, the human GPR50 is SEQ ID NO: 2 or an allele thereof. In some embodiments, the human GPR50 is SEQ ID NO: 4 or an allele thereof.

In some embodiments, a GPCR of the invention exhibits a detectable level of constitutive activity. In some embodiments, an endogenous GPCR of the invention exhibits a detectable level of constitutive activity. In some embodiments, a non-endogenous GPCR of the invention exhibits a detectable level of constitutive activity. In some embodiments, a mammalian GPR50 of the invention exhibits a detectable level of constitutive activity. In some embodiments, the mammalian GPR50 is human GPR50. In some embodiments, the human GPR50 is SEQ ID NO: 2 or an allele thereof. In some embodiments, the human GPR50 is SEQ ID NO: 4 or an allele thereof.

In some embodiments, a GPCR that may be used in the subject methods is a constitutively active version of a receptor having SEQ ID NO: 2. In some embodiments, the constitutively active version of a receptor having SEQ ID NO: 2 is an endogenous G protein-coupled receptor. In some embodiments, the constitutively active version of a receptor having SEQ ID NO: 2 is an endogenous G protein-coupled receptor having SEQ ID NO: 2. In some embodiments, the constitutively active version of a receptor having SEQ ID NO: 2 is a non-endogenous G protein-coupled receptor. In some embodiments, a GPCR that may be used in the subject methods is a constitutively active version of a receptor having SEQ ID NO: 4. In some embodiments, the constitutively active version of a receptor having SEQ ID NO: 4 is an endogenous G protein-coupled receptor. In some embodiments, the constitutively active version of a receptor having SEQ ID NO: 4 is an endogenous G protein-coupled receptor having SEQ ID NO: 4. In some embodiments, the constitutively active version of a receptor having SEQ ID NO: 4 is a non-endogenous G protein-coupled receptor.

By way of illustration and not limitation, deletion of an N-terminal methionine residue or an N-terminal signal peptide is envisioned to provide a biologically active fragment that may be used in the subject invention. In some embodiments, a biologically active fragment of the invention is a fragment that exhibits a detectable level of constitutive activity. In some embodiments, the constitutive activity is for lowering a level of intracellular cAMP. In some embodiments, the constitutive activity is for causing melanophore cells to undergo pigment aggregation. In certain embodiments, a biologically active fragment of the invention is a fragment that specifically binds an antibody that recognizes a mammalian endogenous GPR50 (an antibody that recognizes an endogenous mammalian GPR50 can be obtained commercially from, e.g., Advanced Targeting Systems, San Diego, Calif.; and CHEMICON International, Inc., Temecula, Calif.) or specifically binds a known ligand of a mammalian endogenous GPR50. In certain embodiments, the known ligand of the mammalian endogenous GPR50 is an endogenous ligand of the mammalian endogenous GPR50.

An allelic variant of human GPR50 of SEQ ID NO: 2 or SEQ ID NO: 4, of mouse GPR50 of SEQ ID NO: 6, or of rat GPR50 of SEQ ID NO: 8 is envisioned to be within the scope of the invention. In some embodiments, a GPCR that may be used in the subject methods may comprise an allelic variant of SEQ ID NO: 2 or SEQ ID NO: 4.

A variant which is a mammalian ortholog of human GPR50 of SEQ ID NO: 2 or SEQ ID NO: 4 is envisioned to be within the scope of the invention. By way of illustration and not limitation, additional to mouse GPR50 and rat GPR50, sheep GPR50 (GenBank® Accession No. NP_001009726), chimpanzee GPR50 (GenBank® Accession No. XP_001136005), and rhesus monkey GPR50 (GenBank® Accession No. XP_001092026) are envisioned to be within the scope of the invention.

In certain embodiments, a variant GPCR that may be used in the subject methods is a GPCR derived from SEQ ID NO: 2, SEQ ID NO: 4, SEQ ID NO: 6 or SEQ ID NO: 8 by substitution, deletion or addition of one or several amino acids in the amino acid sequence of SEQ ID NO: 2, SEQ ID NO: 4, SEQ ID NO: 6 or SEQ ID NO: 8, respectively.

In certain embodiments, a variant GPCR that may be used in the subject methods is a GPCR derived from SEQ ID NO: 2, SEQ ID NO: 4, SEQ ID NO: 6 or SEQ ID NO: 8 by no more than 10 conservative amino acid substitutions and/or no more than 3 non-conservative amino acid substitutions in the amino acid sequence of SEQ ID NO: 2, SEQ ID NO: 4, SEQ ID NO: 6 or SEQ ID NO: 8, respectively. In certain embodiments, arginine, lysine and histidine may conservatively substitute for each other; glutamic acid and aspartic acid may conservatively substitute for each other; glutamine and asparagine may conservatively substitute for each other; leucine, isoleucine and valine may conservatively substitute for each other; phenylalanine, tryptophan and tyrosine may conservatively substitute for each other; and glycine, alanine, serine, threonine and methionine may conservatively substitute for each other. The amino acid substitutions, amino acid deletions, and amino acid additions may be at any position (e.g., the C- or N-terminus, or at internal positions).

A variant of SEQ ID NO: 2, SEQ ID NO: 4, SEQ ID NO: 6 or SEQ ID NO: 8 having at least about 75%, at least about 80%, at least about 85%, at least about 90%, at least about 95%, at least about 96%, at least about 97%, at least about 98%, at least about 99%, at least about 99.1%, at least about 99.2%, at least about 99.3%, at least about 99.4%, at least about 99.5%, at least about 99.6%, at least about 99.7%, at least about 99.8%, or at least about 99.9% identity to SEQ ID NO: 2, SEQ ID NO: 4, SEQ ID NO: 6 or SEQ ID NO: 8, respectively, is envisioned to be within the scope of the invention. In some embodiments, said variant is a variant of SEQ ID NO: 2. In some embodiments, said variant is a variant of SEQ ID NO: 4. In some embodiments, the variant which is a variant of SEQ ID NO: 2, SEQ ID NO: 4, SEQ ID NO: 6 or SEQ ID NO: 8 is a GPCR. In some embodiments, the variant which is a variant of SEQ ID NO: 2, SEQ ID NO: 4, SEQ ID NO: 6 or SEQ ID NO: 8 is an endogenous GPCR. In some embodiments, the variant that is an endogenous GPCR is a mammalian GPCR. In some embodiments, the variant which is a variant of SEQ ID NO: 2, SEQ ID NO: 4, SEQ ID NO: 6 or SEQ ID NO: 8 is an non-endogenous GPCR. In some embodiments, the variant which is a variant of SEQ ID NO: 2, SEQ ID NO: 4, SEQ ID NO: 6 or SEQ ID NO: 8 exhibits a detectable level of constitutive activity. In some embodiments, the constitutive activity is for lowering a level of intracellular cAMP. In some embodiments, the constitutive activity is for causing melanophore cells to undergo pigment aggregation. In certain embodiments, the variant which is a variant of SEQ ID NO: 2, SEQ ID NO: 4, SEQ ID NO: 6 or SEQ ID NO: 8 specifically binds an antibody that recognizes an mammalian endogenous GPR50 (an antibody that recognizes an endogenous mammalian GPR50 can be obtained commercially from, e.g., Advanced Targeting Systems, San Diego, Calif.; and CHEMICON International, Inc., Temecula, Calif.) or specifically binds a known ligand of an mammalian endogenous GPR50. In certain embodiments, the known ligand of the mammalian endogenous GPR50 is an endogenous ligand of the mammalian endogenous GPR50. Percent identity can be determined conventionally using known computer programs.

In certain embodiments, a variant GPCR that may be used in the subject methods has an amino acid sequence having at least about 75%, at least about 80%, at least about 85%, at least about 90%, at least about 95%, of at least about 96%, at least about 97%, at least about 98%, at least about 99%, at least about 99.1%, at least about 99.2%, at least about 99.3%, at least about 99.4%, at least about 99.5%, at least about 99.6%, at least about 99.7%, at least about 99.8%, or at least about 99.9% identity to SEQ ID NO: 2 or SEQ ID NO: 4. By a variant GPCR having, for example, 95% "identity" to SEQ ID NO: 2 is meant that the amino acid sequence of the variant is identical to amino acids 1-617 of SEQ ID NO: 2 except that it may include up to five amino acid alterations per each 100 amino acids of SEQ ID NO: 2. Thus, to obtain for example an amino acid sequence having at least 95% identity to the amino acid sequence of SEQ ID NO: 2, up to 5% (5 of 100) of the amino acid residues in the sequence may be inserted, deleted, or substituted with another amino acid compared with amino acids 1-617 of SEQ ID NO: 2. By a variant GPCR having, for example, 95% "identity" to SEQ ID NO: 4 is meant that the amino acid sequence of the variant is identical to amino acids 1-613 of SEQ ID NO: 4 except that it may include up to five amino acid alterations per each 100 amino acids of SEQ ID NO: 4. Thus, to obtain for example an amino acid sequence having at least 95% identity to the amino acid sequence of SEQ ID NO: 4, up to 5% (5 of 100) of the amino acid residues in the sequence may be inserted, deleted, or substituted with another amino acid compared with amino acids 1-613 of SEQ ID NO: 4. These alternations may occur at the amino or carboxy termini or anywhere between those terminal positions, interspersed either subjectly among residues in the sequence or in one or more contiguous groups within the sequence.

In some embodiments, a variant GPCR that may be used in the subject methods is a GPCR encoded by a polynucleotide hybridizing at high stringency to the complement of SEQ ID NO: 1, SEQ ID NO: 3, SEQ ID NO: 5 or SEQ ID NO: 7. In some embodiments, the polynucleotide hybridizes at high stringency to the complement of SEQ ID NO: 1 or SEQ ID NO: 3. In some embodiments, the variant is an endogenous GPCR. In some embodiments, the variant that is an endogenous GPCR is a mammalian GPCR. In some embodiments, the variant exhibits a detectable level of constitutive activity. In some embodiments, the constitutive activity is for lowering a level of intracellular cAMP. In some embodiments, the constitutive activity is for causing melanophore cells to undergo pigment aggregation. In certain embodiments, the G protein-coupled receptor encoded by a polynucleotide hybridizing at high stringency to the complement of SEQ ID NO: 1, SEQ ID NO: 3, SEQ ID NO: 5 or SEQ ID NO: 7 specifically binds an antibody that recognizes an mammalian endogenous GPR50 (an antibody that recognizes an endogenous mammalian GPR50 can be obtained commercially from, e.g., Advanced Targeting Systems, San Diego, Calif.; and CHEMICON International, Inc., Temecula, Calif.) or specifically binds a known ligand of an mammalian endogenous GPR50. In certain embodiments, the known ligand of the mammalian endogenous GPR50 is an endogenous ligand of the mammalian endogenous GPR50. Hybridization techniques are well known to the skilled artisan. In some embodiments, stringent hybridization conditions include overnight incubation at 42° C. in a solution comprising: 50% formamide, 5×SSC (1×SSC=150 mM NaCl, 15 mM trisodium citrate), 50 mM sodium phosphate (pH 7.6), 5×Denhardt's solution, 10% dextran sulfate, and 20 µg/ml denatured, sheared salmon sperm DNA; followed by washing the filter in 0.1× SSC at about 50° C., at about 55° C., at about 60° C. or at about 65° C.

a. Sequence Identity

In certain embodiments, percent identity is evaluated using the Basic Local Alignment Search Tool ("BLAST"), which is well known in the art [See, e.g., Karlin and Altschul, Proc Natl Acad Sci USA (1990) 87:2264-2268; Altschul et al., J Mol Biol (1990) 215:403-410; Altschul et al, Nature Genetics (1993) 3:266-272; and Altschul et al., Nucleic Acids Res (1997) 25:3389-3402; the disclosure of each of which is herein incorporated by reference in its entirety]. The BLAST programs may be used with the default parameters or with modified parameters provided by the user. Preferably, the parameters are default parameters.

A preferred method for determining the best overall match between a query sequence (e.g., the amino acid sequence of SEQ ID NO:2) and a sequence to be interrogated, also referred to as a global sequence alignment, can be determined using the FASTDB computer program based on the algorithm of Brutlag et al. [Comp App Biosci (1990) 6:237-245; the disclosure of which is herein incorporated by reference in its entirety]. In a sequence alignment the query and interrogated sequences are both amino acid sequences. The results of said global sequence alignment is in percent identity. Preferred parameters used in a FASTDB amino acid alignment are: Matrix=PAM 0, k-tuple=2, Mismatch Penalty=1, Joining Penalty=20, Randomization Group-25, Length-0, Cutoff Score=1, Window Size=sequence length, Gap Penalty=5, Gap Size Penalty=0.05, Window Size=247 or the length of the interrogated amino acid sequence, whichever is shorter.

If the interrogated sequence is shorter than the query sequence due to N- or C-terminal deletions, not because of internal deletions, the results, in percent identity, must be manually corrected because the FASTDB program does not account for N- and C-terminal truncations of the interrogated sequence when calculating global percent identity. For interrogated sequences truncated at the N- and C-termini, relative to the query sequence, the percent identity is corrected by calculating the number of residues of the query sequence that are N- and C-terminal of the interrogated sequence, that are not matched/aligned with a corresponding interrogated sequence residue, as a percent of the total bses of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues to the N- and C-termini of the interrogated sequence, which are not matched/aligned with the query sequence, are considered for the purposes of manually adjusting the percent identity score. That is, only query amino acid residues outside the farthest N- and C-terminal residues of the interrogated sequence.

For example, a 90 amino acid residue interrogated sequence is aligned with a 100-residue query sequence to determine percent identity. The deletion occurs at the N-terminus of the interrogated sequence and therefore, the FASTDB alignment does not match/align with the first residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched, the final percent identity would be 90%.

In another example, a 90-residue interrogated sequence is compared with a 100-residue query sequence. This time the deletions are internal so there are no residues at the N- or C-termini of the interrogated sequence, which are not matched/aligned with the query. In this case, the percent identity calculated by FASTDB is not manually corrected. Once again, only residue positions outside the N- and C-terminal ends of the subject sequence, as displayed in the FASTDB alignment, which are not matched/aligned with the query sequence are manually corrected. No other corrections are made for the purposes of the present invention.

b. Fusion Proteins

In certain embodiments, a polypeptide of interest is a fusion protein, and may contain, for example, an affinity tag domain or a reporter domain. Suitable affinity tags include any amino acid sequence that may be specifically bound to another moiety, usually another polypeptide, most usually an antibody. Suitable affinity tags include epitope tags, for example, the V5 tag, the FLAG tag, the HA tag (from hemagglutinin influenza virus), the myc tag, and the like, as is known in the art. Suitable affinity tags also include domains for which, binding substrates are known, e.g., HIS, GST and MBP tags, as is known in the art, and domains from other proteins for which specific binding partners, e.g., antibodies, particularly monoclonal antibodies, are available. Suitable affinity tags also include any protein-protein interaction domain, such as a IgG Fc region, which may be specifically bound and detected using a suitable binding partner, e.g. the IgG Fc receptor. It is expressly contemplated that such a fusion protein may contain a heterologous N-terminal domain (e.g., an epitope tag) fused in-frame with a GPCR that has had its N-terminal methionine residue either deleted or substituted with an alternative amino acid.

Suitable reporter domains include any domain that can report the presence of a polypeptide. While it is recognized that an affinity tag may be used to report the presence of a polypeptide using, e.g., a labeled antibody that specifically binds to the tag, light emitting reporter domains are more usually used. Suitable light emitting reporter domains include luciferase (from, e.g., firefly, *Vargula*, *Renilla reniformis* or *Renilla muelleri*), or light emitting variants thereof. Other suitable reporter domains include fluorescent proteins, (from e.g., jellyfish, corals and other coelenterates as such those from *Aequoria*, *Renilla*, *Ptilosarcus*, *Stylatula* species), or light emitting variants thereof. Light emitting variants of these reporter proteins are very well known in the art and may be brighter, dimmer, or have different excitation and/or emission spectra, as compared to a native reporter protein. For example, some variants are altered such that they no longer appear green, and may appear blue, cyan, yellow, enhanced yellow red (termed BFP, CFP, YFP eYFP and RFP, respectively) or have other emission spectra, as is known in the art. Other suitable reporter domains include domains that can report the presence of a polypeptide through a biochemical or color change, such as β-galactosidase, β-glucuronidase, chloramphenicol acetyl transferase, and secreted embryonic alkaline phosphatase.

Also as is known in the art, an affinity tags or a reporter domain may be present at any position in a polypeptide of interest. However, in most embodiments, they are present at the C- or N-terminal end of a polypeptide of interest.

2. Nucleic Acids Encoding GPCR Polypeptides of Interest

Since the genetic code and recombinant techniques for manipulating nucleic acid are known, and the amino acid sequences of GPCR polypeptides of interest described as above, the design and production of nucleic acids encoding a GPCR polypeptide of interest is well within the skill of an artisan. In certain embodiments, standard recombinant DNA technology (Ausubel, et al, *Short Protocols in Molecular Biology*, 3rd ed., Wiley & Sons, 1995; Sambrook, et al., *Molecular Cloning: A Laboratory Manual*, Second Edition, (1989) Cold Spring Harbor, N.Y.) methods are used. For example, GPCR coding sequences may be isolated from a library of GPCR coding sequence using any one or a combination of a variety of recombinant methods that do not need to be described herein. Subsequent substitution, deletion, and/or addition of nucleotides in the nucleic acid sequence encoding a protein may also be done using standard recombinant DNA techniques.

For example, site directed mutagenesis and subcloning may be used to introduce/delete/substitute nucleic acid residues in a polynucleotide encoding a polypeptide of interest. In other embodiments, PCR may be used. Nucleic acids encoding a polypeptide of interest may also be made by chemical synthesis entirely from oligonucleotides (e.g., Cello et al., Science (2002) 297:1016-8).

In some embodiments, the codons of the nucleic acids encoding polypeptides of interest are optimized for expression in cells of a particular species, particularly a mammalian, e.g., mouse, rat, hamster, non-human primate, or human, species. In some embodiments, the codons of the nucleic acids encoding polypeptides of interest are optimized for expression in cells of a particular species, particularly an amphibian species.

a. Vectors

The invention further provides vectors (also referred to as "constructs") comprising a subject nucleic acid. In many embodiments of the invention, the subject nucleic acid sequences will be expressed in a host after the sequences have been operably linked to an expression control sequence, including, e.g. a promoter. The subject nucleic acids are also typically placed in an expression vector that can replicate in a host cell either as an episome or as an integral part of the host chromosomal DNA. Commonly, expression vectors will contain selection markers, e.g., tetracycline or neomycin, to permit detection of those cells transformed with the desired DNA sequences (see, e.g., U.S. Pat. No. 4,704,362, which is incorporated herein by reference). Vectors, including single and dual expression cassette vectors are well known in the art (Ausubel, et al, *Short Protocols in Molecular Biology*, 3rd ed., Wiley & Sons, 1995; Sambrook, et al., *Molecular Cloning: A Laboratory Manual*, Second Edition, (1989) Cold Spring Harbor, N.Y.). Suitable vectors include viral vectors, plasmids, cosmids, artificial chromosomes (human artificial chromosomes, bacterial artificial chromosomes, yeast artificial chromosomes, etc.), mini-chromosomes, and the like. Retroviral, adenoviral and adeno-associated viral vectors may be used.

A variety of expression vectors are available to those in the art for purposes of producing a polypeptide of interest in a cell and include expression vectors which are commercially available (e.g., from Invitrogen, Carlsbad, Calif.; Clontech, Mountain View, Calif.; Stratagene, La Jolla, Calif.). Commercially available expression vectors include, by way of non-limiting example, CMV promoter-based vectors. One suitable expression vector is pCMV. The expression vector may be adenoviral. An exemplary adenoviral vector may be purchased as AdEasy™ from Qbiogene (Carlsbad, Calif.) [He TC et al, Proc Natl Acad Sci USA (1998) 95:2509-2514; and U.S. Pat. No. 5,922,576; the disclosure of each of which is herein incorporated by reference in its entirety]. Other suitable expression vectors will be readily apparent to those of ordinary skill in the art.

The subject nucleic acids usually comprise an single open reading frame encoding a subject polypeptide of interest, however, in certain embodiments, since the host cell for expression of the polypeptide of interest may be a eukaryotic cell, e.g., a mammalian cell, such as a human cell, the open reading frame may be interrupted by introns. Subject nucleic acid are typically part of a transcriptional unit which may contain, in addition to the subject nucleic acid 3' and 5' untranslated regions (UTRs) which may direct RNA stability, translational efficiency, etc. The subject nucleic acid may also be part of an expression cassette which contains, in addition to the subject nucleic acid a promoter, which directs the transcription and expression of a polypeptide of interest, and a transcriptional terminator.

Eukaryotic promoters can be any promoter that is functional in a eukaryotic host cell, including viral promoters and promoters derived from eukaryotic genes. Exemplary eukaryotic promoters include, but are not limited to, the following: the promoter of the mouse metallothionein I gene sequence (Hamer et al., J. Mol. Appl. Gen. 1:273-288, 1982); the TK promoter of Herpes virus (McKnight, Cell 31:355-365, 1982); the SV40 early promoter (Benoist et al., Nature (London) 290:304-310, 1981); the yeast gall gene sequence promoter (Johnston et al., Proc. Natl. Acad. Sci. (USA) 79:6971-6975, 1982); Silver et al., Proc. Natl. Acad. Sci. (USA) 81:5951-59SS, 1984), the CMV promoter, the EF-1 promoter, Ecdysone-responsive promoter(s), tetracycline-responsive promoter, and the like. Viral promoters may be of particular interest as they are generally particularly strong promoters. In certain embodiments, a promoter is used that is a promoter of the target pathogen. Promoters for use in the present invention are selected such that they are functional in the cell type (and/or animal) into which they are being introduced. In certain embodiments, the promoter is a CMV promoter.

In certain embodiments, a subject vector may also provide for expression of a selectable marker. Suitable vectors and selectable markers are well known in the art and discussed in Ausubel, et al, (Short Protocols in Molecular Biology, 3rd ed., Wiley & Sons, 1995) and Sambrook, et al, (Molecular Cloning: A Laboratory Manual, Third Edition, (2001) Cold Spring Harbor, N.Y.). A variety of different genes have been employed as selectable markers, and the particular gene employed in the subject vectors as a selectable marker is chosen primarily as a matter of convenience. Known selectable marker genes include: the thymidine kinase gene, the dihydrofolate reductase gene, the xanthine-guanine phosphoribosyl transferase gene, CAD, the adenosine deaminase gene, the asparagine synthetase gene, the antibiotic resistance genes, e.g. tetr, ampr, Cmr or cat, kanr or neor (aminoglycoside phosphotransferase genes), the hygromycin B phosphotransferase gene, and the like.

As mentioned above, polypeptides of interest may be fusion proteins that contain an affinity domain and/or a reporter domain. Methods for making fusions between a reporter or tag and a GPCR, for example, at the C- or N-terminus of the GPCR, are well within the skill of one of skill in the art (e.g. McLean et al, Mol. Pharma. Mol. Pharmacol. 1999 56:1182-91; Ramsay et al., Br. J. Pharmacology, 2001, 315-323) and will not be described any further. It is expressly contemplated that such a fusion protein may contain a heterologous N-terminal domain (e.g., an epitope tag) fused in-frame with a GPCR that has had its N-terminal methionine residue either deleted or substituted with an alternative amino acid. It is appreciated that a polypeptide of interest may first be made from a native polypeptide and then operably linked to a suitable reporter/tag as described above.

The subject nucleic acids may also contain restriction sites, multiple cloning sites, primer binding sites, ligatable ends, recombination sites etc., usually in order to facilitate the construction of a nucleic acid encoding a polypeptide of interest.

b. Host Cells

The invention further provides host cells comprising a vector comprising a subject nucleic acid. Suitable host cells include prokaryotic, e.g., bacterial cells (for example *E. coli*), as well as eukaryotic cells e.g. an animal cell (for example an insect, mammal, fish, amphibian, bird or reptile cell), a plant cell (for example a maize or *Arabidopsis* cell), or a fungal cell (for example a *S. cerevisiae* cell). In certain embodiments, any cell suitable for expression of a polypeptide of interest-encoding nucleic acid may be used as a host cell. Usually, an animal host cell line is used, examples of which are as follows: monkey kidney cells (COS cells), monkey kidney CVI cells transformed by SV40 (COS-7, ATCC CRL 165 1); human embryonic kidney cells (HEK-293 ["293"], Graham et al. J. Gen Virol. 36:59 (1977)); HEK-293T ["293T"] cells; baby hamster kidney cells (BHK, ATCC CCL 10); chinese hamster ovary-cells (CHO, Urlaub and Chasin, Proc. Natl. Acad. Sci. (USA) 77:4216, (1980); Syrian golden hamster cells MCB3901 (ATCC CRL-9595); mouse sertoli cells (TM4, Mather, Biol. Reprod. 23:243-251 (1980)); monkey kidney cells (CVI ATCC CCL 70); african green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (hep G2, HB 8065); mouse mammary tumor (MMT 060562, ATCC CCL 51); TR1 cells (Mather et al., Annals N.Y. Acad. Sci. 383:44-68 (1982)); NIH/3T3 cells (ATCC CRL-1658); and mouse L cells (ATCC CCL-1).

In certain embodiments, melanophores are used. Melanophores are skin cells found in lower vertebrates. Relevant materials and methods will be followed according to the disclosure of U.S. Pat. No. 5,462,856 and U.S. Pat. No. 6,051,386. These patent disclosures are herein incorporated by reference in their entirety.

Additional cell lines will become apparent to those of ordinary skill in the art, and a wide variety of cell lines are available from the American Type Culture Collection, 10801 University Boulevard, Manassas, Va. 20110-2209.

C. Screening of Candidate Compounds

1. Generic GPCR Screening Assay Techniques

When a G protein receptor becomes active, it binds to a G protein (e.g., Gq, Gs, Gi, Gz, Go) and stimulates the binding of GTP to the G protein. The G protein then acts as a GTPase and slowly hydrolyzes the GTP to GDP, whereby the receptor, under normal conditions, becomes deactivated. However, activated receptors continue to exchange GDP to GTP. A non-hydrolyzable analog of GTP, [$^{35}$S]GTPγS, can be used to monitor enhanced binding to membranes which express activated receptors. It is reported that [$^{35}$S]GTPγS can be used to monitor G protein coupling to membranes in the absence and presence of ligand. An example of this monitoring, among other examples well-known and available to those in the art, was reported by Traynor and Nahorski in 1995. A preferred use of this assay system is for initial screening of candidate compounds because the system is generically applicable to all G protein-coupled receptors regardless of the particular G protein that interacts with the intracellular domain of the receptor.

2. Specific GPCR Screening Assay Techniques

Once candidate compounds are identified using the "generic" G protein-coupled receptor assay (i.e., an assay to select compounds that are agonists or inverse agonists), in some embodiments further screening to confirm that the compounds have interacted at the receptor site is preferred. For example, a compound identified by the "generic" assay may not bind to the receptor, but may instead merely "uncouple" the G protein from the intracellular domain.

a. Gs, Gz and Gi.

Gs stimulates the enzyme adenylyl cyclase. Gi (and Gz and Go), on the other hand, inhibit adenylyl cyclase. Adenylyl cyclase catalyzes the conversion of ATP to cAMP; thus, activated GPCRs that couple the Gs protein are associated with increased cellular levels of cAMP. On the other hand, activated GPCRs that couple Gi (or Gz, Go) protein are associated with decreased cellular levels of cAMP. See, generally, "Indirect Mechanisms of Synaptic Transmission," Chpt. 8, *From Neuron To Brain* ($3^{rd}$ Ed.) Nichols, J. G. et al eds. Sinauer Associates, Inc. (1992). Thus, assays that detect cAMP can be utilized to determine if a candidate compound is, e.g., an inverse agonist to the receptor (i.e., such a compound would decrease the levels of cAMP). A variety of approaches known in the art for measuring cAMP can be utilized; in some embodiments a preferred approach relies upon the use of anti-cAMP antibodies in an ELISA-based format. Another type of assay that can be utilized is a whole cell second messenger reporter system assay. Promoters on genes drive the expression of the proteins that a particular gene encodes. Cyclic AMP drives gene expression by promoting the binding of a cAMP-responsive DNA binding protein or transcription factor (CREB) that then binds to the promoter at specific sites called cAMP response elements and drives the expression of the gene. Reporter systems can be constructed which have a promoter containing multiple cAMP response elements before the reporter gene, e.g., β-galactosidase or luciferase. Thus, an activated Gs-linked receptor causes the accumulation of cAMP that then activates the gene and expression of the reporter protein. The reporter protein such as β-galactosidase or luciferase can then be detected using standard biochemical assays (Chen et al. 1995).

b. Go and Gq.

Gq and Go are associated with activation of the enzyme phospholipase C, which in turn hydrolyzes the phospholipid $PIP_2$, releasing two intracellular messengers: diacyclglycerol (DAG) and inositol 1,4,5-triphosphate ($IP_3$). Increased accumulation of $IP_3$ is associated with activation of Gq- and Go-associated receptors. See, generally, "Indirect Mechanisms of Synaptic Transmission," Chpt. 8, *From Neuron To Brain* ($3^{rd}$ Ed.) Nichols, J. G. et al eds. Sinauer Associates, Inc. (1992). Assays that detect $IP_3$ accumulation can be utilized to determine if a candidate compound is, e.g., an inverse agonist to a Gq- or Go-associated receptor (i.e., such a compound would decrease the levels of $IP_3$). Gq-associated receptors can also been examined using an AP1 reporter assay in that Gq-dependent phospholipase C causes activation of genes containing AP1 elements; thus, activated Gq-associated receptors will evidence an increase in the expression of such genes, whereby inverse agonists thereto will evidence a decrease in such expression, and agonists will evidence an increase in such expression. Commercially available assays for such detection are available.

3. GPCR Fusion Protein

The use of an endogenous, constitutively active GPCR or a non-endogenous, constitutively activated GPCR, for use in screening of candidate compounds for the direct identification of inverse agonists or agonists provides an interesting screening challenge in that, by definition, the receptor is active even in the absence of an endogenous ligand bound thereto. Thus, in order to differentiate between, e.g., the non-endogenous receptor in the presence of a candidate compound and the non-endogenous receptor in the absence of that compound, with an aim of such a differentiation to allow for an understanding as to whether such compound may be an inverse agonist or agonist or have no affect on such a receptor, in some embodiments it is preferred that an approach be utilized that can enhance such differentiation. In some embodiments, a preferred approach is the use of a GPCR Fusion Protein.

Generally, once it is determined that a non-endogenous GPCR has been constitutively activated using the assay techniques set forth above (as well as others known to the art-skilled), it is possible to determine the predominant G protein that couples with the endogenous GPCR. Coupling of the G protein to the GPCR provides a signaling pathway that can be assessed. In some embodiments it is preferred that screening take place using a mammalian or a melanophore expression system, as such a system will be expected to have endogenous G protein therein. Thus, by definition, in such a system, the non-endogenous, constitutively activated GPCR will continuously signal. In some embodiments it is preferred that this signal be enhanced such that in the presence of, e.g., an inverse agonist to the receptor, it is more likely that it will be able to more readily differentiate, particularly in the context of screening, between the receptor when it is contacted with the inverse agonist.

The GPCR Fusion Protein is intended to enhance the efficacy of G protein coupling with the GPCR. The GPCR Fusion Protein may be preferred for screening with either an endogenous, constitutively active GPCR or a non-endogenous, constitutively activated GPCR because such an approach increases the signal that is generated in such screening techniques. This is important in facilitating a significant "signal to noise" ratio; such a significant ratio is preferred for the screening of candidate compounds as disclosed herein.

The construction of a construct useful for expression of a GPCR Fusion Protein is within the purview of those having ordinary skill in the art. Commercially available expression vectors and systems offer a variety of approaches that can fit the particular needs of an investigator. Important criteria in the construction of such a GPCR Fusion Protein construct include but are not limited to, that the GPCR sequence and the G protein sequence both be in-frame (preferably, the sequence for the endogenous GPCR is upstream of the G protein sequence), and that the "stop" codon of the GPCR be deleted or replaced such that upon expression of the GPCR, the G protein can also be expressed. The GPCR can be linked directly to the G protein, or there can be spacer residues between the two (preferably, no more than about 12, although this number can be readily ascertained by one of ordinary skill in the art). Based upon convenience, it is preferred to use a spacer. In some embodiments, it is preferred that the G protein that couples to the non-endogenous GPCR will have been identified prior to the creation of the GPCR Fusion Protein construct. Because there are only a few G proteins that have been identified, it is preferred that a construct comprising the sequence of the G protein (i.e., a universal G protein construct, see Example 4(a) below) be available for insertion of a GPCR sequence therein; this provides for further efficiency in the context of large-scale screening of a variety of different GPCRs having different sequences.

As noted above, activated GPCRs that couple to Gi, Gz and Go are expected to inhibit the formation of cAMP making assays based upon these types of GPCRs challenging [i.e., the cAMP signal decreases upon activation, thus making the direct identification of, e.g., agonists (which would further decrease this signal) challenging]. As will be disclosed herein, it has been ascertained that for these types of receptors, it is possible to create a GPCR Fusion Protein that is not based upon the GPCR's endogenous G protein, in an effort to establish a viable cyclase-based assay. Thus, for example, an endogenous Gi coupled receptor can be fused to a Gs protein—such a fusion construct, upon expression, "drives" or "forces" the endogenous GPCR to couple with, e.g., Gs rather than the "natural" Gi protein, such that a cyclase-based assay can be established. Thus, for Gi, Gz and Go coupled receptors, in some embodiments it is preferred that when a GPCR Fusion Protein is used and the assay is based upon detection of adenylyl cyclase activity, that the fusion construct be established with Gs (or an equivalent G protein that stimulates the formation of the enzyme adenylyl cyclase).

TABLE C

| G protein | Effect of cAMP Production upon Activation of GPCR (i.e., constitutive activation or agonist binding) | Effect of IP$_3$ Accumulation upon Activation of GPCR (i.e., constitutive activation or agonist binding) | Effect of cAMP Production upon contact with an Inverse Agonist | Effect on IP$_3$ Accumulation upon contact with an Inverse Agonist |
|---|---|---|---|---|
| Gs | Increase | N/A | Decrease | N/A |
| Gi | Decrease | N/A | Increase | N/A |
| Gz | Decrease | N/A | Increase | N/A |
| Go | Decrease | Increase | Increase | Decrease |
| Gq | N/A | Increase | N/A | Decrease |

Equally effective is a G Protein Fusion construct that utilizes a Gq Protein fused with a Gs, Gi, Gz or Go Protein. In some embodiments a preferred fusion construct can be accomplished with a Gq Protein wherein the first six (6) amino acids of the G-protein α-subunit ("Gαq") is deleted and the last five (5) amino acids at the C-terminal end of Gαq is replaced with the corresponding amino acids of the Gα of the G protein of interest. For example, a fusion construct can have a Gq (6 amino acid deletion) fused with a Gi Protein, resulting in a "Gq/Gi Fusion Construct". This fusion construct will force the endogenous Gi coupled receptor to couple to its non-endogenous G protein, Gq, such that the second messenger, for example, inositol triphosphate or diacylglycerol, can be measured in lieu of cAMP production.

4. Co-transfection of a Target Gi Coupled GPCR with a Signal-Enhancer Gs Coupled GPCR (cAMP Based Assays)

A Gi coupled receptor is known to inhibit adenylyl cyclase, and, therefore, decreases the level of cAMP production, which can make the assessment of cAMP levels challenging. In certain embodiments, an effective technique in measuring the decrease in production of cAMP as an indication of activation of a receptor that predominantly couples Gi upon activation can be accomplished by co-transfecting a signal enhancer, e.g., a non-endogenous, constitutively activated receptor that predominantly couples with Gs upon activation (e.g., TSHR-A623I; see infra), with the Gi linked GPCR. As is apparent, activation of a Gs coupled receptor can be determined based upon an increase in production of cAMP. Activation of a Gi coupled receptor leads to a decrease in production cAMP. Thus, the co-transfection approach is intended to advantageously exploit these "opposite" affects. For example, co-transfection of a non-endogenous, constitutively activated Gs coupled receptor (the "signal enhancer") with expression vector alone provides a baseline cAMP signal (i.e., although the Gi coupled receptor will decrease cAMP levels, this "decrease" will be relative to the substantial increase in cAMP levels established by constitutively activated Gs coupled signal enhancer). By then co-transfecting the signal enhancer with the "target receptor", an inverse agonist of the Gi coupled target receptor will increase the measured cAMP signal, while an agonist of the Gi coupled target receptor will decrease this signal.

Candidate compounds that are directly identified using this approach should be assessed independently to ensure that these do not target the signal enhancing receptor (this can be done prior to or after screening against the co-transfected receptors).

D. Medicinal Chemistry

Candidate Compounds

Any molecule known in the art can be tested for its ability to modulate (increase or decrease) the activity of a GPCR of the present invention. For identifying a compound that modulates activity, candidate compounds can be directly provided to a cell expressing the receptor.

This embodiment of the invention is well suited to screen chemical libraries for molecules which modulate, e.g., inhibit, antagonize, or agonize, the amount of, or activity of, a receptor. The chemical libraries can be peptide libraries, peptidomimetic libraries, chemically synthesized libraries, recombinant, e.g., phage display libraries, and in vitro translation based libraries, other non-peptide synthetic organic libraries, etc. This embodiment of the invention is also well suited to screen endogenous candidate compounds comprising biological materials, including but not limited to plasma and tissue extracts, and to screen libraries of endogenous compounds known to have biological activity.

In some embodiments, direct identification of candidate compounds is conducted in conjunction with compounds generated via combinatorial chemistry techniques, whereby thousands of compounds are randomly prepared for such analysis. The candidate compound may be a member of a chemical library. This may comprise any convenient number of subject members, for example tens to hundreds to thousand to millions of suitable compounds, for example peptides, peptoids and other oligomeric compounds (cyclic or linear), and template-based smaller molecules, for example benzodiazepines, hydantoins, biaryls, carbocyclic and polycyclic compounds (e.g., naphthalenes, phenothiazines, acridines, steroids etc.), carbohydrate and amino acid derivatives, dihydropyridines, benzhydryls and heterocycles (e.g., trizines, indoles, thiazolidines etc.). The numbers quoted and the types of compounds listed are illustrative, but not limiting. Preferred chemical libraries comprise chemical compounds of low molecular weight and potential therapeutic agents.

Exemplary chemical libraries are commercially available from several sources (ArQule, Tripos/PanLabs, ChemDesign, Pharmacopoeia). In some cases, these chemical libraries are generated using combinatorial strategies that encode the identity of each member of the library on a substrate to which the member compound is attached, thus allowing direct and immediate identification of a molecule that is an effective modulator. Thus, in many combinatorial approaches, the position on a plate of a compound specifies that compounds composition. Also, in one example, a single plate position may have from 1-20 chemicals that can be screened by administration to a well containing the interactions of interest. Thus, if modulation is detected, smaller and smaller pools of interacting pairs can be assayed for the modulation activity. By such methods, many candidate molecules can be screened.

Many diversity libraries suitable for use are known in the art and can be used to provide compounds to be tested according to the present invention. Alternatively, libraries can be constructed using standard methods. Further, more general, structurally constrained, organic diversity (e.g., nonpeptide) libraries, can also be used. By way of example, a benzodiazepine library (see e.g., Bunin et al., 1994, Proc. Natl. Acad. Sci. USA 91:4708-4712) may be used.

In another embodiment of the present invention, combinatorial chemistry can be used to identify modulators of the GPCRs of the present invention. Combinatorial chemistry is capable of creating libraries containing hundreds of thousands of compounds, many of which may be structurally similar. While high throughput screening programs are capable of screening these vast libraries for affinity for known targets, new approaches have been developed that achieve libraries of smaller dimension but which provide maximum chemical diversity. (See e.g., Matter, 1997, Journal of Medicinal Chemistry 40:1219-1229).

One method of combinatorial chemistry, affinity fingerprinting, has previously been used to test a discrete library of small molecules for binding affinities for a defined panel of proteins. The fingerprints obtained by the screen are used to predict the affinity of the subject library members for other proteins or receptors of interest (in the instant invention, the receptors of the present invention). The fingerprints are compared with fingerprints obtained from other compounds known to react with the protein of interest to predict whether the library compound might similarly react. For example, rather than testing every ligand in a large library for interaction with a complex or protein component, only those ligands having a fingerprint similar to other compounds known to have that activity could be tested. (See, e.g., Kauvar et al., 1995, Chemistry and Biology 2:107-118; Kauvar, 1995, Affinity fingerprinting, Pharmaceutical Manufacturing International. 8:25-28; and Kauvar, Toxic-Chemical Detection by Pattern Recognition in New Frontiers in Agrochemical Immunoassay, D. Kurtz. L. Stanker and J. H. Skerritt. Editors, 1995, AOAC: Washington, D.C., 305-312).

In some embodiments, the candidate compound is a polypeptide. In some preferred embodiments, the candidate compound is a small molecule. In some embodiments, the candidate compound is not an antibody or an antigen-binding fragment thereof.

Candidate Compounds Identified as Modulators

Generally, the results of such screening will be compounds having unique core structures; thereafter, these compounds may be subjected to additional chemical modification around a preferred core structure(s) to further enhance the medicinal properties thereof. Such techniques are known to those in the art and will not be addressed in detail in this patent document.

In certain embodiments, a modulator of the invention is orally active. A number of computational approaches available to those of ordinary skill in the art have been developed for prediction of oral bioavailability of a drug [Ooms et al., Biochim Biophys Acta (2002) 1587:118-25; Clark & Grootenhuis, Curr OpinDrug Discov Devel (2002) 5:382-90; Cheng et al., J Comput Chem (2002) 23:172-83; Norinder & Haeberlein, Adv Drug Deliv Rev (2002) 54:291-313; Matter et al., Comb Chem High Throughput Screen (2001) 4:453-75; Podlogar & Muegge, Curr Top Med Chem (2001) 1:257-75; the disclosure of each of which is herein incorporated by reference in its entirety). Furthermore, positron emission tomography (PET) has been successfully used by a number of groups to obtain direct measurements of drug distribution, including an assessment of oral bioavailability, in the mammalian body following oral administration of the drug, including non-human primate and human body [Noda et al., J Nucl Med (2003) 44:105-8; Gulyas et al., Eur J Nucl Med Mol Imaging (2002) 29:1031-8; Kanerva et al., Psychopharmacology (1999) 145:76-81; the disclosure of each of which is herein incorporated by reference in its entirety]. In some embodiments, a modulator of the invention is orally active.

In certain embodiments, a modulator of the invention which is orally active is able to cross the blood-brain barrier. A number of computational approaches available to those of ordinary skill in the art have been developed for prediction of the permeation of the blood-brain barrier [Ooms et al, Biochim Biophys Acta (2002) 1587:118-25; Clark & Grootenhuis, Curr OpinDrug Discov Devel (2002) 5:382-90; Cheng et al., J Comput Chem (2002) 23:172-83; Norinder & Haeberlein, Adv Drug Deliv Rev (2002) 54:291-313; Matter et al., Comb Chem High Throughput Screen (2001) 4:453-75; Podlogar & Muegge, Curr Top Med Chem (2001) 1:257-75; the disclosure of each of which is herein incorporated by reference in its entirety). A number of in vitro methods have been developed to predict blood-brain barrier permeability of drugs [Lohmann et al., J Drug Target (2002) 10:263-76; Hansen et al., J Pharm Biomed Anal (2002) 27:945-58; Otis et al., J Pharmacol Toxicol Methods (2001) 45:71-7; Dehouck et al, J Neurochem (1990) 54:1798-801; the disclosure of each of which is herein incorporated by reference in its entirety]. Furthermore, a number of strategies have been developed to enhance drug delivery across the blood-brain barrier [Scherrmann, Vascul Pharmacol (2002) 38:349-54; Pardridge, Arch Neurol (2002) 59:3540; Pardridge, Neuron (2002) 36:555-8; the disclosure of each of which is hereby incorporated by reference in its entirety]. Finally, positron emission tomography (PET) has been successfully used by a number of groups to obtain direct measurements of drug distribution, including that within brain, in the mammalian body, including non-human primate and human body [Noda et al., J Nucl Med (2003) 44:105-8; Gulyas et al., Eur J Nucl Med Mol Imaging (2002) 29:1031-8; Kanerva et al., Psychopharmacology (1999) 145:76-81; the disclosure of each of which is herein incorporated by reference in its entirety].

In some embodiments, said modulator is selective for GPR50, wherein a modulator selective for GPR50 is understood to refer to a modulator having selectivity for GPR50 over one or more closely related receptors, such as melatonin receptor 1A (MTNR1A; GenBank® Accession No. NP_005949) or melatonin receptor 1B (MTNR1B; GenBank® Accession No. NP_005950). In certain embodiments, a GPR50 selective modulator is a GPR50 selective inverse agonist or antagonist having a selectivity for GPR50 over MTNR1A or MTNR1B of at least about 10-fold or of at least about 100-fold. In certain embodiments, a GPR50 selective modulator is a GPR50 selective inverse agonist or antagonist having a selectivity for GPR50 over MTNR1A and MTNR1B of at least about 10-fold or of at least about 100-fold. In some preferred embodiments, GPR50 is human GPR50.

In some embodiments, the modulator is an inverse agonist or antagonist with an $IC_{50}$ of less than about 10 µM, of less than about 1 µM, of less than about 100 nM, or of less than about 10 nM at human, mouse or rat GPR50, preferably at human GPR50. In some embodiments, the modulator is an inverse agonist or antagonist with an $IC_{50}$ of less than a value selected from the interval of about 10 nM to 10 µM. In some embodiments, modulator is an inverse agonist or antagonist with an $IC_{50}$ of less than a value selected from the interval of about 10 nM to 1 µM. In some embodiments, the modulator is an inverse agonist or antagonist with an $IC_{50}$ of less than a value selected from the interval of about 10 nM to 100 nM. In some embodiments, the modulator is an inverse agonist or antagonist with an $IC_{50}$ of less than about 10 µM, of less than about 1 of less than about 100 nM, or of less than about 10 nM in GTPγS binding assay carried out with membrane from transfected CHO cells, or in pigment aggregation assay carried out in transfected melanophores, or in cAMP assay carried out in transfected 293 cells optionally co-transfected with TSHR, wherein the transfected CHO cells or the transfected melanophore cells or the transfected 293 cells express a recombinant GPR50 having an amino acid sequence selected from SEQ ID NO: 2, SEQ ID NO: 4, SEQ ID NO: 6 and SEQ ID NO: 8. In some embodiments, the recombinant GPR50 has the amino acid sequence of SEQ ID NO: 2. In some embodiments, the recombinant GPR50 has the amino acid sequence of SEQ ID NO: 4. In some embodiments, the modulator is an inverse agonist or antagonist with an $IC_{50}$ of less than about 10 μM, of less than about 1 μM, of less than about 100 nM, or of less than about 10 nM in said assay. In some embodiments, said modulator is an inverse agonist or antagonist with an $IC_{50}$ of less than 10 μM in said assay, of less than 9 μM in said assay, of less than 8 μM in said assay, of less than 7 μM in said assay, of less than 6 μM in said assay, of less than 5 μM in said assay, of less than 4 μM in said assay, of less than 3 μM in said assay, of less than 2 μM in said assay, of less than 1 μM in said assay, of less than 900 nM in said assay, of less than 800 nM in said assay, of less than 700 nM in said assay, of less than 600 nM in said assay, of less than 500 nM in said assay, of less than 400 nM in said assay, of less than 300 nM in said assay, of less than 200 nM in said assay, of less than 100 nM in said assay, of less than 90 nM in said assay, of less than 80 nM in said assay, of less than 70 nM in said assay, of less than 60 nM in said assay, of less than 50 nM in said assay, of less than 40 nM n said assay, of less than 30 nM in said assay, of less than 20 nM in said assay, or of less than 10 nM in said assay. In some embodiments, the modulator is an inverse agonist or antagonist with an $IC_{50}$ in said assay of less than a value selected from the interval of about 10 nM to 10 μM. In some embodiments, the modulator is an inverse agonist or antagonist with an $IC_{50}$ in said assay of less than a value selected from the interval of about 10 nM to 1 μM. In some embodiments, the modulator is an inverse agonist or antagonist with an $IC_{50}$ in said assay of less than a value selected from the interval of about 10 nM to 100 nM.

In some embodiments, the modulator is an agonist or partial agonist with an $EC_{50}$ of less than about 10 μM, of less than about 1 μM, of less than about 100 nM, or of less than about 10 nM at human, mouse or rat GPR50, preferably at human GPR50. In some embodiments, the modulator is an agonist or partial agonist with an $EC_{50}$ of less than a value selected from the interval of about 10 nM to 10 μM. In some embodiments, modulator is an agonist or partial agonist with an $EC_{50}$ of less than a value selected from the interval of about 10 nM to 1 μM. In some embodiments, the modulator is an agonist or partial agonist with an $EC_{50}$ of less than a value selected from the interval of about 10 nM to 100 nM. In some embodiments, the modulator is an agonist or partial agonist with an $EC_{50}$ of less than about 10 μM, of less than about 1 μM, of less than about 100 nM, or of less than about 10 nM in GTPγS binding assay carried out with membrane from transfected CHO cells, or in pigment aggregation assay carried out in transfected melanophores, or in cAMP assay carried out in transfected 293 cells optionally co-transfected with TSHR, wherein the transfected CHO cells or the transfected melanophore cells or the transfected 293 cells express a recombinant GPR50 having an amino acid sequence selected from SEQ ID NO: 2, SEQ ID NO: 4, SEQ ID NO: 6 and SEQ ID NO: 8. In some embodiments, the recombinant GPR50 has the amino acid sequence of SEQ ID NO: 2. In some embodiments, the recombinant GPR50 has the amino acid sequence of SEQ ID NO: 4. In some embodiments, the modulator is an agonist or partial agonist with an $EC_{50}$ of less than about 10 μM, of less than about 1 μM, of less than about 100 nM, or of less than about 10 nM in said assay. In some embodiments, said modulator is an agonist or partial agonist with an $EC_{50}$ of less than 10 μM in said assay, of less than 9 μM in said assay, of less than 8 μM in said assay, of less than 7 μM in said assay, of less than 6 μM in said assay, of less than 5 μM in said assay, of less than 4 μM in said assay, of less than 3 μM in said assay, of less than 2 μM in said assay, of less than 1 μM in said assay, of less than 900 nM in said assay, of less than 800 nM in said assay, of less than 700 nM in said assay, of less than 600 nM in said assay, of less than 500 nM in said assay, of less than 400 nM in said assay, of less than 300 nM in said assay, of less than 200 nM in said assay, of less than 100 nM in said assay, of less than 90 nM in said assay, of less than 80 nM in said assay, of less than 70 nM in said assay, of less than 60 nM in said assay, of less than 50 nM in said assay, of less than 40 nM n said assay, of less than 30 nM in said assay, of less than 20 nM in said assay, or of less than 10 nM in said assay. In some embodiments, the modulator is an agonist or partial agonist with an $EC_{50}$ in said assay of less than a value selected from the interval of about 10 nM to 10 μM. In some embodiments, the modulator is an agonist or partial agonist with an $EC_{50}$ in said assay of less than a value selected from the interval of about 10 nM to 1 μM. In some embodiments, the modulator is an agonist or partial agonist with an $EC_{50}$ in said assay of less than a value selected from the interval of about 10 nM to 100 nM.

E. Pharmaceutical Compositions

Compounds of the invention can be formulated into pharmaceutical compositions using techniques well known in the art.

The invention provides methods of treatment (and prevention) by administration to a subject in need of said treatment (or prevention) a therapeutically effect amount of a modulator or a ligand of the invention [also see, e.g., PCT Application Number PCT/IB02/01461 published as WO 02/066505 on 29 Aug. 2002; the disclosure of each of which is herein incorporated by reference in its entirety]. In one aspect, the modulator or the ligand is a small molecule. In one aspect, the modulator is an inverse agonist or an antagonist. In one aspect, the modulator is an inverse agonist. In one aspect, the modulator is an antagonist. In one aspect, the modulator is substantially purified. In one aspect, the subject is a mammal including, but not limited to cows, pigs, horses, non-human primates, cats, dogs, rabbits, rats, mice, etc., and is preferably a human.

Modulators of the invention can be administered to non-human mammals [see Examples, infra] and/or humans, alone or in pharmaceutical compositions where they are mixed with suitable carriers or excipient(s) using techniques well known to those in the art. Suitable pharmaceutically-acceptable carriers are available to those in the art; for example, see Remington's Pharmaceutical Sciences, 16$^{th}$ Edition, 1980, Mack Publishing Co., (Oslo et al., eds.).

The pharmaceutical composition is then provided at a therapeutically effective dose. A therapeutically effective dose refers to that amount of a modulator sufficient to result in prevention or amelioration of symptoms or physiological status of a disorder as determined illustratively and not by limitation by the methods described herein, wherein the prevention or amelioration of symptoms or physiological status of a disorder includes but is not limited to decreasing body mass in a subject, decreasing adiposity in a subject, decreasing percentage body fat in a subject, and preventing or treating obesity or a condition related thereto.

It is expressly considered that the modulators of the invention may be provided alone or in combination with other pharmaceutically or physiologically acceptable compounds. Other compounds for the treatment of disorders of the invention, wherein the treatment of disorders of the invention includes but is not limited to decreasing body mass in a subject, decreasing percentage body fat in a subject, and preventing or treating obesity or a condition related thereto.

While the compounds of the invention can be administered as the sole active pharmaceutical agent (i.e., mono-therapy), compounds of the invention can also be used in combination with other pharmaceutical agents (i.e., combination-therapy) for the treatment of the diseases/conditions/disorders described herein. Therefore, another aspect of the present invention includes methods of treatment comprising administering to a subject in need of treatment a therapeutically effective amount of an antagonist or an inverse agonist of the present invention in combination with one or more additional pharmaceutical agent as described herein.

It will be understood that the scope of combination-therapy of the compounds of the present invention with other pharmaceutical agents is not limited to those listed herein, supra or infra, but includes in principle any combination with any pharmaceutical agent or pharmaceutical composition useful for the treatment diseases, conditions or disorders of the present invention in a subject.

In one aspect of the present invention, the other pharmaceutically or physiologically acceptable compound is an anti-obesity agent such as apolipoprotein-B secretion/microsomal triglyceride transfer protein (apo-B/MTP) inhibitors, MCR-4 agonists, cholescystokinin-A (CCK-A) agonists, serotonin and norepinephrine reuptake inhibitors (for example, sibutramine), sympathomimetic agents, β3 adrenergic receptor agonists, dopamine agonists (for example, bromocriptine), melanocyte-stimulating hormone receptor analogs, $5\text{-HT}_{2C}$ serotonin receptor agonists (for example, lorcaserin hydrochloride), cannabinoid 1 receptor antagonists [for example, SR141716: N-(piperidin-1-yl)-5-(4-chlorophenyl)-1-(2,4-dichlorophenyl)-4-methyl-1H-pyrazole-3-carboxamide], melanin concentrating hormone antagonists, leptons (the OB protein), leptin analogues, leptin receptor agonists, galanin antagonists, lipase inhibitors (such as tetrahydrolipstatin, i.e., Orlistat), anorectic agents (such as a bombesin agonist), Neuropeptide-Y antagonists, thyromimetic agents, dehydroepiandrosterone or an analogue thereof, glucocorticoid receptor agonists or antagonists, orexin receptor antagonists, urocortin binding protein antagonists, glucagon-like peptide-1 receptor agonists, ciliary neutrotrophic factors (such as Axokine™ available from Regeneron Pharmaceuticals, Inc., Tarrytown, N.Y. and Procter & Gamble Company, Cincinnati, Ohio), human agouti-related protein (AGRP) antagonists, ghrelin receptor antagonists, histamine 3 receptor antagonists or reverse agonists, neuromedin U receptor agonists, noradrenergic anorectic agents (for example, phentermine, mazindol and the like) and appetite suppressants (for example, bupropion). In some embodiments, the anti-obesity agent is selected from the group consisting of orlistat, sibutramine, bromocriptine, ephedrine, leptin, and pseudoephedrine.

In accordance to an aspect of the present invention, a compound of the present invention can be used in combination with a pharmaceutical agent or agents belonging to one or more of the classes of drugs cited herein.

Routes of Administration

Suitable routes of administration include oral, nasal, rectal, transmucosal, transdermal, or intestinal administration, parenteral delivery, including intramuscular, subcutaneous, intramedullary injections, as well as intrathecal, direct intraventricular, intravenous, intraperitoneal, intranasal, intrapulmonary (inhaled) or intraocular injections using methods known in the art. Other particularly preferred routes of administration are aerosol and depot formulation. Sustained release formulations, particularly depot, of the invented medicaments are expressly contemplated. In certain embodiments, route of administration is oral.

Composition/Formulation

Pharmaceutical or physiologically acceptable compositions and medicaments for use in accordance with the present invention may be formulated in a conventional manner using one or more physiologically acceptable carriers comprising excipients and auxiliaries. Proper formulation is dependent upon the route of administration chosen.

Certain of the medicaments described herein will include a pharmaceutically or physiologically acceptable carrier and at least one modulator of the invention. For injection, the agents of the invention may be formulated in aqueous solutions, preferably in physiologically compatible buffers such as Hanks's solution, Ringer's solution, or physiological saline buffer such as a phosphate or bicarbonate buffer. For transmucosal administration, penetrants appropriate to the barrier to be permeated are used in the formulation. Such penetrants are generally known in the art.

Pharmaceutical or physiologically acceptable preparations that can be taken orally include push-fit capsules made of gelatin, as well as soft, sealed capsules made of gelatin and a plasticizer, such as glycerol or sorbitol. The push-fit capsules can contain the active ingredients in admixture with fillers such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration. For buccal administration, the compositions may take the form of tablets or lozenges formulated in conventional manner.

For administration by inhalation, the compounds for use according to the present invention are conveniently delivered in the form of an aerosol spray presentation from pressurized packs for a nebulizer, with the use of a suitable gaseous propellant, e.g., carbon dioxide. In the case of a pressurized aerosol the dosage unit may be determined by providing a valve to deliver a metered amount. Capsules and cartridges of, e.g., gelatin, for use in an inhaler or insufflator, may be formulated containing a powder mix of the compound and a suitable powder base such as lactose or starch.

The compounds may be formulated for parenteral administration by injection, e.g., by bolus injection or continuous infusion. Formulations for injection may be presented in unit dosage for, e.g., in ampoules or in multi-dose containers, with an added preservative. The compositions may take such forms as suspension, solutions or emulsions in aqueous vehicles, and may contain formulatory agents such as suspending, stabilizing and/or dispersing agents.

Pharmaceutical or physiologically acceptable formulations for parenteral administration include aqueous solutions of the active compounds in water-soluble form. Aqueous suspension may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

Alternatively, the active ingredient may be in powder or lyophilized form for constitution with a suitable vehicle, such as sterile pyrogen-free water, before use.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

In a particular embodiment, the compounds can be delivered via a controlled release system. In one embodiment, a pump may be used (Langer, supra; Sefton, 1987, CRC Crit. Ref. Biomed. Eng. 14:201-240; Buchwald et al., 1980, Surgery 88:507-516; Saudek et al., 1989, N. Engl. J. Med. 321: 574-579). In another embodiment, polymeric materials can be used (Medical Applications of Controlled Release, Langer and Wise, eds., CRC Press, Boca Raton, Fla., 1974; Controlled Drug Bioavailability, Drug Product Design and Performance, Smolen and Ball, eds., Wiley, New York, 1984; Ranger and Peppas, 1983, Macromol. Sci. Rev. Macromol. Chem. 23:61; Levy et al., 1985, Science 228:190-192; During et al., 1989, Ann. Neurol. 25:351-356; Howard et al., 1989, J. Neurosurg. 71:858-863). Other controlled release systems are discussed in the review by Langer (1990, Science 249: 1527-1533).

Additionally, the compounds may be delivered using a sustained-release system, such as semipermeable matrices of solid hydrophobic polymers containing the therapeutic agent. Various sustained release materials have been established and are well known by those skilled in the art. Sustained-release capsules may, depending on their chemical nature, release the compounds for a few weeks up to over 100 days.

Depending on the chemical nature and the biological stability of the therapeutic reagent, additional strategies for modulator stabilization may be employed.

The pharmaceutical or physiologically acceptable compositions also may comprise suitable solid or gel phase carriers or excipients. Examples of such carriers or escipients include but are not limited to calcium carbonate, calcium phosphate, various sugars, starches, cellulos derivatives, gelatin, and polymers such as polyethylene glycols.

Effective Dosage

Pharmaceutical or physiologically acceptable compositions suitable for use in the present invention include compositions wherein the active ingredients are contained in an effective amount to achieve their intended purpose. More specifically, a therapeutically effective amount means an amount effective to prevent development of or to alleviate the existing symptoms of the subject being treated. Determination of the effective amounts is wll within the capability of those skilled in the art, especially in light of the detailed disclosure provided herein.

For any compound used in the method of the invention, the therapeutically effective dose can be estimated initially from cell culture assays. For example, a dose can be formulated in animal models to achieve a circulating concentration range that includes or encompasses a concentration point or range shown to increase an intracellular level of cAMP in a cell comprising GPR50 in an in vitro assay. Such information can be used to more accurately determine useful doses in humans.

A therapeutically effective dose refers to that amount of the compound that results in amelioration of symptoms in a patient. Toxicity and therapeutic efficacy of such compounds can be determined by standard pharmaceutical procedures in cell cultures or experimental animals, e.g., for determining the $LD_{50}$ (the dose lethal to 50% of the test population) and the $ED_{50}$ (the dose therapeutically effective in 50% of the test population). The dose ratio between toxic and therapeutic effects is the therapeutic index and it can be expressed as the ratio between $LD_{50}$ and $ED_{50}$. Compounds that exhibit high therapeutic indices are preferred.

The data obtained from these cell culture assays and animal studies can be used in formulating a range of dosage for use in humans. The dosage of such compounds lies preferably within a range of circulating concentrations that include the $ED_{50}$, with little or no toxicity. The dosage may vary within this range depending upon the dosage form employed and the route of administration utilized. The exact formulation, route of administration and dosage can be chosen by the subject physician in view of the patient's condition. (See, e.g., Fingl et al., 1975, in "The Pharmacological Basis of Therapeutics", Ch. 1).

Dosage amount and interval may be adjusted subjectly to provide plasma levels of the active compound which are sufficient to prevent or treat a disorder of the invention, depending on the particular situation. Dosages necessary to achieve these effects will depend on subject characteristics and route of administration.

Dosage intervals can also be determined using the value for the minimum effective concentration. Compounds should be administered using a regimen that maintains plasma levels above the minimum effective concentration for 10-90% of the time, preferably between 30-99%, and most preferably between 50-90%. In cases of local administration or selective uptake, the effective local concentration of the drug may not be related to plasma concentration.

The amount of composition administered will, of course, be dependent on the subject being treated, on the subject's weight, the severity of the affliction, the manner of administration, and the judgement of the prescribing physician.

A preferred dosage range for the amount of a modulator of the invention, which can be administered on a daily or regular basis to achieve desired results is 0.1-100 mg/kg body mass. Other preferred dosage range is 0.1-30 mg/kg body mass. Other preferred dosage range is 0.1-10 mg/kg body mass. Other preferred dosage range is 0.1-3.0 mg/kg body mass. Of course, these daily dosages can be delivered or administered in small amounts periodically during the course of a day. It is noted that these dosage ranges are only preferred ranges and are not meant to be limiting to the invention. Said desired results include, but are not limited to, decreasing body mass in a subject, decreasing adiposity in a subject, decreasing percentage body fat in a subject, and preventing or treating obesity or a condition related thereto.

F. Methods of Treatment

The invention is drawn inter alia to methods including, but not limited to, methods of decreasing body mass in a subject, of decreasing adiposity in a subject, of decreasing percentage body fat in a subject, and of preventing or treating obesity or a condition related thereto, comprising administering to a subject in need of said decreasing, preventing or treating with a modulator of the invention. In some embodiments, the modulator is an inverse agonist or antagonist. In some embodiments, the modulator is an inverse agonist. In some embodiments, the modulator is an antagonist. In some embodiments, said modulator is orally active. In some embodiments, said orally active modulator is further able to cross the blood-brain barrier. In some embodiments, the modulator is administered to the subject in a pharmaceutical composition. In some embodiments, the modulator is provided to the subject in a pharmaceutical composition. In some embodiments, the modulator is provided to the subject in a pharmaceutical composition that is taken orally. In some embodiments, the subject is a non-human mammal. In some embodiments, the subject is a mammal. In certain embodiments, the mammal is a mouse, a rat, a non-human primate, or a human. In certain preferred embodiments, the subject or mammal is a human.

In some embodiments, the subject is in need of having body mass decreased. In some embodiments, the subject is in need of having percentage body fat decreased. In some embodiments, the subject is in need of preventing or treating obesity or a condition related thereto.

In some embodiments, the subject is overweight or obese. In some embodiments, the subject is overweight. In some embodiments, the subject is obese.

In some embodiments, the obesity comprises weight gain induced by a high fat diet.

In some embodiments, the condition related to obesity is selected from the group consisting of hypertension, congestive cardiomyopathy, varicosities, pulmonary embolism, coronary heart disease, stroke, idiopathic intracranial hypertension, meralgia parethetica, dyspnea, obstructive sleep apnea, hypoventilation syndrome, Pickwickian syndrome, asthma, immobility, degenerative osteoarthritis, low back pain, striae distensae or "stretch marks," venous stasis of the lower extremities, lymphedema, cellulitis, intertrigo, carbuncles, acanthosis nigricans, skin tags, gastro-esophageal reflux disorder, nonalcoholic fatty liver/steatohepatitis, cholelithiasis, hernias, colon cancer, stress incontinence, obesity-related glomerulopathy, breast and uterine cancer, depression and low self-esteem, impaired quality of life, metabolic syndrome, insulin resistance, Type 2 diabetes, dyslipidemia, atherosclerosis, hyperandrogenemia in women, polycystic ovarian syndrome, dysmenorrhea, infertility, pregnancy complications, and male hypogonadism. In some embodiments, the condition related to obesity is selected from the group consisting of hypertension, insulin resistance, metabolic syndrome, Type 2 diabetes, dyslipidemia, atherosclerosis, coronary heart disease, and stroke.

The invention also contemplates methods of preventing or treating a disorder ameliorated by increasing body mass including, but not limited to; cachexia, wasting, AIDS-related weight loss, cancer-related weight loss, anorexia, and bulimia, comprising administering to a subject in need of said preventing or treating with a modulator of the invention. In some embodiments, the modulator is an agonist or partial agonist. In some embodiments, the modulator is an agonist. In some embodiments, the modulator is a partial agonist. In some embodiments, said modulator is orally active. In some embodiments, said orally active modulator is further able to cross the blood-brain barrier. In some embodiments, the modulator is administered to the subject in a pharmaceutical composition. In some embodiments, the modulator is provided to the subject in a pharmaceutical composition. In some embodiments, the modulator is provided to the subject in a pharmaceutical composition that is taken orally. In some embodiments, the subject is a non-human mammal. In some embodiments, the subject is a mammal. In certain embodiments, the mammal is a mouse, a rat, a non-human primate, or a human. In certain preferred embodiments, the subject or mammal is a human.

G. Other Utility

Agents that modulate (i.e., increase, decrease, or block) receptor functionality of a GPCR of the invention such as a mammalian GPR50 may be identified by contacting a candidate compound with the GPCR and determining the effect of the candidate compound on receptor functionality. The selectivity of a compound that modulates the functionality of a mammalian GPR50 such as human GPR50 can be evaluated by comparing its effects on GPR50 to its effects on one or more other G protein-coupled receptors. In certain embodiments, a GPR50 selective modulator is a GPR50 selective inverse agonist or antagonist having a selectivity for GPR50 over MTNR1A or MTNR1B of at least about 10-fold or of at least about 100-fold. In certain embodiments, a GPR50 selective modulator is a GPR50 selective inverse agonist or antagonist having a selectivity for GPR50 over MTNR1A and MTNR1B of at least about 10-fold or of at least about 100-fold. Following identification of compounds that modulate GPR50 functionality, such candidate compounds may be further tested in other assays including, but not limited to, in vivo models, in order to confirm or quantitate their activity. By way of illustration and not limitation, the subject invention expressly contemplates the identification of compounds as modulators of a mammalian GPR50 GPCR for use as pharmaceutical agents. Modulators of GPR50 functionality are therapeutically useful, e.g., in treatment of diseases and physiological conditions in which normal or aberrant GPR50 functionality is involved.

Agents that are ligands of a GPCR of the invention such as a mammalian GPR50 may be identified by contacting a candidate compound with the GPCR and determining whether the candidate compound binds to the receptor. The selectivity of a compound that binds to a mammalian GPR50 such as human GPR50 can be evaluated by comparing its binding to GPR50 to its binding to one or more other G protein-coupled receptors. Ligands that are modulators of GPR50 receptor functionality are therapeutically useful in treatment of diseases and physiological conditions in which normal or aberrant GPR50 functionality is involved.

In other embodiments, agents that are modulators (e.g., increase or decrease) of body mass, adiposity or percentage of body weight in a subject or that are useful as pharmaceutical agents for obesity and conditions related thereto are identified by contacting a candidate compound with a GPR50 receptor and determining the effect of the candidate compound on GPR50 receptor expression. In some embodiments, the agent reduces expression of GPR50 receptor in a cell. In some embodiments, the agent reduces expression of GPR50 receptor in a neuronal cell. In some embodiments, the agent reduces expression of GPR40 receptor in a human neuronal cell. In some embodiments, the GPR50 receptor is endogenously expressed by the cell or neuronal cell. In some embodiments, a level of GPR50 receptor expression is measured using anti-GPR50 receptor antibody. Those of skill in the art are credited with the ability to produce antibody to human, rat or mouse GPR50 receptor that may be used to measure a level of GPR50 expression in a cell. In some embodiments, a level of GPR50 receptor expression is measured using radiolableled ligand specific for GPR50 receptor (see infra). In some embodiments, a level of GPR50 receptor expression is measured by Northern blot or RT-PCR.

The present invention also relates to a method of identifying whether a candidate compound is an agent that reduces expression of GPR50 receptor in a cell, said method comprising the steps of:

(a) contacting or not contacting a plurality of cells comprising GPR50 receptor with a candidate compound;

(b) measuring the level of GPR50 receptor expression in the cells contacted with the candidate compound and the level of GPR50 receptor expression in the cells not contacted with the candidate compound; and (c) comparing the level of GPR50 receptor expression in the cells contacted with the candidate compound with the level of GPR50 receptor expression in the cells not contacted with the candidate compound; wherein a reduction in the level of GPR50 receptor expression in the cells contacted with the candidate compound compared with the level of GPR50 receptor expression in the cells not contacted with the candidate compound is indicative of the candidate compound being an agent that reduces expression of GPR50 receptor in a cell.

The present invention also relates to a method of identifying a candidate compound as a pharmaceutical agent for obesity or a condition related thereto, said method comprising the steps of:
(a) contacting or not contacting a plurality of cells comprising GPR50 receptor with a candidate compound;
(b) measuring the level of GPR50 receptor expression in the cells contacted with the candidate compound and the level of GPR50 receptor expression in the cells not contacted with the candidate compound; and
(c) comparing the level of GPR50 receptor expression in the cells contacted with the candidate compound with the level of GPR50 receptor expression in the cells not contacted with the candidate compound; wherein a reduction in the level of GPR50 receptor expression in the cells contacted with the candidate compound compared with the level of GPR50 receptor expression in the cells not contacted with the candidate compound is indicative of the candidate compound being a pharmaceutical agent for obesity or a condition related thereto.

In certain embodiments, the pharmaceutical agent for obesity or a condition related thereto is a compound for preventing or treating obesity or a condition related thereto.

In some embodiments, said method of identifying whether a candidate compound is an agent that reduces expression of GPR50 receptor in a cell is an in vitro method.

In some embodiments, said plurality of cells contacted or not contacted with the candidate compound in step (a) are cultured for at least about 1 hour, at least about 2 hours, at least about 4 hours, at least about 8 hours, at least about 16 hours, at least about 24 hours, at least about 36 hours or at least about 48 hours before the level of GPR50 receptor expression in said cells is measured in step (b).

The present invention relates to said agent that reduces GPR50 expression in a cell (e.g., a neuronal cell), to a composition comprising said agent (e.g., a pharmaceutical composition), and to methods of using said composition (e.g., for the prevention of or treatment of obesity or a condition related thereto), wherein the compound is a small molecule. The present invention relates to said agent that reduces GPR50 expression in a cell (e.g., a neuronal cell), to a composition comprising said agent (e.g., a pharmaceutical composition), and to methods of using said composition (e.g., for the prevention of or treatment of obesity or a condition related thereto), wherein the compound is antisense nucleic acid (e.g., antisense RNA). The present invention relates to said agent that reduces GPR50 expression in a cell (e.g., a neuronal cell), to a composition comprising said agent (e.g., a pharmaceutical composition), and to methods of using said composition (e.g., for the prevention of or treatment of obesity or a condition related thereto), wherein the compound is a small interfering RNA (siRNA) or short hairpin RNA (shRNA) molecule comprising a nucleotide sequence derived from the nucleotide sequence of a GPR50 receptor-encoding gene according to standard procedures. As will be known to the skilled artisan, siRNA, shRNA and antisense RNA are generally capable of modulating expression of a target gene [see, e.g., Holmlund J T, Ann NY Acad Sci (2003) 1002:244-251; and Devroe et al, Expert Opin Biol Ther (2004) 4:319-327; the disclosure of each of which is hereby incorporated by reference in its entirety].

The present invention also relates to radioisotope-labeled versions of compounds of the invention identified as modulators or ligands of a GPCR of the invention such as a mammalian GPR50 that would be useful not only in radio-imaging but also in assays, both in vitro and in vivo, for localizing and quantitating GPR50 in tissue samples, including human, and for identifying GPR50 ligands in methods relating to inhibition of binding of a radioisotope-labeled compound such as a known ligand of GPR50. It is a further object of this invention to develop novel assays relating to a GPCR of the invention such as a mammalian GPR50, such as human GPR50, which comprise such radioisotope-labeled compounds. By way of illustration and not limitation, it is envisioned that elevated brain GPR50 above a normal range visualized by radio-imaging identifies a subject at risk for obesity or a condition related thereto. In some embodiments, the brain GPR50 is hypothalamic GPR50. In some embodiments, the brain GPR50 is pituitary GPR50. In some embodiments, the subject is a human.

The present invention also relates a method of radio-imaging comprising administering to a mammal in need of said radio-imaging a radiolabeled compound that is a modulator or a ligand of the mammalian GPR50 receptor. In one aspect, the ligand of the mammalian GPR50 receptor is not a modulator of the mammalian GPR50 receptor. In some embodiments, the mammal is a human. In some embodiments, the method of radio-imaging is for identifying whether the mammal is at risk for or progressing toward obesity or a condition related thereto, wherein a level of brain GPR50 in the mammal above the normal range is indicative of the mammal being at risk for or progressing toward obesity or a condition related thereto. In some embodiments, the method of radio-imaging is for identifying the mammal for prevention or treatment of obesity or a condition related thereto with an inverse agonist or an antagonist of the mammalian GPR50 or with an agent that decreases GPR50 expression in a cell or with a pharmaceutical composition comprising the inverse agonist or the antagonist or the agent and a pharmaceutically acceptable carrier, wherein a level of brain GPR50 in the mammal above a normal range identifying the mammal for prevention or treatment of obesity or a condition related thereto with the inverse agonist or the antagonist of the mammalian GPR50 or with the agent that decreases GPR50 expression in a cell or with the pharmaceutical composition comprising the inverse agonist or the antagonist or the agent and a pharmaceutically acceptable carrier. In some embodiments, the brain GPR50 is hypothalamic GPR50. In some embodiments, the brain GPR50 is pituitary GPR50.

The present invention embraces radioisotope-labeled versions of compounds of the invention identified as modulators or ligands of a GPCR of the invention such as a mammalian GPR50, such as human GPR50.

The present invention also relates to radioisotope-labeled versions of test ligands that are useful for detecting a ligand bound to a GPCR of the invention such as a mammalian GPR50, such as human GPR50. In some embodiments, the present invention expressly contemplates a library of said radiolabeled test ligands useful for detecting a ligand bound to a GPCR of the invention such as a mammalian GPR50, such as human GPR50. In certain embodiments, said library comprises at least about 10, at least about $10^2$, at least about $10^3$, at least about $10^5$, or at least about $10^6$ said radiolabeled test compounds. It is a further object of this invention to develop novel assays relating to a GPCR of the invention such as a mammalian GPR50, such as human GPR50, which comprise such radioisotope-labeled test ligands.

In some embodiments, a radioisotope-labeled version of a compound is identical to the compound, but for the fact that one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^2$H (deuterium), $^3$H (tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I, and $^{131}$I. The radionuclide that is incorporated in the instant radio-labeled compound will depend on the specific application of that radio-labeled compound. For example, for in vitro GPR50 receptor labeling and competition assays, compounds that incorporate $^3$H, $^{14}$C, $^{82}$Br, $^{125}$I, $^{131}$I, $^{35}$S or will generally be most useful. For radio-imaging applications $^{11}$C, $^{18}$F, $^{125}$I, $^{123}$I, $^{124}$I, $^{131}$I, $^{75}$Br, $^{76}$Br or $^{77}$Br will generally be most useful. In some embodiments, the radionuclide is selected from the group consisting of $^3$H, $^{11}$C, $^{18}$F, $^{14}$C, $^{125}$I, $^{124}$I, $^{131}$I, $^{35}$S and $^{82}$Br.

Synthetic methods for incorporating radio-isotopes into organic compounds are applicable to compounds of the invention and are well known in the art. These synthetic methods, for example, incorporating activity levels of tritium into target molecules, are as follows:

A. Catalytic Reduction with Tritium Gas—This procedure normally yields high specific activity products and requires halogenated or unsaturated precursors.

B. Reduction with Sodium Borohydride [$^3$H]—This procedure is rather inexpensive and requires precursors containing reducible functional groups such as aldehydes, ketones, lactones, esters, and the like.

C. Reduction with Lithium Aluminum Hydride [$^3$H]—This procedure offers products at almost theoretical specific activities. It also requires precursors containing reducible functional groups such as aldehydes, ketones, lactones, esters, and the like.

D. Tritium Gas Exposure Labeling—This procedure involves exposing precursors containing exchangeable protons to tritium gas in the presence of a suitable catalyst.

E. N-Methylation using Methyl Iodide [$^3$H]—This procedure is usually employed to prepare O-methyl or N-methyl ($^3$H) products by treating appropriate precursors with high specific activity methyl iodide ($^3$H). This method in general allows for higher specific activity, such as for example, about 70-90 Ci/mmol.

Synthetic methods for incorporating activity levels of $^{125}$I into target molecules include:

A. Sandmeyer and like reactions—This procedure transforms an aryl or heteroaryl amine into a diazonium salt, such as a tetrafluoroborate salt, and subsequently to $^{125}$I labeled compound using Na$^{125}$I. A represented procedure was reported by Zhu, D.-G. and co-workers in *J. Org. Chem.* 2002, 67, 943-948.

B. Ortho $^{125}$Iodination of phenols—This procedure allows for the incorporation of $^{125}$I at the ortho position of a phenol as reported by Collier, T. L. and co-workers in *J. Labeled Compd Radiopharm.* 1999, 42, S264-S266.

C. Aryl and heteroaryl bromide exchange with $^{125}$I—This method is generally a two step process. The first step is the conversion of the aryl or heteroaryl bromide to the corresponding tri-alkyltin intermediate using for example, a Pd catalyzed reaction [i.e. Pd(Ph$_3$P)$_4$] or through an aryl or heteroaryl lithium, in the presence of a tri-alkyltinhalide or hexaalkylditin [e.g., (CH$_3$)$_3$SnSn(CH$_3$)$_3$]. A represented procedure was reported by Bas, M.-D. and co-workers in *J. Labeled Compd Radiopharm.* 2001, 44, S280-S282.

In some embodiments, a radioisotope-labeled version of a compound is identical to the compound, but for the addition of one or more substituents comprising a radionuclide. In some further embodiments, the compound is a polypeptide. In some further embodiments, the compound is an antibody or an antigen-binding fragment thereof. In some further embodiments, said antibody is monoclonal. Suitable said radionuclide includes but is not limited to $^2$H (deuterium), $^3$H (tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I, $^{125}$I and $^{131}$I. The radionuclide that is incorporated in the instant radio-labeled compound will depend on the specific application of that radio-labeled compound. For example, for in vitro GPR50 receptor labeling and competition assays, compounds that incorporate $^3$H, $^{14}$C, $^{82}$Br, $^{125}$I, $^{131}$I, $^{35}$S or will generally be most useful. For radio-imaging applications $^{11}$C, $^{18}$F, $^{125}$I, $^{123}$I, $^{124}$I, $^{131}$I, $^{75}$Br, $^{76}$Br or $^{77}$Br will generally be most useful. In some embodiments, the radionuclide is selected from the group consisting of $^3$H, $^{11}$C, $^{18}$F, $^{14}$C, $^{125}$I, $^{124}$I, $^{131}$I, $^{35}$S, $^{35}$S and $^{82}$Br.

Methods for adding one or more substituents comprising a radionuclide are within the purview of the skilled artisan and include, but are not limited to, addition of radioisotopic iodine by enzymatic method [Marchalonic J J, Biochemical Journal (1969) 113:299-305; Thorell J I and Johansson B G, Biochimica et Biophysica Acta (1969) 251:363-9; the disclosure of each of which is herein incorporated by reference in its entirety] and or by Chloramine-T/Iodogen/Iodobead methods [Hunter W M and Greenwood F C, Nature (1962) 194: 495-6; Greenwood F C et al., Biochemical Journal (1963) 89:114-23; the disclosure of each of which is herein incorporated by reference in its entirety].

Other uses of the disclosed receptors and methods will become apparent to those in the art based upon, inter alia, a review of this patent document.

EXAMPLES

The following examples are presented for purposes of elucidation, and not limitation, of the present invention. While specific nucleic acid and amino acid sequences are disclosed herein, those of ordinary skill in the art are credited with the ability to make minor modifications to these sequences while achieving the same or substantially similar results reported below. Such modified approaches are considered within the purview of this disclosure. Without further elaboration, it is believed that one skilled in the art can, using the preceding description, practice the present invention to its fullest extent. The following detailed examples are to be construed as merely illustrative, and not limitations of the preceding disclosure in any way whatsoever. Those skilled in the art will promptly recognize appropriate variations from the procedures.

Recombinant DNA techniques relating to the subject matter of the present invention and well known to those of ordinary skill in the art can be found, e.g, in Maniatis T et al., *Molecular Cloning: A. Laboratory Manual* (1989) Cold Spring Harbor Laboratory; U.S. Pat. No. 6,399,373; and PCT Application Number PCT/IB02/01461 published as WO 02/066505 on 29 Aug. 2002; the disclosure of each of which is herein incorporated by reference in its entirety.

Example 1

Full-Length Cloning of Endogenous Human GPR50

Polynucleotide encoding endogenous human GPR50 was cloned by reverse transcription polymerase chain reaction (RT-PCR) using the GPR50 specific primers 5'-GGAAAGCTTAACGATCCCCAGGAGCAACAT-3' (SEQ ID NO: 9; sense with HindIII site and the last two nucleotides being part of the initiation codon) and 5'-CTGG-GATCCTACGAGAGCATTTTTCACACAG-3' (SEQ ID NO: 10; antisense with BamHI site, TCA as antisense of stop codon)

and human pituitary cDNA (Clontech) as template. Cloned pfu DNA polymerase (Stratagene) was used for amplification by the following cycle with step 2 to step 4 repeated 25 times: 94° C., 3 minutes; 94° C., 1 minute; 62° C., 1 minute; 72° C., 3 minute; 72° C., 10 minutes.

A 1.9 Kb PCR fragment of predicted size was isolated, digested with HindIII and BamHI, and cloned into the pCMV expression vector and sequenced using the T7 DNA sequenase kit (Amersham). See, SEQ ID NO:1 for a first nucleic acid sequence obtained in this manner and SEQ ID NO:2 for the deduced amino acid sequence. See, SEQ ID NO:3 for a second nucleic acid sequence obtained in this manner and SEQ ID NO:4 for the deduced amino acid sequence.

Example 2

Receptor Expression

Although a variety of cells are available to the art for the expression of proteins, it is most preferred that mammalian cells or melanophores be utilized. The primary reason for this is predicated upon practicalities, i.e., utilization of, e.g., yeast cells for the expression of a GPCR, while possible, introduces into the protocol a non-mammalian cell which may not (indeed, in the case of yeast, does not) include the receptor-coupling, genetic-mechanism and secretary pathways that have evolved for mammalian systems—thus, results obtained in non-mammalian cells, while of potential use, are not as preferred as that obtained from mammalian cells or melanophores. Of the mammalian cells, CHO, COS-7, MCB3901, 293 and 293T cells are particularly preferred, although the specific mammalian cell utilized can be predicated upon the particular needs of the artisan. See infra as relates to melanophores, including Example 9.

a. Transient Transfection

On day one, $4 \times 10^6$ 293 cells per 10 cm dish are plated out. On day two, two reaction tubes are prepared (the proportions to follow for each tube are per plate): tube A is prepared by mixing 4 μg DNA (e.g., pCMV vector; pCMV vector comprising polynucleotide encoding a GPCR of the invention, etc.) in 0.5 ml serum free DMEM (Gibco BRL); tube B is prepared by mixing 24 μl lipofectamine (Gibco BRL) in 0.5 ml serum free DMEM. Tubes A and B are admixed by inversions (several times), followed by incubation at room temperature for 30-45 min. The admixture is referred to as the "transfection mixture". Plated 293 cells are washed with 1×PBS, followed by addition of 5 ml serum free DMEM. 1 ml of the transfection mixture is added to the cells, followed by incubation for 4 hrs at 37° C./5% $CO_2$. The transfection mixture is removed by aspiration, followed by the addition of 10 ml of DMEM/10% Fetal Bovine Serum. Cells are incubated at 37° C./5% $CO_2$. After 48 hr incubation, cells are harvested and utilized for analysis.

b. Stable Cell Lines

Approximately $12 \times 10^6$ 293 cells are plated on a 15 cm tissue culture plate. Grown in DME High Glucose Medium containing ten percent fetal bovine serum and one percent sodium pyruvate, L-glutamine, and antibiotics. Twenty-four hours following plating of 293 cells (or to ~80% confluency), the cells are transfected using 12 μg of DNA (e.g., pCMV-neo$^r$ vector comprising polynucleotide encoding a GPCR of the invention). The 12 μg of DNA is combined with 60 μl of lipofectamine and 2 ml of DME High Glucose Medium without serum. The medium is aspirated from the plates and the cells are washed once with medium without serum. The DNA, lipofectamine, and medium mixture are added to the plate along with 10 ml of medium without serum. Following incubation at 37° C. for four to five hours, the medium is aspirated and 25 ml of medium containing serum is added. Twenty-four hours following transfection, the medium is aspirated again, and fresh medium with serum is added. Forty-eight hours following transfection, the medium is aspirated and medium with serum is added containing geneticin (G418 drug) at a final concentration of 500 μm/ml. The transfected cells now undergo selection for positively transfected cells containing the G418 resistance gene. The medium is replaced every four to five days as selection occurs. During selection, cells are grown to create stable pools, or split for stable clonal selection.

Example 3

Assays for Determination of GPCR Activation (e.g., Screening Assays)

A variety of approaches are available for assessing activation of a GPCR of interest, or "target" GPCR. The following are illustrative; those of ordinary skill in the art are credited with the ability to determine those techniques that are preferentially beneficial for the needs of the artisan.

1. Membrane Binding Assays: [$^{35}$S]GTPγS Assay

When a G protein-coupled receptor is in its active state, either as a result of ligand binding or constitutive activation, the receptor couples to a G protein and stimulates the release of GDP and subsequent binding of GTP to the G protein. The alpha subunit of the G protein-receptor complex acts as a GTPase and slowly hydrolyzes the GTP to GDP, at which point the receptor normally is deactivated. Activated receptors continue to exchange GDP for GTP. The non-hydrolyzable GTP analog, [$^{35}$S]GTPγS, can be utilized to demonstrate enhanced binding of [$^{35}$S]GTPγS to membranes expressing activated receptors. The advantage of using [$^{35}$S]GTPγS binding to measure activation is that: (a) it is generically applicable to all G protein-coupled receptors; (b) it is proximal at the membrane surface making it less likely to pick-up molecules which affect the intracellular cascade.

The assay utilizes the ability of G protein coupled receptors to stimulate [$^{35}$S]GTPγS binding to membranes expressing the relevant receptors. The assay can, therefore, be used to screen candidate compounds as modulators of GPCRs. The assay is generic and has application to drug discovery at all G protein-coupled receptors.

The [$^{35}$S]GTPγS assay is incubated in 20 mM HEPES and between 1 and about 20 mM $MgCl_2$ (this amount can be adjusted for optimization of results, although 20 mM is preferred) pH 7.4, binding buffer with between about 0.3 and about 1.2 nM [$^{35}$S]GTPγS (this amount can be adjusted for optimization of results, although 1.2 is preferred) and 12.5 to 75 μg membrane protein (e.g, 293 cells expressing a GPCR of the invention; this amount can be adjusted for optimization) and 10 μM GDP (this amount can be changed for optimization) for 1 hour. Wheatgerm agglutinin beads (25 μl; Amersham) are then added and the mixture incubated for another 30 minutes at room temperature. The tubes are then centrifuged at 1500×g for 5 minutes at room temperature and then counted in a scintillation counter.

2. Adenylyl Cyclase

A Flash Plate™ Adenylyl Cyclase kit (New England Nuclear; Cat. No. SMP004A) designed for cell-based assays can be modified for use with crude plasma membranes. The Flash Plate wells can contain a scintillant coating which also contains a specific antibody recognizing cAMP. The cAMP generated in the wells can be quantitated by a direct competition for binding of radioactive cAMP tracer to the cAMP antibody. The following serves as a brief protocol for the measurement of changes in cAMP levels in whole cells that express the receptors.

Transfected cells are harvested approximately twenty-four to forty-eight hours after transient transfection. Media is carefully aspirated off and discarded. 10 ml of PBS is gently added to each dish of cells followed by careful aspiration. 1 ml of Sigma cell dissociation buffer and 3 ml of PBS are added to each plate. Cells are pipetted off the plate and the cell suspension is collected into a 50 ml conical centrifuge tube. Cells are then centrifuged at room temperature at 1,100 rpm for 5 min. The cell pellet is carefully re-suspended into an appropriate volume of PBS (about 3 ml/plate). The cells are then counted using a hemocytometer and additional PBS is added to give the appropriate number of cells (with a final volume of about 50 µl/well).

cAMP standards and Detection Buffer (comprising 1 µCi of tracer [$^{125}$I] cAMP (50 µl) to 11 ml Detection Buffer) is prepared and maintained in accordance with the manufacturer's instructions. Assay Buffer is prepared fresh for screening and contains 50 µl of Stimulation Buffer, 3 µl of test compound (12 µM final assay concentration) and 50 µl cells. Assay Buffer is stored on ice until utilized. The assay, preferably carried out e.g. in a 96-well plate, is initiated by addition of 50 µl of cAMP standards to appropriate wells followed by addition of 50 ul of PBS to wells H-11 and H12. 50 µl of Stimulation Buffer is added to all wells. DMSO (or selected candidate compounds) is added to appropriate wells using a pin tool capable of dispensing 3 µl of compound solution, with a final assay concentration of 12 µM test compound and 100 µl total assay volume. The cells are then added to the wells and incubated for 60 min at room temperature. 100 µl of Detection Mix containing tracer cAMP is then added to the wells. Plates are then incubated additional 2 hours followed by counting in a Wallac MicroBeta scintillation counter. Values of cAMP/well are then extrapolated from a standard cAMP curve which is contained within each assay plate.

3. Cell-Based cAMP Assay for Gi-Coupled Target GPCRs

TSHR is a Gs coupled GPCR that causes the accumulation of cAMP upon activation. TSHR will be constitutively activated by mutating amino acid residue 623 (i.e., changing an alanine residue to an isoleucine residue). A Gi coupled receptor is expected to inhibit adenylyl cyclase, and, therefore, decrease the level of cAMP production, which can make assessment of cAMP levels challenging. An effective technique for measuring the decrease in production of cAMP as an indication of activation of a Gi coupled receptor can be accomplished by co-transfecting, most preferably, non-endogenous, constitutively activated TSHR (TSHR-A623I) (or an endogenous, constitutively active Gs coupled receptor) as a "signal enhancer" with a Gi coupled Target GPCR to establish a baseline level of cAMP. The Gi coupled receptor is co-transfected with the signal enhancer, and it is this material that can be used for screening. Such an approach can be utilized to effectively generate a signal when a cAMP assay is used. In some embodiments, this approach is preferably used in the identification of candidate compounds against Gi coupled receptors. It is noted that for a Gi coupled GPCR, when this approach is used, an inverse agonist of the Target GPCR will increase the cAMP signal and an agonist will decrease the cAMP signal.

On day one, 4×10$^6$ 293 cells per 10 cm dish will be plated out. On day two, two reaction tubes will be prepared (the proportions to follow for each tube are per plate): tube A will be prepared by mixing 2 µg DNA of each receptor transfected into the mammalian cells, for a total of 4 µg DNA (e.g., pCMV vector; pCMV vector with mutated THSR (TSHR-A623I); TSHR-A623I and the Target GPCR, etc.) in 0.5 ml serum free DMEM (Irvine Scientific, Irvine, Calif.); tube B will be prepared by mixing 24 µl lipofectamine (Gibco BRL) in 0.5 ml serum free DMEM. Tubes A and B will then be admixed by inversions (several times), followed by incubation at room temperature for 30-45 min. The admixture is referred to as the "transfection mixture". Plated 293 cells will be washed with 1×PBS, followed by addition of 5 ml serum free DMEM. 1.0 ml of the transfection mixture will then be added to the cells, followed by incubation for 4 hrs at 37° C./5% $CO_2$. The transfection mixture will then be removed by aspiration, followed by the addition of 10 ml of DMEM/10% Fetal Bovine Serum. Cells will then be incubated at 37° C./5% $CO_2$. After approximately 24-48 hr incubation, cells will then be harvested and utilized for analysis.

A Flash Plate™ Adenylyl Cyclase kit (New England Nuclear; Cat. No. SMP004A) is designed for cell-based assays, but can be modified for use with crude plasma membranes depending on the need of the skilled artisan. The Flash Plate wells will contain a scintillant coating which also contains a specific antibody recognizing cAMP. The cAMP generated in the wells can be quantitated by a direct competition for binding of radioactive cAMP tracer to the cAMP antibody. The following serves as a brief protocol for the measurement of changes in cAMP levels in whole cells that express the receptors.

Transfected cells will be harvested approximately twenty-four to forty-eight hours after transient transfection. Media will be carefully aspirated off and discarded. 10 ml of PBS will be gently added to each dish of cells followed by careful aspiration. 1 ml of Sigma cell dissociation buffer and 3 ml of PBS will be added to each plate. Cells will be pipetted off the plate and the cell suspension will be collected into a 50 ml conical centrifuge tube. Cells will then be centrifuged at room temperature at 1,100 rpm for 5 min. The cell pellet will be carefully re-suspended into an appropriate volume of PBS (about 3 ml/plate). The cells will then be counted using a hemocytometer and additional PBS is added to give the appropriate number of cells (with a final volume of about 50µ/well).

cAMP standards and Detection Buffer (comprising 1 µCi of tracer [$^{125}$I] cAMP (50 µl) to 11 ml Detection Buffer) will be prepared and maintained in accordance with the manufacturer's instructions. Assay Buffer should be prepared fresh for screening and contained 50 µl of Stimulation Buffer, 3 µl of test compound (12 µM final assay concentration) and 50 µl cells, Assay Buffer can be stored on ice until utilized. The assay can be initiated by addition of 50 µl of cAMP standards to appropriate wells followed by addition of 50 µl of PBS to wells H-11 and H12. Fifty µl of Stimulation Buffer will be added to all wells. Selected compounds (e.g., TSH) will be added to appropriate wells using a pin tool capable of dispensing 3 µl of compound solution, with a final assay concentration of 12 µM test compound and 1000 total assay volume. The cells will then be added to the wells and incubated for 60 min at room temperature. 100 µl of Detection Mix containing tracer cAMP will then be added to the wells. Plates were then incubated additional 2 hours followed by counting in a Wallac MicroBeta scintillation counter. Values of cAMP/well will then be extrapolated from a standard cAMP curve which is contained within each assay plate.

4. Reporter-Based Assays a. CRE-Luc Reporter Assay (Gs-Associated Receptors)

293 and 293T cells are plated-out on 96 well plates at a density of 2×10$^4$ cells per well and were transfected using Lipofectamine Reagent (BRL) the following day according to manufacturer instructions. A DNA/lipid mixture is prepared for each 6-well transfection as follows: 260 ng of plasmid DNA in 100 μl of DMEM is gently mixed with 2 μl of lipid in 100 μl of DMEM (the 260 ng of plasmid DNA consists of 200 ng of a 8xCRE-Luc reporter plasmid, 50 ng of pCMV comprising endogenous receptor or non-endogenous receptor or pCMV alone, and 10 ng of a GPRS expression plasmid (GPRS in pcDNA3 (Invitrogen)). The 8XCRE-Luc reporter plasmid was prepared as follows: vector SRIF-β-gal was obtained by cloning the rat somatostatin promoter (−71/+51) at BglV-HindIII site in the pβgal-Basic Vector (Clontech). Eight (8) copies of cAMP response element were obtained by PCR from an adenovirus template AdpCF126CCRE8 [see, Suzuki et al., Hum Gene Ther (1996) 7:1883-1893; the disclosure of which is herein incorporated by reference in its entirety) and cloned into the SRIF-β-gal vector at the Kpn-BglV site, resulting in the 8xCRE-β-gal reporter vector. The 8xCRE-Luc reporter plasmid was generated by replacing the beta-galactosidase gene in the 8xCRE-β-gal reporter vector with the luciferase gene obtained from the pGL3-basic vector (Promega) at the HindIII-BamHI site. Following 30 min. incubation at room temperature, the DNA/lipid mixture is diluted with 400 μl of DMEM and 100 μl of the diluted mixture is added to each well. 100 μl of DMEM with 10% FCS are added to each well after a 4 hr incubation in a cell culture incubator. The following day the transfected cells are changed with 200 μl/well of DMEM with 10% FCS. Eight (8) hours later, the wells are changed to 100 μl/well of DMEM without phenol red, after one wash with PBS. Luciferase activity is measured the next day using the LucLite™ reporter gene assay kit (Packard) following manufacturer instructions and read on a 1450 MicroBeta™ scintillation and luminescence counter (Wallac).

b. AP1 Reporter Assay (Gq-Associated Receptors)

A method to detect Gq stimulation depends on the known property of Gq-dependent phospholipase C to cause the activation of genes containing AP1 elements in their promoter. A Pathdetect™ AP-1 cis-Reporting System (Stratagene, Catalogue #219073) can be utilized following the protocol set forth above with respect to the CREB reporter assay, except that the components of the calcium phosphate precipitate were 410 ng pAP1-Luc, 80 ng pCMV-receptor expression plasmid, and 20 ng CMV-SEAP (secreted alkaline phosphatase expression plasmid; alkaline phosphatase activity is measured in the media of transfected cells to control for variations in transfection efficiency between samples).

c. SRF-LUC Reporter Assay (Gq-Associated Receptors)

One method to detect Gq stimulation depends on the known property of Gq-dependent phospholipase C to cause the activation of genes containing serum response factors in their promoter. A Pathdetect™ SRF-Luc-Reporting System (Stratagene) can be utilized to assay for Gq coupled activity in, e.g., COS7 cells. Cells are transfected with the plasmid components of the system and the indicated expression plasmid encoding endogenous or non-endogenous GPCR using a Mammalian Transfection™ Kit (Stratagene, Catalogue #200285) according to the manufacturer's instructions. Briefly, 410 ng SRF-Luc, 80 ng pCMV-receptor expression plasmid and 20 ng CMV-SEAP are combined in a calcium phosphate precipitate as per the manufacturer's instructions. Half of the precipitate is equally distributed over 3 wells in a 96-well plate, kept on the cells in a serum free media for 24 hours. The last 5 hours the cells are incubated with, e.g. 1 μM, test compound. Cells are then lysed and assayed for luciferase activity using a Luclite™ Kit (Packard, Cat. #6016911) and "Trilux 1450 Microbeta" liquid scintillation and luminescence counter (Wallac) as per the manufacturer's instructions. The data can be analyzed using GraphPad Prism™ 2.0a (GraphPad Software Inc.).

d. Intracellular IP3 Accumulation Assay (Gq-Associated Receptors)

On day 1, cells comprising the receptors (endogenous or non-endogenous) can be plated onto 24 well plates, usually $1 \times 10^5$ cells/well (although his number can be optimized. On day 2 cells can be transfected by first mixing 0.25 μg DNA in 50 μl serum free DMEM/well and 2 μl lipofectamine in 50 μl serum free DMEM/well. The solutions are gently mixed and incubated for 15-30 min at room temperature. Cells are washed with 0.5 ml PBS and 400 μl of serum free media is mixed with the transfection media and added to the cells. The cells are then incubated for 3-4 hrs at 37° C./5% $CO_2$ and then the transfection media is removed and replaced with 1 ml/well of regular growth media. On day 3 the cells are labeled with $^3$H-myo-inositol. Briefly, the media is removed and the cells are washed with 0.5 ml PBS. Then 0.5 ml inositol-free/serum free media (GIBCO BRL) is added/well with 0.25 μCi of $^3$H-myo-inositol/well and the cells are incubated for 16-18 hrs o/n at 37° C./5% $CO_2$. On Day 4 the cells are washed with 0.5 ml PBS and 0.45 ml of assay medium is added containing inositol-free/serum free media 10 μM pargyline 10 mM lithium chloride or 0.4 ml of assay medium and optionally 50 μl of test compound to final concentration of 10 μM. The cells are then incubated for 30 min at 37° C. The cells are then washed with 0.5 ml PBS and 200 μl of fresh/ice cold stop solution (1M KOH; 18 mM Na-borate; 3.8 mM EDTA) is added/well. The solution is kept on ice for 5-10 min or until cells were lysed and then neutralized by 200 μl of fresh/ice cold neutralization sol. (7.5% HCL). The lysate is then transferred into 1.5 ml eppendorf tubes and 1 ml of chloroform/methanol (1:2) is added/tube. The solution is vortexed for 15 sec and the upper phase is applied to a Biorad AG1-X8™ anion exchange resin (100-200 mesh). Firstly, the resin is washed with water at 1:1.25 W/V and 0.9 ml of upper phase is loaded onto the column. The column is washed with 10 mls of 5 mM myo-inositol and 10 ml of 5 mM Na-borate/60 mM Na-formate. The inositol tris phosphates are eluted into scintillation vials containing 10 ml of scintillation cocktail with 2 ml of 0.1 M formic acid/1 M ammonium formate. The columns are regenerated by washing with 10 ml of 0.1 M formic acid/3M ammonium formate and rinsed twice with dd $H_2O$ and stored at 4° C. in water.

Example 4

Fusion Protein Preparation a. GPCR:Gs Fusion Construct

The design of the GPCR-G protein fusion construct can be accomplished as follows: both the 5' and 3' ends of the rat G protein Gsα (long form; Itoh, H. et al., 83 PNAS 3776 (1986)) are engineered to include a HindIII (5'-AAGCTT-3') sequence thereon. Following confirmation of the correct sequence (including the flanking HindIII sequences), the entire sequence is shuttled into pcDNA3.1(−) (Invitrogen, cat. no. V795-20) by subcloning using the HindIII restriction site of that vector. The correct orientation for the Gsα sequence is determined after subcloning into pcDNA3.1(−). The modified pcDNA3.1(−) containing the rat Gsα gene at HindIII sequence is then verified; this vector is now available as a "universal" Gsα protein vector. The pcDNA3.1(−) vector contains a variety of well-known restriction sites upstream of the HindIII site, thus beneficially providing the ability to insert, upstream of the Gs protein, the coding sequence of an endogenous, constitutively active GPCR. This same approach can be utilized to create other "universal" G protein vectors, and, of course, other commercially available or proprietary vectors known to the artisan can be utilized—the important criteria is that the sequence for the GPCR be upstream and in-frame with that of the G protein.

b. Gq(6 Amino Acid Deletion)/Gi Fusion Construct

A Gq(del)/Gi fusion construct is a chimeric G protein whereby the first six (6) amino acids of the Gq-protein α-subunit ("Gαq") are deleted and the last five (5) amino acids at the C-terminal end of Gαq are replaced with the corresponding amino acids of the Gαi subunit. A Gq(del)/Gi fusion construct will force an endogenous Gi coupled receptor to couple to its non-endogenous G protein, Gq (in the form of Gq(del)/Gi), such that the second messenger, for example, inositol triphosphate or diacylglycerol or $Ca^{2+}$, can be measured in lieu of cAMP production.

The Gq(del)/Gi fusion construct was designed as follows: the N-terminal six (6) amino acids (amino acids 2 through 7, having the sequence of TLESIM (SEQ ID NO: 11) of the Gαq-subunit were deleted and the C-terminal five (5) amino acids, having the sequence EYNLV (SEQ ID NO: 12) were replaced with the corresponding amino acids of the Gαi Protein, having the sequence DCGLF (SEQ ID NO: 13). This fusion construct was obtained by PCR using the following primers:
5'-gatcaagcttcCATGGCGTGCTGCCTGAGCGAGGAG-3' (SEQ ID NO: 14) and
5'-gatcggatccTTAGAACAGGCCGCAGTC-CTTCAGGTTCAGCTGCAGGATGGTG-3' (SEQ ID NO: 15) and Plasmid 63313 (ATCC® Number 63313) which contains the mouse Gαq-wild-type version with a hemagglutinin tag as a template. Nucleotides in lower case include cloning sites for HindIII/BamHI and spacers.

TaqPlus Precision DNA polymerase (Stratagene) was utilized for the amplification by the following cycles, with steps 2 through 4 repeated 35 times: 95° C. for 2 min; 95° C. for 20 sec; 56° C. for 20 sec; 72° C. for 2 min; and 72° C. for 7 min. The PCR product was cloned into a pCRII-TOPO vector (Invitrogen) and sequenced using the ABI Big Dye Terminator kit (P. E. Biosystems). Inserts from a TOPO clone containing the sequence of the fusion construct was shuttled into the expression vector pcDNA3.1(+) at the HindIII/BamHI site by a 2 step cloning process. See, SEQ ID NO: 16 for the nucleic acid sequence and SEQ ID NO: 17 for the encoded amino acid sequence of Gq(del)/Gi construct.

Example 5

[$^{35}$S]GTPγS Assay

1. Membrane Preparation

In some embodiments membranes comprising a Target GPCR and for use in the identification of candidate compounds as, e.g., inverse agonists, agonists, or antagonists, are preferably prepared as follows:

a. Materials

"Membrane Scrape Buffer" is comprised of 20 mM HEPES and 10 mM EDTA, pH 7.4; "Membrane Wash Buffer" is comprised of 20 mM HEPES and 0.1 mM EDTA, pH 7.4; "Binding Buffer" is comprised of 20 mM HEPES, 100 mM NaCl, and 10 mM $MgCl_2$, pH 7.4.

b. Procedure

All materials will be kept on ice throughout the procedure. Firstly, the media will be aspirated from a confluent monolayer of cells, followed by rinse with 10 ml cold PBS, followed by aspiration. Thereafter, 5 ml of Membrane Scrape Buffer will be added to scrape cells; this will be followed by transfer of cellular extract into 50 ml centrifuge tubes (centrifuged at 20,000 rpm for 17 minutes at 4° C.). Thereafter, the supernatant will be aspirated and the pellet will be resuspended in 30 ml Membrane Wash Buffer followed by centrifuge at 20,000 rpm for 17 minutes at 4° C. The supernatant will then be aspirated and the pellet resuspended in Binding Buffer. This will then be homogenized using a Brinkman Polytron™ homogenizer (15-20 second bursts until the all material is in suspension). This is referred to herein as "Membrane Protein".

2. Bradford Protein Assay

Following the homogenization, protein concentration of the membranes will be determined using the Bradford Protein Assay (protein can be diluted to about 1.5 mg/ml, aliquoted and frozen (−80° C.) for later use; when frozen, protocol for use will be as follows: on the day of the assay, frozen Membrane Protein is thawed at room temperature, followed by vortex and then homogenized with a Polytron at about 12×1,000 rpm for about 5-10 seconds; it is noted that for multiple preparations, the homogenizer should be thoroughly cleaned between homogenization of different preparations).

a. Materials

Binding Buffer (as per above); Bradford Dye Reagent; Bradford Protein Standard will be utilized, following manufacturer instructions (Biorad, cat. no. 500-0006).

b. Procedure

Duplicate tubes will be prepared, one including the membrane, and one as a control "blank". Each contained 800 μl Binding Buffer. Thereafter, 10 μl of Bradford Protein Standard (1 mg/ml) will be added to each tube, and 10 μl of membrane Protein will then be added to just one tube (not the blank). Thereafter, 200 μl of Bradford Dye Reagent will be added to each tube, followed by vortex of each. After five (5) minutes, the tubes will be re-vortexed and the material therein will be transferred to cuvettes. The cuvettes will then be read using a CECIL 3041 spectrophotometer, at wavelength 595 nm.

3. Identification Assay a. Materials

GDP Buffer consists of 37.5 ml Binding Buffer and 2 mg GDP (Sigma, cat. no. G-7127), followed by a series of dilutions in Binding Buffer to obtain 0.2 μM GDP (final concentration of GDP in each well was 0.1 μM GDP); each well comprising a candidate compound, has a final volume of 200 μl consisting of 100 μl GDP Buffer (final concentration, 0.1 μM GDP), 50 μl Membrane Protein in Binding Buffer, and 50 μl [$^{35}$S]GTPγS (0.6 nM) in Binding Buffer (2.5 [$^{35}$S]GTPγS per 10 ml Binding Buffer).

b. Procedure

Candidate compounds will be preferably screened using a 96-well plate format (these can be frozen at −80° C.). Membrane Protein (or membranes with expression vector excluding the Target GPCR, as control), will be homogenized briefly until in suspension. Protein concentration will then be determined using the Bradford Protein Assay set forth above. Membrane Protein (and control) will then be diluted to 0.25 mg/ml in Binding Buffer (final assay concentration, 12.5 μg/well). Thereafter, 100 μl GDP Buffer is added to each well of a Wallac Scintistrip™ (Wallac). A 5 μl pin-tool will then be used to transfer 5 μA of a candidate compound into such well (i.e., 5 μl in total assay volume of 200 μl is a 1:40 ratio such that the final screening concentration of the candidate compound is 10 μM). Again, to avoid contamination, after each transfer step the pin tool should be rinsed in three reservoirs comprising water (1×), ethanol (1×) and water (2×)—excess liquid should be shaken from the tool after each rinse and dried with paper and kimwipes. Thereafter, 50 µl of Membrane Protein will be added to each well (a control well comprising membranes without the Target GPCR was also utilized), and pre-incubated for 5-10 minutes at room temperature. Thereafter, 50 µl of [$^{35}$S]GTPγS (0.6 nM) in Binding Buffer will be added to each well, followed by incubation on a shaker for 60 minutes at room temperature (again, in this example, plates were covered with foil). The assay will then be stopped by spinning of the plates at 4000 RPM for 15 minutes at 22° C. The plates will then be aspirated with an 8 channel manifold and sealed with plate covers. The plates will then be read on a Wallac 1450 using setting "Prot. #37" (as per manufacturer's instructions).

Example 6

Cyclic AMP Assay

Another assay approach for identifying candidate compounds as, e.g., inverse agonists, agonists, or antagonists, is accomplished by utilizing a cyclase-based assay. In addition to so identifying candidate compounds, this assay approach can be utilized as an independent approach to provide confirmation of the results from the [$^{35}$S]GTPγS approach as set forth in Example 5, supra.

A modified Flash Plate™ Adenylyl Cyclase kit (New England Nuclear; Cat. No. SMP004A) is preferably utilized for identification of candidate compounds as modulators of a Target GPCR in accordance with the following protocol.

Cells transfected with the Target GPCR are harvested approximately three days after transfection. Membranes are prepared by homogenization of suspended cells in buffer containing 20 mM HEPES, pH 7.4 and 10 mM $MgCl_2$. Homogenization is performed on ice using a Brinkman Polytron™ for approximately 10 seconds. The resulting homogenate is centrifuged at 49,000×g for 15 minutes at 4° C. The resulting pellet is then resuspended in buffer containing 20 mM HEPES, pH 7.4 and 0.1 mM EDTA, homogenized for 10 seconds, followed by centrifugation at 49,000×g for 15 minutes at 4° C. The resulting pellet is then stored at −80° C. until utilized. On the day of direct identification screening, the membrane pellet is slowly thawed at room temperature, resuspended in buffer containing 20 mM HEPES, pH 7.4 and 10 mM $MgCl_2$, to yield a final protein concentration of 0.60 mg/ml (the resuspended membranes are placed on ice until use).

cAMP standards and Detection Buffer (comprising 2 µCi of tracer {[$^{125}$I]cAMP (100 µl) to 11 ml Detection Buffer] are prepared and maintained in accordance with the manufacturer's instructions. Assay Buffer is prepared fresh for screening and contains 20 mM HEPES, pH 7.4, 10 mM $MgCl_2$, 20 mM phosphocreatine (Sigma), 0.1 units/ml creatine phosphokinase (Sigma), 50 µM GTP (Sigma), and 0.2 mM ATP (Sigma); Assay Buffer is then stored on ice until utilized.

Candidate compounds are added, preferably, to e.g. 96-well plate wells (3 µl/well; 12 µM final assay concentration), together with 40 µl Membrane Protein (30 µg/well) and 50 µl of Assay Buffer. This admixture was then incubated for 30 minutes at room temperature, with gentle shaking.

Following the incubation, 100 µl of Detection Buffer is added to each well, followed by incubation for 2-24 hours. Plates are then counted in a Wallac MicroBeta™ plate reader using "Prot. #31" (as per manufacturer's instructions).

By way of example and not limitation, an illustrative screening assay plate (96 well format) result obtained is presented in FIG. 1. Each bar represents the result for a compound that differs in each well, the "Target GPCR" being a Gsα Fusion Protein construct of an endogenous, constitutively active Gs-coupled GPCR unrelated to GPR50. The results presented in FIG. 1 also provide standard deviations based upon the mean results of each plate ("m") and the mean plus two arbitrary preference for selection of inverse agonists as "leads" from the primary screen involves selection of candidate compounds that that reduce the percent response by at least the mean plate response, minus two standard deviations. Conversely, an arbitrary preference for selection of agonists as "leads" from the primary screen involves selection of candidate compounds that increase the percent response by at least the mean plate response, plus the two standard deviations. Based upon these selection processes, the candidate compounds in the following wells were directly identified as putative inverse agonist (Compound A) and agonist (Compound B) to said endogenous GPCR in wells A2 and G9, respectively. See, FIG. 1. It is noted for clarity: these compounds have been directly identified without any knowledge of the endogenous ligand for this GPCR. By focusing on assay techniques that are based upon receptor function, and not compound binding affinity, it is possible to ascertain compounds that are able to reduce the functional activity of this receptor (Compound A) as well as increase the functional activity of the receptor (Compound B).

Example 7

Fluorometric Imaging Plate Reader (FLIPR) Assay for the Measurement of Intracellular Calcium Concentration Target Receptor (experimental) and pCMV (negative control) stably transfected cells from respective clonal lines are seeded into poly-D-lysine pretreated 96-well plates (Becton-Dickinson, #356640) at $5.5 \times 10^4$ cells/well with complete culture medium (DMEM with 10% FBS, 2 mM L-glutamine, 1 mM sodium pyruvate) for assay the next day. To prepare Fluo4-AM (Molecular Probe, #F14202) incubation buffer stock, 1 mg Fluo4-AM is dissolved in 467 µl DMSO and 467 µl Pluoronic acid (Molecular Probe, #P3000) to give a 1 nM stock solution that can be stored at −20° C. for a month. Fluo4-AM is a fluorescent calcium indicator dye.

Candidate compounds are prepared in wash buffer (1×HBSS/2.5 mM Probenicid/20 mM HEPES at pH 7.4).

At the time of assay, culture medium is removed from the wells and the cells are loaded with 100 µl of 4 µM Fluo4-AM/ 2.5 mM Probenicid (Sigma, #P8761)/20 mM HEPES/complete medium at pH 7.4. Incubation at 37° C./5% $CO_2$ is allowed to proceed for 60 min.

After the 1 hr incubation, the Fluo4-AM incubation buffer is removed and the cells are washed 2× with 100 µl wash buffer. In each well is left 100 µl wash buffer. The plate is returned to the incubator at 37° C./5% $CO_2$ for 60 min.

FLIPR (Fluorometric Imaging Plate Reader; Molecular Device) is programmed to add 50 µl candidate compound on the 30th second and to record transient changes in intracellular calcium concentration ([$Ca^{2+}$]) evoked by the candidate compound for another 150 seconds. Total fluorescence change counts are used to determine agonist activity using the FLIPR software. The instrument software normalizes the fluorescent reading to give equivalent initial readings at zero. By way of illustration and not limitation, the skilled artisan would appreciate that a candidate compound can be screened as an antagonist of the receptor by assessing its ability to inhibit the transient increase in intracellular ([$Ca^{2+}$]) evoked by subsequent contact with a known agonist. In some embodiments, the cells comprising Target Receptor further comprise Gα15, Gα16, or Gq(del)/Gi chimeric G protein.

Although the foregoing provides a FLIPR assay for agonist activity using stably transfected cells, a person of ordinary skill in the art would readily be able to modify the assay in order to characterize antagonist activity. The person of ordinary skill in the art would also readily appreciate that, alternatively, transiently transfected cells could be used.

Example 8

MAP Kinase Assay

MAP kinase (mitogen activated kinase) may be monitored to evaluate receptor activation. MAP kinase can be detected by several approaches. One approach is based on an evaluation of the phosphorylation state, either unphosphorylated (inactive) or phosphorylated (active). The phosphorylated protein has a slower mobility in SDS-PAGE and can therefore be compared with the unstimulated protein using Western blotting. Alternatively, antibodies specific for the phosphorylated protein are available (New England Biolabs) which can be used to detect an increase in the phosphorylated kinase. In either method, cells are stimulated with the test compound and then extracted with Laemmli buffer. The soluble fraction is applied to an SDS-PAGE gel and proteins are transferred electrophoretically to nitrocellulose or Immobilin. Immunoreactive bands are detected by standard Western blotting technique. Visible or chemiluminescent signals are recorded on film and may be quantified by densitometry.

Another approach is based on evaluation of the MAP kinase activity via a phosphorylation assay. Cells are stimulated with the test compound and a soluble extract is prepared. The extract is incubated at 30° C. for 10 min with gamma-$^{32}$P-ATP, an ATP regenerating system, and a specific substrate for MAP kinase such as phosphorylated heat and acid stable protein regulated by insulin, or PHAS-I. The reaction is terminated by the addition of $H_3PO_4$ and samples are transferred to ice. An aliquot is spotted onto Whatman P81 chromatography paper, which retains the phosphorylated protein. The chromatography paper is washed and counted for $^{32}$P is a liquid scintillation counter. Alternatively, the cell extract is incubated with gamma-$^{32}$P-ATP, an ATP regenerating system, and biotinylated myelin basic protein bound by streptavidin to a filter support. The myelin basic protein is a substrate for activated MAP kinase. The phosphorylation reaction is carried out for 10 min at 30° C. The extract can then be aspirated through the filter, which retains, the phosphorylated myelin basic protein. The filter is washed and counted for $^{32}$P by liquid scintillation counting.

Example 9

Melanophore Technology

Melanophores are skin cells found in lower vertebrates. They contain pigmented organelles termed melanosomes. Melanophores are able to redistribute these melanosomes along a microtubule network upon G-protein coupled receptor (GPCR) activation. The result of this pigment movement is an apparent lightening or darkening of the cells. In melanophores, the decreased levels of intracellular cAMP that result from activation of a Gi-coupled receptor cause melanosomes to migrate to the center of the cell, resulting in a dramatic lightening in color. If cAMP levels are then raised, following activation of a Gs-coupled receptor, the melanosomes are re-dispersed and the cells appear dark again. The increased levels of diacylglycerol that result from activation of Gq-coupled receptors can also induce this re-dispersion. In addition, the technology is also suited to the study of certain receptor tyrosine kinases. The response of the melanophores takes place within minutes of receptor activation and results in a simple, robust color change. The response can be easily detected using a conventional absorbance microplate reader or a modest video imaging system. Unlike other skin cells, the melanophores derive from the neural crest and appear to express a full complement of signaling proteins. In particular, the cells express an extremely wide range of G-proteins and so are able to functionally express almost all GPCRs.

Melanophores can be utilized to identify compounds, including natural ligands, against GPCRs. This method can be conducted by introducing test cells of a pigment cell line capable of dispersing or aggregating their pigment in response to a specific stimulus and expressing an exogenous clone coding for the GCPR. A stimulant, e.g., melatonin, sets an initial state of pigment disposition wherein the pigment is aggregated within the test cells if activation of the GPCR induces pigment dispersion. However, stimulating the cell with a stimulant to set an initial state of pigment disposition wherein the pigment is dispersed if activation of the GPCR induces pigment aggregation. The test cells are then contacted with chemical compounds, and it is determined whether the pigment disposition in the cells changed from the initial state of pigment disposition. Dispersion of pigments cells due to the candidate compound, including but not limited to a ligand, coupling to the GPCR will appear dark on a petri dish, while aggregation of pigments cells will appear light.

Materials and methods can be followed according to the disclosure of U.S. Pat. No. 5,462,856 and U.S. Pat. No. 6,051,386. These patent disclosures are herein incorporated by reference in their entirety.

The cells are plated in e.g. 96-well plates (one receptor per plate). 48 hours post-transfection, half of the cells on each plate are treated with 10 nM melatonin. Melatonin activates an endogenous Gi-coupled receptor in the melanophores and causes them to aggregate their pigment. The remaining half of the cells are transferred to serum-free medium 0.7× L-15 (Gibco). After one hour, the cells in serum-free media remain in a pigment-dispersed state while the melatonin-treated cells are in a pigment-aggregated state. At this point, the cells are treated with a dose response of a test/candidate compound. If the plated GPCRs bind to the test/candidate compound, the melanophores would be expected to undergo a color change in response to the compound. If the receptor were either a Gs or Gq coupled receptor, then the melatonin-aggregated melanophores would undergo pigment dispersion. In contrast, if the receptor was a Gi-coupled receptor, then the pigment-dispersed cells would be expected to undergo a dose-dependent pigment aggregation.

Example 10

Transgenic Mouse/Rat/Pig Comprising a Disruption in a GPR50 Gene

Mouse

A preferred DNA construct will comprise, from 5'-end to 3'-end: (a) a first nucleotide sequence that is comprised in the mouse GPR50 genomic sequence; (b) a nucleotide sequence comprising a positive selection marker, such as the marker for neomycin resistance (neo); and (c) a second nucleotide sequence that is comprised in the mouse GPR50 genomic sequence and is located on the genome downstream of the first mouse GPR50 nucleotide sequence (a). Mouse GPR50 genomic sequence will be isolated using methods well known to those of ordinary skill in the art (Maniatis T et al., *Molecular Cloning: A Laboratory Manual* (1989) Cold Spring Harbor Laboratory; the disclosure of which is hereby incorporated by reference in its entirety). Probes for said isolation of mouse GPR50 genomic sequence will be derived from cDNA encoding a mouse GPR50 polypeptide, wherein said cDNA may be obtained using as template mRNA from mouse heart, lung, or adipose tissue.

In preferred embodiments, this DNA construct also comprises a negative selection marker located upstream the nucleotide sequence (a) or downstream the nucleotide sequence (c). Preferably, the negative selection marker comprises the thymidine kinase (tk) gene [Thomas et al., Cell (1986) 44:419-28], the hygromycin beta gene [Te Riele et al., Nature (1990) 348:649-51], the hprt gene [Van der Lugt et al., Gene (1991) 105:263-7; Reid et al., Proc Natl Acad Sci USA (1990) 87:4299-4303] or the Diptheria toxin A fragment (Dt-A) gene [Nada et al., Cell (1993) 73:1125-35; Yagi et al., Proc Natl Acad Sci USA (1990) 87:9918-9922], which disclosures are hereby incorporated by reference in their entireties. Preferably, the positive selection marker is located within a mouse GPR50 exon sequence so as to interrupt the sequence encoding a mouse GPR50 polypeptide. These replacement vectors are described, for example, by Thomas et al., Cell (1986) 44:419-28; Thomas et al., Cell (1987) 51:503-12; Mansour et al., Nature (1988) 336:348-52; Koller et al., Annu Rev Immunol (1992) 10:705-30; and U.S. Pat. No. 5,631,153; which disclosures are hereby incorporated by reference in their entireties.

The first and second nucleotide sequences (a) and (c) may be indifferently located within a mouse GPR50 regulatory sequence, an intronic sequence, an exon sequence or a sequence containing both regulatory and/or intronic and/or exon sequences. The size of the nucleotide sequences (a) and (c) ranges from 1 to 50 kb, preferably from 1 to 10 kb, more preferably from 2 to 6 kb, and most preferably from 2 to 4 kb.

Methods of making a transgenic mouse comprising disruption in a selected gene are well known to those of ordinary skill in the art and have been used to successfully inactivate a wide range of genes.

Rat

Analogous or alternative [see, e.g., Zan et al, Nature Biotechnology (2003) 21:645-51; the disclosure of which is hereby incorporated by reference in its entirety] methods may be used to make a transgenic rat comprising a disruption in a GPR50 gene.

Pig

Analogous or alternative methods may be used to make a transgenic pig comprising a disruption in a GPR50 gene [see, e.g., Lai et al., Science (2002) 295:1089-1092; the disclosure of which is hereby incorporated by reference in its entirety].

Example 11

Endogenous GPR50 Exhibits Constitutive Activity for Decreasing a Level of Intracellular Camp Thyroid-stimulating hormone (TSH, or thyrotropin) receptor (TSHR) causes the accumulation of intracellular cAMP on activation by its ligand TSH. An effective technique for measuring the decrease in production of cAMP corresponding to activation of a receptor such as GPR50 is to co-transfect TSHR with GPR50 and to carry out the assay in the presence of TSH to raise the level of basal cAMP, whereby TSHR acts as a "signal window enhancer." Such an approach was used here.

Human HEK293 cells were co-transfected with thyroid-stimulating hormone (TSH, or thyrotropin) receptor (TSHR) and either pCMV vector or a cDNA plasmid encoding endogenous GPR50. Transfection was carried out using Lipofectamine (Invitrogen). Forty-eight hours after transfection, the cells were stimulated with various concentrations of niacin and 100 nM TSH (Sigma) for 1 h before whole cell cAMP was determined using the Adenylyl Cyclase Flashplate Assay kit from Perkin Elmer catalog #:SMP004B], as described below.

The transfected cells were placed into anti-cAMP antibody-coated wells that contained 100 nM TSH and either niacin at various concentrations or vehicle. All conditions were tested in triplicate. After a 1 h incubation at room temperature to allow for stimulation of cAMP, a Detection Mix (provided in the Perkin Elmer kit) containing $^{125}$I-cAMP was added to each well and the plate was allowed to incubate for another hour at room temperature. The wells were then aspirated to remove unbound $^{125}$I-cAMP. Bound $^{125}$I-cAMP was detected using a Wallac Microbeta Counter. The amount of cAMP in each sample was determined by comparison to a standard curve, obtained by placing known concentrations of cAMP in some wells on the plate. Results are presented in FIG. 2.

As shown in FIG. 2, endogenous GPR50 is detectably constitutively active, exhibiting constitutive activity for decreasing a level of intracellular cAMP.

Example 12

Establishment of GPR50—Knockout ("Deficient") Mice

GPR50-knockout ("deficient") mice were established as described here.

A targeting vector was generated by inactivating the entire exon 2 and flanking intronic sequences and replacing it by a neomycin resistant cassette (see, FIG. 3A). In FIG. 3A, nucleotide numbering shown in small italics represents chromosome location according to Mouse Geneview: http://www.en-sembl.org/Mus_musculus/index.html.

The targeting vector was inserted into C57Bl/6J embryonic stem (ES) cells by electroporation. Positive clones were isolated and exon 2 deletion was verified by Southern blot. To check targeting at the 3' end, Southern blot analysis was performed on EcoRV-digested genomic DNA from ES cells with a 854-bp DNA fragment ("3' external probe" as shown in FIG. 3A). Correctly targeted cells demonstrated a ~7.8 kb modified band (due to the introduction of an EcoRV site at the 5' end of the 3' arm). The 15.9 kb wild-type band was absent from targeted clones since GPR50 is X-linked.

To further verify that the exon 2 sequence had been deleted, Southern blot analysis was performed on EcoRI-digested genomic ES cells DNA with a 1031 bp DNA fragment ("internal probe" as shown in FIG. 3A) that contained most of the exon 2 sequence. As GPR50 is X-linked, no band was detected in correctly targeted clones, whereas a 7.1 kb band was detected in wild-type cells. All Southern blots were performed following previously published methods [see, e.g., Sambrook et al, Molecular Cloning: a Laboratory Manual (1989) Second Edition, Cold Spring Harbor, N.Y.: CSH Laboratory Press; the disclosure of which is herein incorporated by reference in its entirety].

Targeted and karyotypically normal ES cells were then microinjected into Balb/c I/B and the injected blastocysts were transferred into the uteri of surrogate C57B1/6 mother mice. Male chimeras were bred to female C57B1/6J to generate F1 mice and germline transmission of GPR50 exon 2 deletion was further verified by PCR on mouse tail genomic DNA.

Five specific primer sets from different areas of GPR50 genomic sequence were generated ("#1" to "#5" as shown in FIG. 3A). Primer sequences are shown in Table D below. Only primers #3-#5 should be detected in knockout mice, whereas all primers except #5 should be detected in wild-type mice. Tail were cut from mice and genomic DNA isolated using phenol/chloroform extraction according to Sambrook et al 1989 (supra). PCR reaction was performed using the PCR Supermix from Invitrogen (Carlsbad, Calif.), 200 ng/µl of each of the forward and reverse primers and 100-500 ng genomic DNA in a reaction volume of 50 µl. The PCR products were run on 1.8% agarose gel to check for the presence or absence of the amplified product for each primer pair and to verify the expected size. Results are shown in FIG. 3B.

Results shown in FIG. 3B confirm that GPR50-knockout ("deficient") mice were established.

That GPR50-knockout ("deficient") mice were established was also confirmed by in situ hybridization analysis of GPR50 expression in hypothalamus.

TABLE D

| Primer Set | Primer | Primer Sequence |
|---|---|---|
| #1 Exon 2 (451 bp) | Forward Primer | TGCCATCAACCGTTACTGCTAC (SEQ ID NO: 18) |
| | Reverse Primer | GGGGATCTTGCCTGCCATTT (SEQ ID NO: 19) |
| #2 Exon 2 (511 bp) | Forward Primer | GCTCGTGCCTGTGTCGCTGTG (SEQ ID NO: 20) |
| | Reverse Primer | CAAGGCAATGGGAGGCTGAGA (SEQ ID NO: 21) |
| #3 Exon 1 (418 bp) | Forward Primer | CATTCGGCTGCATTGGCTGTAA (SEQ ID NO: 22) |
| | Reverse Primer | ACTCCGTTCCTGTGGCGACTTC (SEQ ID NO: 23) |
| #4 3' Intron (518 bp) | Forward Primer | GCAGGCTGGGCTCATCTTAGGTAT (SEQ ID NO: 24) |
| | Reverse Primer | TCTGGGATTTTGGGCTTGATGTGT (SEQ ID NO: 25) |
| #5 Neo cassette (515 bp) | Forward Primer | GGGCGCCCGGTTCTTTTTG (SEQ ID NO: 26) |
| | Reverse Primer | ACACCCAGCCGGCCACAGTCG (SEQ ID NO: 27) |

Example 13

Body Weight of GPR50—Knockout Mice on High Fat Diet or Chow Compared to Wild-Type Mice on High Fat Diet An effect of GPR50 activity on weight gain induced by a high fat diet is shown in FIG. 4. Three groups of 30 week old male mice were housed individually and allowed free access to water and food. The mice were maintained on a 12 hour artificial light/12 h dark cycle and kept under constant humidity (70%) and temperature (22° C.) conditions. A first group of wild-type C57B1/6J mice (n=6) ("WT" in FIG. 4) and a second group of GPR50-knockout mice (n=2) ("KO" in FIG. 4) were allowed free access to high fat diet ("HFD" in FIG. 4) (D12266B, Research Diet, 31.8% fat/Kcal), while a third group of GPR50-knockout mice (n=3) were allowed access to chow pellets ("Chow" in FIG. 4) (Teklab 8604, 4.4% fat) for 15 weeks.

Figure 4A:
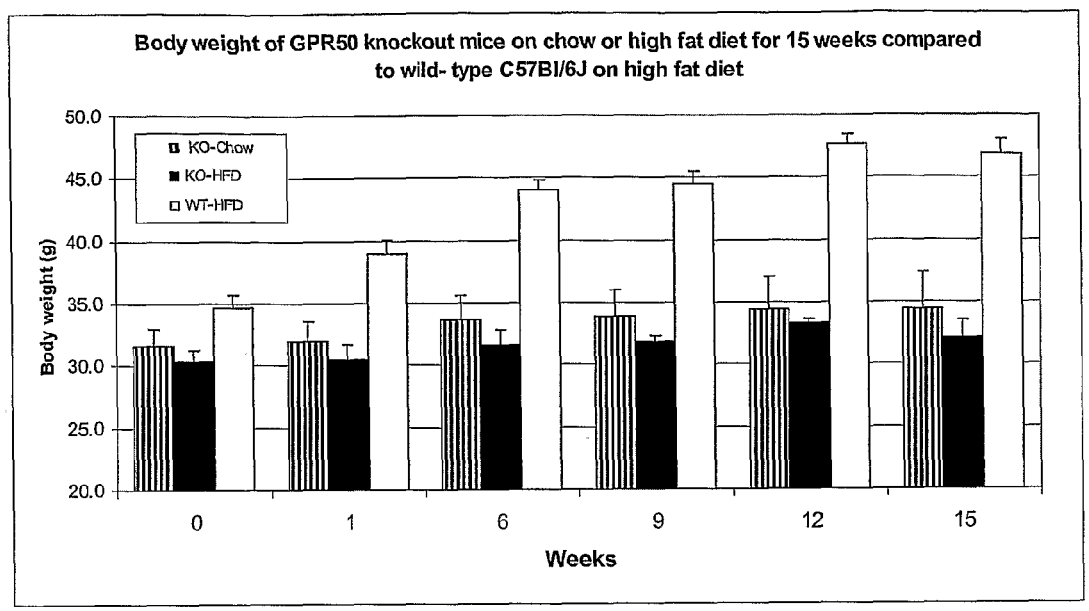
FIGS. 4A and 4B. Body weight of GPR50-knockout mice on high fat diet or chow compared to wild-type mice on high fat diet. (See, Example 13.)
Figure 4B:
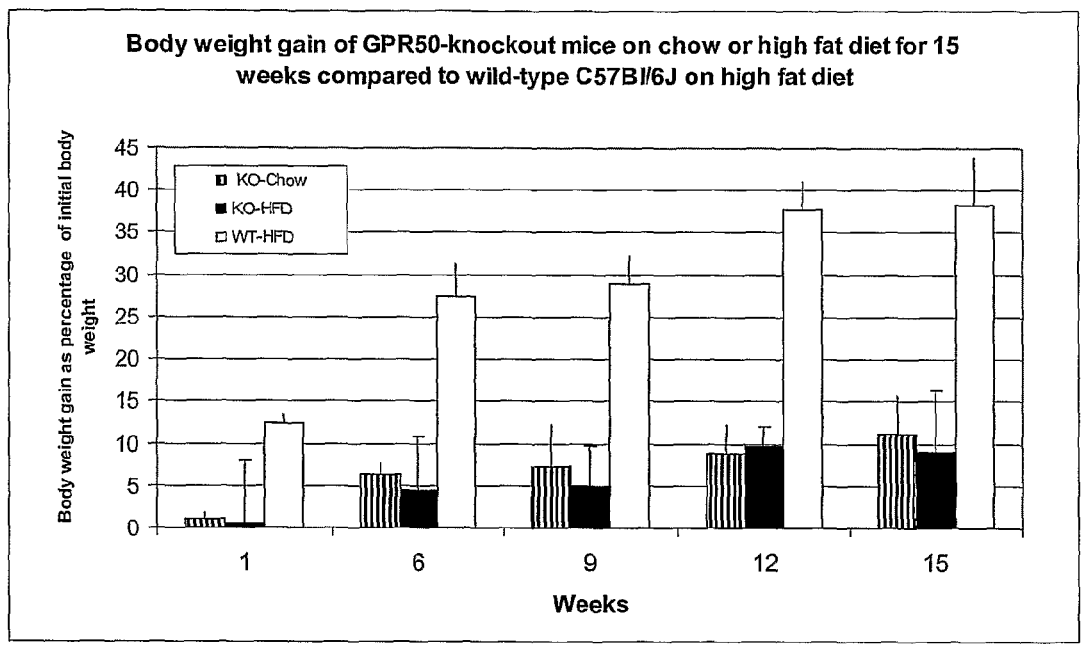

Body weight is shown in FIG. 4A as mean±SEM. Body weight gain as a percentage of initial body weight is shown in FIG. 4B as mean±SEM. It is apparent from inspection of FIG. 4 (for example, comparison of the GPR50-knockout mice on the high fat diet with the wild-type C57B1/6J mice on the high fat diet) that loss of GPR50 activity in the GPR50-knockout mice conferred protection from (that is, decreased) weight gain induced by a high fat diet.

Figure 5A:
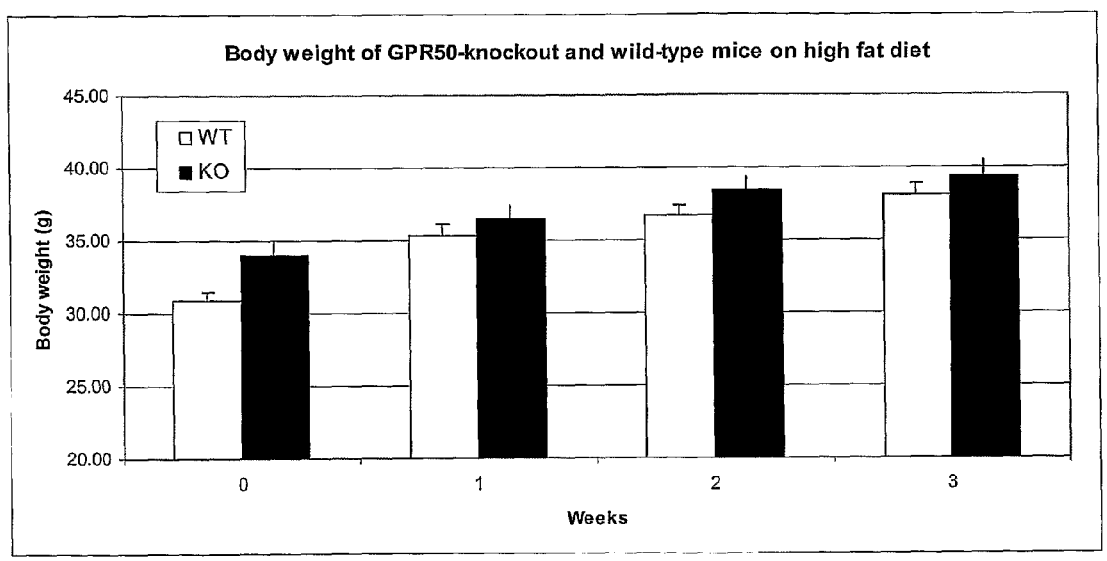
FIGS. 5A and 5B. Comparison of body weight of GPR50-knockout mice and wild-type mice on high fat diet. (See, Example 13.)
Figure 5B:
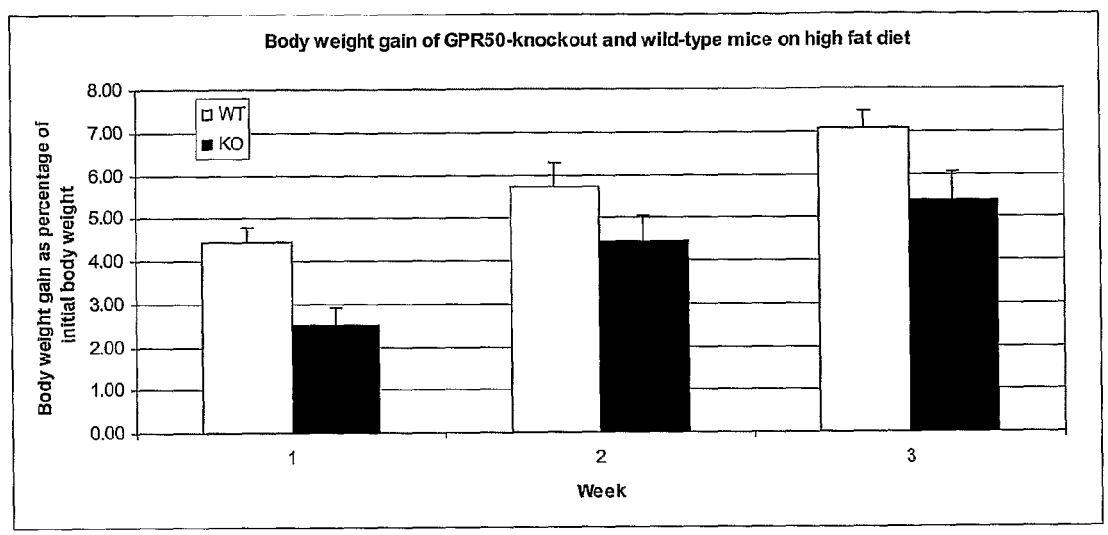

An analogous experiment carried out in 70 wk old male GPR50-knockout ("KO") (n=6) and wild-type littermate ("WT") (n=6) mice on the high fat diet (D12266B, Research Diet, 31.8% fat/Kcal) for three weeks is shown in FIG. 5.

Example 14

In Vivo Effects of a GPR50 Inverse Agonist or Antagonist on Increased Adiposity Induced by a High-Fat Diet in Mice An inverse agonist or antagonist of GPR50 can be shown to confer protection from increased adiposity induced by a high fat diet. Two groups of age- and sex-matched 5-30 week old wild-type C57B1/6J mice are housed individually and allowed free access to water and food. The mice are maintained on a 12 hour artificial light/12 h dark cycle and kept under constant humidity (70%) and temperature (22° C.) conditions. Mice are allowed free access to high fat diet (D12266B, Research Diet, 31.8% fat/Kcal), for a period of 4-15 weeks. Over the course of the 4-15 week period, an inverse agonist or antagonist of GPR50 having inverse agonist or antagonist activity at mouse GPR50 or vehicle alone is injected daily into the tail vein. A preferred dose of the GPR50 inverse agonist or antagonist is 0.1-100 mg/kg. Other preferred dose is selected from the group consisting of 0.1 mg/kg, 0.3 mg/kg, 1.0 mg/kg, 3.0 mg/kg, 10 mg/kg, 30 mg/kg and 100 mg/kg.

At the conclusion of the 4-15 week period, the mice are euthanized by $CO_2$ inhalation, and the epididymal and inguinal footpads are harvested and weighed as a measure of adiposity. The results can demonstrate that the GPR50 inverse agonist or antagonist confers protection from (that is, decreases) the increased adiposity (increased weight of the epididymal and inguinal footpads) induced by a high fat diet.

It is expressly contemplated that the GPR50 inverse agonist or antagonist can be a selective GPR50 inverse agonist or antagonist. It is expressly contemplated that a high fat diet having less or more than 31.8% fat/Kcal can be used. It is expressly contemplated that administration of the inverse agonist or antagonist can be other than intravenous, for example that administration of the inverse agonist or antagonist can be intraperitoneal or oral. It is expressly contemplated that mice younger than 5 weeks or older than 30 weeks can be used. It is expressly contemplated that the period of injection can be less than 4 weeks or longer than 15 weeks. It is expressly contemplated that a non-human mammal other than mouse can be used, for example rat.

Example 15

In Vivo Effects of a GPR50 Inverse Agonist or Antagonist on Increased Percentage Body Fat Induced by a High-Fat Diet in Mice An inverse agonist or antagonist of GPR50 can be shown to confer protection from increased percentage body fat induced by a high fat diet. Two groups of age- and sex-matched 5-30 week old wild-type C57B1/6J mice are housed individually and allowed free access to water and food. The mice are maintained on a 12 hour artificial light/12 h dark cycle and kept under constant humidity (70%) and temperature (22° C.) conditions. Mice are allowed free access to high fat diet (D12266B, Research Diet, 31.8% fat/Kcal), for a period of 4-15 weeks. Over the course of the 4-15 week period, an inverse agonist or antagonist of GPR50 having inverse agonist or antagonist activity at mouse GPR50 or vehicle alone is injected daily into the tail vein. A preferred dose of the GPR50 inverse agonist or antagonist is 0.1-100 mg/kg. Other preferred dose is selected from the group consisting of 0.1 mg/kg, 0.3 mg/kg, 1.0 mg/kg, 3.0 mg/kg, 10 mg/kg, 30 mg/kg and 100 mg/kg.

At the conclusion of the 4-15 week period, the mice are euthanized by $CO_2$ inhalation and percentage body fat is evaluated by determining body composition by densitometry using Dual energy X-ray absorptiometry (DEXA) (Lunar PIXImus, Lunar PIXImus Corp., Madison, Wis.). The data are analyzed using Lunar PIXImus 2.2.0 software according to the manufacturer's instructions. The results can demonstrate that the GPR50 inverse agonist or antagonist confers protection from (that is, decreases) the increased percentage body fat induced by a high fat diet.

It is expressly contemplated that the GPR50 inverse agonist or antagonist can be a selective GPR50 inverse agonist or antagonist. It is expressly contemplated that a high fat diet having less or more than 31.8% fat/Kcal can be used. It is expressly contemplated that administration of the inverse agonist or antagonist can be other than intravenous, for example that administration of the inverse agonist or antagonist can be intraperitoneal or oral. It is expressly contemplated that mice younger than 5 weeks or older than 30 weeks can be used. It is expressly contemplated that the period of injection can be less than 4 weeks or longer than 15 weeks. It is expressly contemplated that a non-human mammal other than mouse can be used, for example rat.

Example 16

In vivo Effects of a GPR50 Inverse Agonist or Antagonist on Weight Gain Induced by a High-Fat Diet in Mice An inverse agonist or antagonist of GPR50 can be shown to confer protection from weight gain induced by a high fat diet. Two groups of age- and sex-matched 5-30 week old wild-type C57B1/6J mice are housed individually and allowed free access to water and food. The mice are maintained on a 12 hour artificial light/12 h dark cycle and kept under constant humidity (70%) and temperature (22° C.) conditions. Mice are allowed free access to high fat diet (D12266B, Research Diet, 31.8% fat/Kcal), for a period of 4-15 weeks. Over the course of the 4-15 week period, an inverse agonist or antagonist of GPR50 having inverse agonist or antagonist activity at mouse GPR50 or vehicle alone is injected daily into the tail vein. A preferred dose of the GPR50 inverse agonist or antagonist is 0.1-100 mg/kg. Other preferred dose is selected from the group consisting of 0.1 mg/kg, 0.3 mg/kg, 1.0 mg/kg, 3.0 mg/kg, 10 mg/kg, 30 mg/kg and 100 mg/kg.

At weekly intervals over the course of the 4-15 week period, the mice are weighed. The results can demonstrate that the GPR50 inverse agonist or antagonist confers protection from (that is, decreases) weight gain induced by a high fat diet.

It is expressly contemplated that the GPR50 inverse agonist or antagonist can be a selective GPR50 inverse agonist or antagonist. It is expressly contemplated that a high fat diet having less or more than 31.8% fat/Kcal can be used. It is expressly contemplated that administration of the inverse agonist or antagonist can be other than intravenous, for example that administration of the inverse agonist or antagonist can be intraperitoneal or oral. It is expressly contemplated that mice younger than 5 weeks or older than 30 weeks can be used. It is expressly contemplated that the period of injection can be less than 4 weeks or longer than 15 weeks. It is expressly contemplated that a non-human mammal other than mouse can be used, for example rat.

Example 17

Analysis of Co-Expression of GPR50 by NPY Neurons in the Central Part of the Dorsomedial Nucleus of the Hypothalamus (DMHc) in Rat Co-expression of GPR50 by neuropeptide-Y (NPY) neurons in the central part of the dorsomedial nucleus of the hypothalamus (DMHc) in rat was investigated by in situ hybridization, using radiolabeled antisense probe for GPR50 in combination with a digoxigenin (Dig)-labeled antisense probe for NPY. Rat GPR50 probe corresponding to nucleotides 397 to 918 of SEQ ID NO: 7 was inserted into pBS vector (Stratagene, La Jolla, Calif.). Rat NPY probe corresponding to rat NPY cDNA sequence (511 nucleotides) spanning the coding sequence (see, e.g., GenBank®Accession No. NM_012614) was inserted into pBS vector (Stratagene). In situ hybridization was carried out essentially as described below.

Rats were killed by rapid decapitation 1-2 h after initiation of the light cycle. Brains were removed, frozen in isopentane (−40° C.), and stored at −80° C. Serial 12-µm sections from the central part of the dorsomedial nucleus of the hypothalamus (DMHc) were prepared on a cryostat, thaw-mounted onto polylysine-subbed slides, and stored at −80° C. until processing.

Sense and antisense $^{33}P$ radiolabeled probes were generated by in vitro transcription by incubating linearized plasmids in transcription buffer containing RNasin (40 units), DTT (2 mM), ATP, CIT and GTP (0.33 mM), [α-$^{33}P$]-UTP (Perkin Elmer, 50 µCi, NEG307 H001MC) and the appropriate polymerase (T7 50 units or T3 20 units). Probes were DNase treated, purified by ethanol precipitation and resuspend in 2× hybridization buffer (8×SET, 2×Denhardt's, 0.4% SDS, 200 mM dithiothreitol (DTT), 500 ug/ml tRNA, 50 ug/ml polyA, 50 ug/ml polyC).

Antisense digoxigenin labeled probes were generated by in vitro transcription by incubating linearized plasmids in transcription buffer containing RNasin (40 units), DTT (2 mM), nucleotide mix containing digoxigenin labeled UTP (rNTP digoxigenin RNA labeling mix, Roche #1277073) and the appropriate polymerase (T7 50 units or T3 20 units). Probes were DNase treated and cleaned up through a centrisep column (Princeton Separations, # CS-901).

Tissue sections were removed from the freezer and allow to air dry for 15 min. Sections were subsequently fixed in 4% paraformaldehyde in phosphate buffer (0.1 M, pH 7.4) for 30 min at room temperature, rinsed 3 times in 1×PBS, and acetylated in 0.1 M triethanolamine (TEA), pH 8.0 for 2 min then briefly in the same buffer containing 0.25% acetic anhydride.

Slides were then rinsed for 5 minutes in 1×PBS and then dehydrated through graded alcohol concentrations and air dried. Radiolabeled probes were diluted in 2× hybridization buffer to yield an approximate concentration of $16 \times 10^6$ cpm per slide. Salmon sperm was added at a final concentration of 20 ug/slide and digoxigenin labeled probe was added to a final concentration of 500 ng/slide. Dextran sulfate/Formamide (20%) was added to give a 1:1 ratio with 2× hybridization buffer. Diluted probe was placed on slides, coverslipped and were incubated at 55° C. for 16-18 hours in plastic trays humidified with 1×PBS. Coverslips were floated off with 1 mM DTT/4×SSC (600 mM sodium chloride and 60 mM sodium citrate, pH 7.2) and sections were subsequently washed once in 4×SSC for 10 min, incubated in ribonuclease A (200 ug/ml) for 60 min in a 37° C. water bath, then rinsed in 2×, 1×, and 0.5×SSC for 5 minutes each. Sections were washed to a final stringency of 0.1×SSC at 65° C. for 1 hour, then washed twice in 0.1×SSC then washed in TN (100 mM Tris, pH 7.5, 150 mM NaCl) for 5 minutes. Sections were then placed in 0.5% Casein/TN blocking solution for 30 minutes then incubated for 2 hours with anti-digoxigenin-AP antibody (Roche, #1093274) diluted 1:300 in 0.5% Casein/TN solution. Sections were then washed 3 times, 2 minutes each in TN and then 3 times 5 minutes each in TNM (100 mM Tris, pH 9.5, 100 mM NaCl, 50 mM $MgCl_2$). After the last wash, sections were incubated in color reaction (0.2 mg/ml levamisole, 3.4 ul/ml NBT (Roche #1383213), 3.5 ul/ml BCIP (Roche #1383221) in TNM and 0.22 u sterile filtered) for 20-30 minutes and reaction stopped in TE for 30 minutes. Antibody was striped off by incubating sections in 0.1M glycine and 0.5% triton-X 100 for 10 minutes and washed in water. Sections were fixed in 2.5% glutaraldehyde for 1-2 hours and washed with water then air dried. Once section dried, they were exposed to x-ray sensitive film (Bio-Max, Kodak, Eastman Kodak Co., Rochester, N.Y.) for 2-7 days and dipped in photographic emulsion (Ilford Scientific K.5D Emulsion in gel form from Polysciences, #17537) dried and stored in slides box with desiccant at 4° C. for 4-8 weeks depending on the level of expression. After development of dipped slides following manufacturer recommendations (Kodak D19), sections were washed extensively in water and air dried then mounted with coverslips for microscopic examination.

Images of the distribution of GPR50 and NPY mRNA-containing cells were obtained using an Olympus BX51 microscope connected to a videocamera (NTSC 750CE) using Stereoinvestigator® v6.55.2 software (Microbrightfield, Vt.). Nonradioactive riboprobes were visualized under brightfield as a purple precipitate, and radioactive probes were visualized under darkfield by silver grain distribution.

A representative photomicrographic image illustrating the expression of GPR50 and NPY in the central part of the dorsomedial nucleus of the hypothalamus (DMHc) in rat is presented in FIG. 6A. Note the presence of neurons expressing only GPR50 (open arrowhead), neurons expressing only NPY (solid arrowhead), and neurons co-expressing GPR50 and NPY (arrow).

The percentage of NPY neurons in rat DMHc co-expressing GPR50 ("double GPR50/NPY") was estimated by analysis of tissue sections from each of two rats, as shown in FIG. 6B. For each rat, analysis was carried out on two consecutive sections a and b at position 1 and on two consecutive sections a and b at position 2, with position 1 and position 2 being separated by 120 microns. The percentage of NPY neurons co-expressing GPR50 was taken as the average ±SEM of the percentages for the individual slides and was determined to be 54.3±2.8, as set forth in FIG. 6B.

Example 18

Yeast Reporter Assay for GPR50Modulator (e.g., Inverse Agonist or Antagonist) Activity The yeast cell-based reporter assays have previously been described in the literature (e.g., see Miret et al, J Biol Chem (2002) 277:6881-6887; Campbell et al, Bioorg Med Chem Lett (1999) 9:2413-2418; King et al, Science (1990) 250:121-123; WO 99/14344; WO 00/12704; and U.S. Pat. No. 6,100,042). Briefly, yeast cells have been engineered such that the endogenous yeast G-alpha (GPA1) has been deleted and replaced with G-protein chimeras constructed using multiple techniques. Additionally, the endogenous yeast alpha-cell GPCR, Step 3 has been deleted to allow for a homologous expression of a mammalian GPCR of choice. In the yeast, elements of the pheromone signaling transduction pathway, which are conserved in eukaryotic cells (for example, the mitogen-activated protein kinase pathway), drive the expression of Fus1. By placing β-galactosidase (LacZ) under the control of the Fus1 promoter (Fus1p), a system has been developed whereby receptor activation leads to an enzymatic readout.

Yeast cells are transformed by an adaptation of the lithium acetate method described by Agatep et al (Agatep et al, 1998, Transformation of *Saccharomyces cerevisiae* by the lithium acetate/single-stranded carrier DNA/polyethylene glycol (LiAc/ss-DNA/PEG) protocol. Technical Tips Online, Trends Journals, Elsevier). Briefly, yeast cells are grown overnight on yeast tryptone plates (YT). Carrier single-stranded DNA (10 μg), 2 μg of each of two Fus1p-LacZ reporter plasmids (one with URA selection marker and one with TRP), 2 μg of GPR50 (e.g., human receptor) in yeast expression vector (2 μg origin of replication) and a lithium acetate/polyethylene glycol/TE buffer is pipetted into an Eppendorf tube. The yeast expression plasmid containing the receptor/no receptor control has a LEU marker. Yeast cells are inoculated into this mixture and the reaction proceeds at 30° C. for 60 min. The yeast cells are then heat-shocked at 42° C. for 15 min. The cells are then washed and spread on selection plates. The selection plates are synthetic defined yeast media minus LEU, URA and TRP(SD-LUT). After incubating at 30° C. for 2-3 days, colonies that grow on the selection plates are then tested in the LacZ assay.

In order to perform fluorimetric enzyme assays for β-galactosidase, yeast cells carrying the subject GPR50 receptor are grown overnight in liquid SD-LUT medium to an unsaturated concentration (i.e. the cells are still dividing and have not yet reached stationary phase). They are diluted in fresh medium to an optimal assay concentration and 90 μl of yeast cells are added to 96-well black polystyrene plates (Costar). Test compounds, dissolved in DMSO and diluted in a 10% DMSO solution to 10× concentration, are added to the plates and the plates placed at 30° C. for 4 h. After 4 h, the substrate for the β-galactosidase is added to each well. In these experiments, Fluorescein di (β-D-galactopyranoside) is used (FDG), a substrate for the enzyme that releases fluorescein, allowing a fluorimetric read-out. 20 μl per well of 500 μM FDG/2.5% Triton X100 is added (the detergent is necessary to render the cells permeable). After incubation of the cells with the substrate for 60 min, 200 per well of 1M sodium carbonate is added to terminate the reaction and enhance the fluorescent signal. The plates are then read in a fluorimeter at 485/535 nm.

A decrease in fluorescent signal in GPR50-transformed yeast cells over that in yeast cells transformed with empty vector is indicative of a test compound being a compound that inhibits GPR50 receptor functionality (e.g., a compound that is an inverse agonist or antagonist of GPR50). In certain embodiments, compounds of the invention give a decrease in fluorescent signal below that of the background signal (the signal obtained in the presence of vehicle alone).

An increase in fluorescent signal in GPR50-transformed yeast cells over that in yeast cells transformed with empty vector is indicative of a test compound being a compound that stimulates GPR50 receptor functionality (e.g., a compound that is an agonist or partial agonist of GPR50). In certain embodiments, compounds of the invention give an increase in fluorescent signal above that of the background signal (the signal obtained in the presence of vehicle alone).

Example 19

Receptor Binding Assay

A test compound can be evaluated for its ability to reduce formation of the complex between a compound known to be a ligand of a G protein-coupled receptor of the invention and the receptor. In certain embodiments, the known ligand is radiolabeled. The radiolabeled known ligand can be used in a screening assay to identify/evaluate compounds. In general terms, a newly synthesized or identified compound (i.e., test compound) can be evaluated for its ability to reduce binding of the radiolabeled known ligand to the receptor, by its ability to reduce formation of the complex between the radiolabeled known ligand and the receptor.

In other aspect, a test compound can be radiolabeled and shown to be a ligand of a subject GPCR of the invention by evaluating its ability to bind to a cell comprising the subject GPCR or to membrane comprising the subject GPCR.

A level of specific binding of the radiolabled known ligand in the presence of the test compound less than a level of specific binding of the radiolabeled known ligand in the absence of the test compound is indicative of less of the complex between said radiolabeled known ligand and said receptor being formed in the presence of the test compound than in the absence of the test compound.

Assay Protocol for Detecting the Complex Between a Compound Known to be a Ligand of a G Protein-Coupled Receptor of the Invention and the Receptor A. Preparation of the Receptor 293 cells are transiently transfected with 10 ug expression vector comprising a polynucleotide encoding a G protein-coupled receptor of the invention using 60 ul Lipofectamine (per 15-cm dish). The transiently transfected cells are grown in the dish for 24 hours (75% confluency) with a media change and removed with 10 ml/dish of Hepes-EDTA buffer (20 mM Hepes+10 mM EDTA, pH 7.4). The cells are then centrifuged in a Beckman Coulter centrifuge for 20 minutes, 17,000 rpm (JA-25.50 rotor). Subsequently, the pellet is resuspended in 20 mM Hepes+1 mM EDTA, pH 7.4 and homogenized with a 50-ml Dounce homogenizer and again centrifuged. After removing the supernatant, the pellets are stored at −80° C., until used in binding assay. When used in the assay, membranes are thawed on ice for 20 minutes and then 10 mL of incubation buffer (20 mM Hepes, 1 mM $MgCl_2$, 100 mM NaCl, pH 7.4) added. The membranes are then vortexed to resuspend the crude membrane pellet and homogenized with a Brinkmann PT-3100 Polytron homogenizer for 15 seconds at setting 6. The concentration of membrane protein is determined using the BRL Bradford protein assay.

B. Binding Assay

For total binding, a total volume of 50 ul of appropriately diluted membranes (diluted in assay buffer containing 50 mM Tris HCl (pH 7.4), 10 mM $MgCl_2$, and 1 mM EDTA; 5-50 ug protein) is added to 96-well polyproylene microtiter plates followed by addition of 100 ul of assay buffer and 50 ul of a radiolabeled known ligand. For nonspecific binding, 50 ul of assay buffer is added instead of 100 ul and an additional 50 ul of 10 uM said known ligand which is not radiolabeled is added before 50 ul of said radiolabeled known ligand is added. Plates are then incubated at room temperature for 60-120 minutes. The binding reaction is terminated by filtering assay plates through a Microplate Devices GF/C Unifilter filtration plate with a Brandell 96-well plate harvestor followed by washing with cold 50 mM Tris HCl, pH 7.4 containing 0.9% NaCl. Then, the bottom of the filtration plate are sealed, 50 ul of Optiphase Supermix is added to each well, the top of the plates are sealed, and plates are counted in a Trilux MicroBeta scintillation counter. For determining whether less of the complex between said radiolabeled known ligand and said receptor is formed in the presence of a test compound, instead of adding 100 ul of assay buffer, 100 ul of appropriately diluted said test compound is added to appropriate wells followed by addition of 50 ul of said radiolabled known ligand.

Example 20

Analysis of the Effect of Food Restriction on the Expression of GPR50 in the Central Part of the Dorsomedial Nucleus of the Hypothalamus (DMHC) in Rat The effect of food restriction on the expression of GPR50 in the central part of the dorsomedial nucleus of the hypothalamus (DMHc) in rat was determined by in situ hybridization. The effect of food restriction on the expression of neuropeptide-Y (NPY), an orexigenic molecule, was also determined. Tissue sections of the DMHc were prepared essentially as described supra in Example 17, as was in situ hybridization carried out using $^{33}P$ radiolabeled antisense probe.

Twenty week old male Sprague Dawley rats were divided into two groups of seven rats each, housed in cages singly. One group, the ad libitum fed group, was provided an unrestricted amount of food (Teklab 8604, 4.4% fat) each day over a period of twelve days. A second group, the food-restricted group, was provided 16 g of the same food each day (70% of the average daily food intake of the rats under ad libitum conditions) over the same twelve day period. Food was provided in the morning. The amount of food intake in the rats during the previous 24 hour period also was determined in the morning. The weight of the rats also was determined in the morning. The food intake in the ad libitum fed and in the food-restricted rats is shown in the upper panel of FIG. 7A. The percentage of original body weight in the rats (that is, the body weight of the rat expressed as the percentage of its body weight at the initiation of the experiment, Day 0) is shown in the lower panel of FIG. 7A. From inspection of FIG. 7A, it is apparent that food restriction evidenced as declining body weight in the food-restricted rats.

Figure 7B:
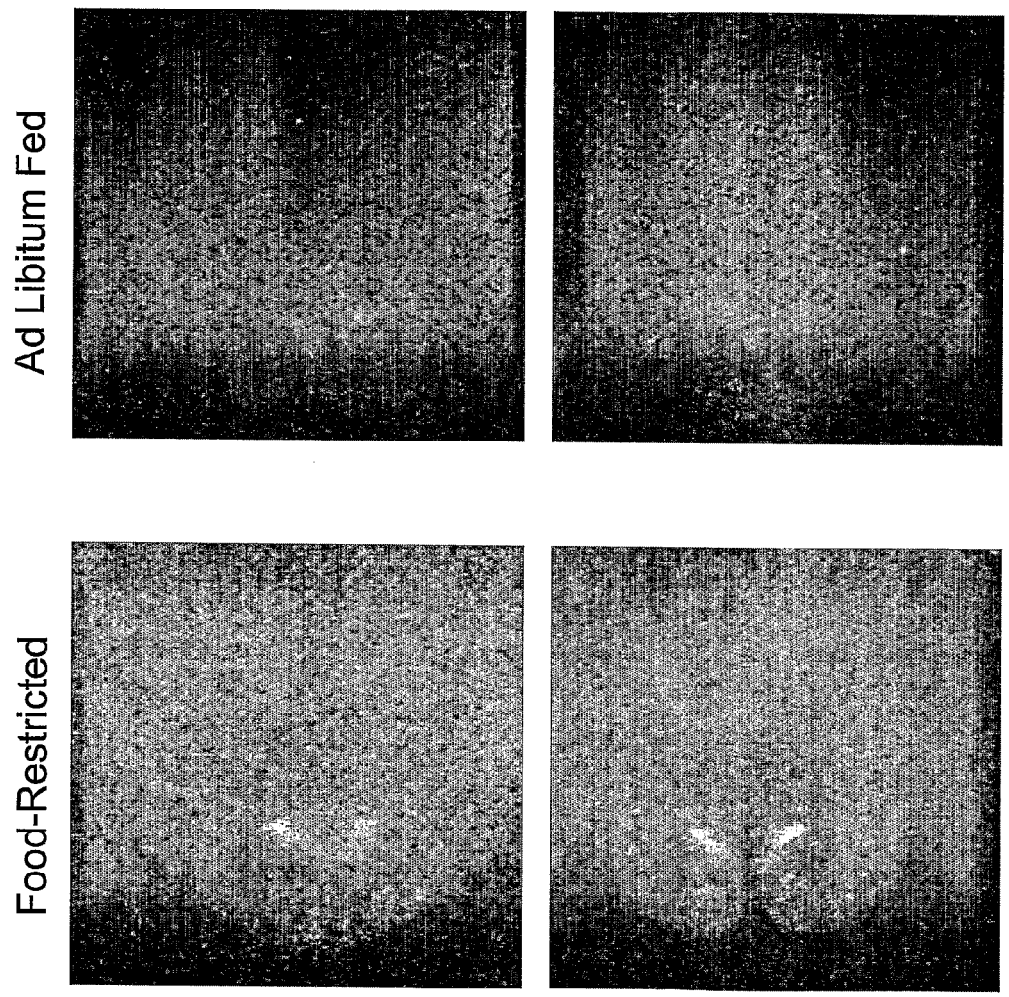

At the end of the twelve day period, the rats were sacrificed. Tissue sections of the DMHc were prepared and subjected to in situ hybridization with $^{33}P$ radiolabeled GPR50 antisense probe or with $^{33}P$ radiolabeled NPY antisense probe. Sense probe was used as a specificity control. Bound radioactive probe was visualized under darkfield by silver grain distribution. Representative photomicrographic images from two different rats in the ad libitum fed group and from two different rats in the food-restricted group are shown in FIG. 7B for GPR50. From inspection of FIG. 7B, it is apparent that food restriction led to marked up-regulation of GPR50 expression in the DMHc.

The relative levels of GPR50 mRNA expression in the DMHc for the ad libitum fed and food-restricted groups as evidenced by the in situ hybridization were determined using Scion Image Version 1.63 analysis of autoradiogram optical density, and the results are presented in the lower panel of FIG. 7C. The relative levels of NPY mRNA expression in the DMHc were likewise determined for the ad libitum fed and food-restricted groups, and the results are presented in the upper panel of FIG. 7C. From inspection of FIG. 7C, it is apparent that food restriction led to marked up-regulation of GPR50 expression in the DMHc and that this up-regulated GPR50 expression was associated in the DMHc with up-regulated expression of NPY.

What is claimed is:

1. A method of identifying a candidate compound for the modulation of body mass or adiposity in a mammal, comprising the steps of:
   (a) contacting the compound with a G protein-coupled receptor (GPCR) comprising an amino acid sequence having at least 80% identity to SEQ ID NO: 2; wherein the receptor couples to a G protein;
   (b) determining the ability of the compound to inhibit or stimulate functionality of the GPCR; and
   (c) identifying a compound that inhibits or stimulates functionality of the GPCR as a candidate compound for the modulation of body mass or adiposity in a mammal.

2. The method of claim 1, wherein the method comprises detecting a second messenger.

3. The method of claim 1, wherein said determining is by a process comprising the use of a melanophore assay or by a process comprising the measurement of GTPγS binding to a membrane comprising the GPCR.

4. The method of claim 1, wherein said contacting comprises contacting the compound with a recombinant eukaryotic host cell comprising the GPCR or with a membrane thereof that comprises the GPCR.

5. The method of claim 1, wherein the method further comprises formulating said compound as a pharmaceutical composition.

6. The method of claim 1, wherein the compound is a non-naturally occurring compound.

7. The method of claim 6, wherein the GPCR comprises an amino acid sequence having at least 95% identity to SEQ ID NO: 2.

8. The method of claim 6, wherein the compound is an antagonist of the GPCR.

9. The method of claim 6, wherein the compound is an inverse agonist of the GPCR.

10. The method of claim 1, wherein the compound inhibits functionality of the GPCR.

11. The method of claim 1, wherein the compound stimulates functionality of the GPCR.

12. A method comprising:
   (a) administering to a mammal a compound which inhibits functionality of a G protein-coupled receptor (GPCR) comprising an amino acid sequence having at least 80% identity to SEQ ID NO: 2, wherein the receptor couples to a G protein; and
   (b) determining whether the compound confers protection from weight gain in the mammal.

13. The method of claim 12, wherein the compound is a non-naturally occurring compound.

14. The method of claim 13, wherein the GPCR comprises an amino acid sequence having at least 95% identity to SEQ ID NO: 2.

15. The method of claim 12, wherein the method further comprises formulating the compound as a pharmaceutical composition.

16. The method of claim 12, wherein the determining step (b) comprises measuring protection from weight gain induced by a high fat diet.

17. The method of claim 12, wherein the mammal has a condition selected from: cachexia, wasting, AIDS-related weight loss, cancer-related weight loss, anorexia, and bulimia.

18. A method comprising:
   (a) administering to a mammal a compound which stimulates functionality of a G protein-coupled receptor (GPCR) comprising an amino acid sequence having at least 80% identity to SEQ ID NO: 2, wherein the receptor couples to a G protein; and
   (b) determining whether the compound increases body mass in the mammal.

19. The method of claim 18, wherein the compound is a non-naturally occurring compound.

20. The method of claim 19, wherein the GPCR comprises an amino acid sequence having at least 95% identity to SEQ ID NO: 2.

21. The method of claim 18, wherein the method further comprises formulating the compound as a pharmaceutical composition.

22. The method of claim 18, wherein the mammal has a condition selected from: cachexia, wasting, AIDS-related weight loss, cancer-related weight loss, anorexia, and bulimia.

23. A method of identifying a compound as an agent for modulating body mass or adiposity in a mammal, comprising:
   (a) administering to a mammal a compound that inhibits functionality of a G protein-coupled receptor (GPCR) comprising an amino acid sequence having at least 80% identity to SEQ ID NO: 2, wherein the compound is a non-naturally occurring compound; and
   (b) determining whether the compound modulates body mass or adiposity in the mammal.

24. The method of claim 23, wherein the method further comprises formulating the compound as a pharmaceutical composition.

25. The method of claim 23, wherein the mammal is overweight or obese.

26. The method of claim 23, wherein the mammal has a condition selected from: hypertension, insulin resistance, metabolic syndrome, Type 2 diabetes, dyslipidemia, atherosclerosis, coronary heart disease, and stroke.

27. The method of claim 23, wherein the determining step (b) comprises measuring weight loss in said mammal.

28. The method of claim 23, wherein the determining step (b) comprises measuring protection from weight gain induced by a high fat diet.

\* \* \* \* \*